US010420829B2

(12) United States Patent
Caldwell et al.

(10) Patent No.: US 10,420,829 B2
(45) Date of Patent: Sep. 24, 2019

(54) CHLAMYDIA VACCINE

(71) Applicant: The United States of America, as represented by the Secretary, Department of Health & Human Services, Washington, DC (US)

(72) Inventors: Harlan D. Caldwell, Hamilton, MT (US); Deborah Crane, Hamilton, MT (US)

(73) Assignee: The United States of America, as represented by the Secretary, Department of Health & Human Services, Rockville, MD (US)

( * ) Notice: Subject to any disclaimer, the term of this patent is extended or adjusted under 35 U.S.C. 154(b) by 0 days.

(21) Appl. No.: 15/043,975

(22) Filed: Feb. 15, 2016

(65) Prior Publication Data

US 2017/0021007 A1 Jan. 26, 2017

Related U.S. Application Data

(60) Division of application No. 12/087,952, filed on Oct. 1, 2010, now Pat. No. 9,259,463, which is a continuation of application No. PCT/US2007/001213, filed on Jan. 16, 2007.

(60) Provisional application No. 60/760,970, filed on Jan. 16, 2006.

(51) Int. Cl.

| | |
|---|---|
| ***A61K 39/118*** | (2006.01) |
| ***C07K 14/295*** | (2006.01) |
| ***C07K 16/12*** | (2006.01) |
| ***A61K 39/00*** | (2006.01) |

(52) U.S. Cl.

CPC .......... *A61K 39/118* (2013.01); *C07K 14/295* (2013.01); *C07K 16/125* (2013.01); *A61K 2039/505* (2013.01); *A61K 2039/5158* (2013.01); *A61K 2039/5256* (2013.01); *A61K 2039/54* (2013.01); *A61K 2039/575* (2013.01); *C07K 2317/76* (2013.01)

(58) Field of Classification Search

None

See application file for complete search history.

(56) References Cited

U.S. PATENT DOCUMENTS 4,235,877 A 11/1980 Fullerton
4,427,782 A * 1/1984 Caldwell ............. C07K 14/295 435/7.36
4,429,008 A 1/1984 Martin et al.
4,436,727 A 3/1984 Ribi
4,489,710 A 12/1984 Spitler
4,507,234 A 3/1985 Kato et al.
4,569,789 A 2/1986 Blattler et al.
4,603,112 A 7/1986 Paoletti et al.
4,635,014 A 1/1987 Erb et al.
4,638,045 A 1/1987 Kohn et al.
4,671,958 A 6/1987 Rodwell et al.
4,673,562 A 6/1987 Davison et al.
4,699,784 A 10/1987 Shih et al.
4,722,848 A 2/1988 Paoletti et al.
4,735,792 A 4/1988 Srivastava
4,751,180 A 6/1988 Cousens et al.
4,769,330 A 9/1988 Paoletti et al.
4,777,127 A 10/1988 Suni et al.
4,866,034 A 9/1989 Ribi
4,873,088 A 10/1989 Mayhew et al.
4,877,611 A 10/1989 Cantrell
4,897,268 A 1/1990 Tice et al.
4,912,094 A 3/1990 Myers et al.
4,918,164 A 4/1990 Hellstrom et al.
4,935,233 A 6/1990 Bell et al.
4,946,778 A 8/1990 Ladner et al.
5,017,487 A 5/1991 Stunnenberg et al.
5,071,962 A * 12/1991 Morrison ............. C07K 14/295 530/389.5
5,075,109 A 12/1991 Tice et al.
5,075,228 A * 12/1991 Nano .................. C07K 14/295 435/252.33
5,077,044 A 12/1991 Stocker
5,110,587 A 5/1992 Paoletti et al.
5,112,749 A 5/1992 Brey, III et al.
5,174,993 A 12/1992 Paoletti
5,223,424 A 6/1993 Cochran et al.
5,225,336 A 7/1993 Paoletti
5,225,539 A 7/1993 Winter
5,240,703 A 8/1993 Cochran
5,242,829 A 9/1993 Panicali et al.

(Continued)

FOREIGN PATENT DOCUMENTS

EP 0345242 9/1994
EP 1981905 A2 * 10/2008

(Continued)

OTHER PUBLICATIONS

Wehrl et al Molecular Microbiology, 2004, 51/2:319-334.*
Crane et al, PNAS, Feb. 7, 2006, 103/6:1894-1899.*
Eko et al, Vaccine, 2011, 29:3802-3810.*
Kiselev et al, PLoS ONE, Jun. 27, 2007, Issue 6, e568, 8 pages.*
Kiselev et al, PLoS One, Apr. 15, 2009, 4/4:e5191, 14 pages.*
Swanson et al, Infection and Immunity, Jan. 2009, 77/1:508-516.*
Stephens et al, Science 1998, 282:754-759.*
Igietseme et al, Infection and Immunity, 2000, 68/12:6798-6806.*
Bhattarai et al, Biomaterials, 2012, 33:5166-5174.*
Longbottom et al, JMM, 2003, 52:537-540.*
Kari et al, Infection and Immunity p. 2756-2762 Jul. 2014 vol. 82 No. 7.*

(Continued)

*Primary Examiner* — Nita M. Minnifield
(74) *Attorney, Agent, or Firm* — Locke Lord LLP; Nicholas J. DiCeglie, Jr.; Andrew W. Smith

(57) ABSTRACT

Compositions and methods for the treatment of Chlamydial infection are disclosed. The compositions provided include polypeptides that contain at least one antigenic portion of a *Chlamydia* antigen and DNA sequences encoding such polypeptides. Pharmaceutical compositions, vaccines and diagnostic kits are also disclosed.

12 Claims, 6 Drawing Sheets

Specification includes a Sequence Listing.

(56) References Cited

U.S. PATENT DOCUMENTS

| | | | | |
|---|---|---|---|---|
| 5,294,441 | A | 3/1994 | Curtiss, III | |
| 5,294,548 | A | 3/1994 | McLinden et al. | |
| 5,310,668 | A | 5/1994 | Ellis et al. | |
| 5,359,681 | A | 10/1994 | Jorgenson et al. | |
| 5,387,744 | A | 2/1995 | Curtiss, III et al. | |
| 5,389,368 | A | 2/1995 | Curtiss, III | |
| 5,424,065 | A | 6/1995 | Curtiss, III et al. | |
| 5,451,499 | A | 9/1995 | Cochran | |
| 5,453,364 | A | 9/1995 | Paoletti | |
| 5,462,734 | A | 10/1995 | Letchworth, III et al. | |
| 5,470,734 | A | 11/1995 | Sondermeijer et al. | |
| 5,482,713 | A | 1/1996 | Paoletti | |
| 5,518,913 | A | 5/1996 | Massie et al. | |
| 5,585,362 | A | 12/1996 | Wilson et al. | |
| 5,593,972 | A | 1/1997 | Weiner et al. | |
| 5,616,326 | A | 4/1997 | Spibey | |
| 5,698,202 | A | 12/1997 | Ertl et al. | |
| 5,739,118 | A | 4/1998 | Carrano et al. | |
| 5,837,533 | A | 11/1998 | Boutin | |
| 5,869,608 | A * | 2/1999 | Caldwell .............. | C07K 14/295 424/185.1 |
| 5,981,505 | A | 11/1999 | Weiner et al. | |
| 6,384,206 | B1 * | 5/2002 | Caldwell .............. | C07K 14/295 536/23.7 |
| 6,423,835 | B1 * | 7/2002 | Morrison ............. | C07K 14/295 435/252.3 |
| 6,432,916 | B1 * | 8/2002 | Probst .................. | C07K 14/295 424/130.1 |
| 6,448,234 | B1 * | 9/2002 | Fling .................... | C07K 14/295 424/184.1 |
| 6,565,856 | B1 * | 5/2003 | Skeiky ................. | C07K 14/295 424/263.1 |
| 6,919,187 | B2 * | 7/2005 | Bhatia .................. | A61K 39/118 424/190.1 |
| 7,361,353 | B2 * | 4/2008 | Grandi ................. | A61K 39/118 424/190.1 |
| 7,384,638 | B2 | 6/2008 | Bhatia et al. | |
| 7,387,638 | B2 * | 6/2008 | Gonzales ................ | A61F 7/123 606/21 |
| 7,462,357 | B2 * | 12/2008 | Bhatia .................. | C07K 14/295 424/184.1 |
| 7,842,297 | B2 * | 11/2010 | Grandi ................. | A61K 39/118 424/190.1 |
| 8,052,975 | B2 * | 11/2011 | Bhatia .................. | C07K 14/295 424/184.1 |
| 8,263,089 | B2 * | 9/2012 | Bhatia .................. | C07K 14/295 424/184.1 |
| 8,481,057 | B2 * | 7/2013 | Grandi ................. | A61K 39/118 424/192.1 |
| 8,541,007 | B2 * | 9/2013 | Alderson ............. | A61K 39/118 424/263.1 |
| 8,703,153 | B2 * | 4/2014 | Telfer ................. | A61K 39/0275 424/184.1 |
| 9,259,463 | B2 * | 2/2016 | Caldwell .............. | A61K 39/118 |
| 10,258,682 | B2 * | 4/2019 | Caldwell .............. | A61K 39/118 |
| 2002/0146776 | A1 * | 10/2002 | Bhatia .................. | C07K 14/295 435/69.3 |
| 2003/0175700 | A1 * | 9/2003 | Bhatia .................. | C07K 14/295 435/6.15 |
| 2004/0131625 | A1 * | 7/2004 | Berthet ................ | C07K 14/295 424/184.1 |
| 2004/0137007 | A1 * | 7/2004 | Bhatia .................. | C07K 14/295 424/185.1 |
| 2005/0084499 | A1 * | 4/2005 | Bhatia .................. | A61K 39/118 424/190.1 |
| 2005/0232941 | A1 * | 10/2005 | Bhatia .................. | A61K 39/118 424/190.1 |
| 2005/0281847 | A1 * | 12/2005 | Berthet ................ | C07K 14/295 424/263.1 |
| 2006/0034871 | A1 * | 2/2006 | Grandi ................. | A61K 39/118 424/263.1 |
| 2008/0176797 | A1 * | 7/2008 | Bhatia .................. | A61K 39/118 424/190.1 |
| 2009/0022755 | A1 * | 1/2009 | Barth ................... | A61K 39/118 424/190.1 |
| 2009/0047283 | A1 * | 2/2009 | Bhatia .................. | A61K 39/118 514/1.1 |
| 2010/0172927 | A1 * | 7/2010 | Alderson ............. | A61K 39/118 424/190.1 |
| 2010/0255002 | A1 * | 10/2010 | Grandi ................. | A61K 39/118 424/164.1 |
| 2011/0014210 | A1 * | 1/2011 | Caldwell .............. | A61K 39/118 424/164.1 |
| 2011/0300206 | A1 * | 12/2011 | Alderson ............. | A61K 39/118 424/450 |
| 2013/0121915 | A1 * | 5/2013 | Paas ................. | A61K 47/48338 424/9.1 |
| 2013/0171238 | A1 * | 7/2013 | Grandi ................. | A61K 39/118 424/450 |
| 2014/0056967 | A1 * | 2/2014 | Barth ................... | C07K 14/295 424/450 |
| 2017/0021007 | A1 * | 1/2017 | Caldwell .............. | A61K 39/118 |

FOREIGN PATENT DOCUMENTS

| | | | |
|---|---|---|---|
| GB | 2200651 | | 8/1988 |
| WO | WO 1989/001973 | | 3/1989 |
| WO | WO 1990/013678 | | 11/1990 |
| WO | WO 1991/002805 | | 3/1991 |
| WO | WO 1991/018926 | | 12/1991 |
| WO | WO 1994/000153 | | 1/1994 |
| WO | WO 1994/016737 | | 8/1994 |
| WO | WO 1994/020078 | | 9/1994 |
| WO | WO 1994/023701 | | 10/1994 |
| WO | WO 1996/002555 | | 2/1996 |
| WO | WO 1996/006638 | | 3/1996 |
| WO | WO 1996/033739 | | 10/1996 |
| WO | WO 1997/024447 | | 7/1997 |
| WO | WO 1999/033488 | | 7/1999 |
| WO | WO 1999/043839 | | 9/1999 |
| WO | WO200034483 | A2 * | 6/2000 |
| WO | WO 2001/081379 | A2 * | 11/2001 |
| WO | WO 2002/062380 | A2 * | 8/2002 |
| WO | WO-03/041560 | A2 | 5/2003 |
| WO | WO 2003/041560 | A2 * | 5/2003 |
| WO | WO 2003/019762 | A2 * | 6/2003 |
| WO | WO 2005/002619 | A2 * | 1/2005 |
| WO | WO 2006/045308 | * | 5/2006 |
| WO | WO 2006/104890 | A2 * | 10/2006 |
| WO | WO 2007/082105 | A2 * | 7/2007 |
| WO | WO 2007/110700 | A2 * | 10/2007 |
| WO | WO 2008/040757 | A2 * | 4/2008 |
| WO | WO 2009/020553 | A2 * | 2/2009 |
| WO | WO 2009/143413 | A1 * | 11/2009 |
| WO | WO 2010/078027 | * | 7/2010 |
| WO | WO 2010/100632 | A2 * | 9/2010 |
| WO | WO 2011/112670 | A2 * | 9/2011 |
| WO | WO 2011/125015 | A2 * | 10/2011 |

OTHER PUBLICATIONS

Brunham et al, Nature Review/Immunology, Feb. 2005, 5:149-161.*

International Search report issued in corresponding International Patent Application No. PCT/US2007/001213 dated Nov. 15, 2007.

J.H. Carlson et al., "Comparative Genomic Analysis of *Chlamydia trachomatis* Oculotropic and Genitotropic Strains", *Infection and Immunity*, 73(10), pp. 6407-6418 (Oct. 2005).

J.P. Gomes et al., "Polymorphisms in the Nine Polymorphic Membrane Proteins of *Chlamydia trachomatis* across All Serovars: Evidence for Serovar Da Recombination and Correlation with Tissue Tropism", *Journal of Bacteriology*, 188(1), pp. 275-286 (Jan. 2006).

W. Wehrl et al., "From the inside out—processing of the Chlamydial autotransporter PmpD and its role in bacterial adhesion and activation of human host cells", *Molecular Microbiology*, 51(2), pp. 319-334 (2004).

(56) References Cited

OTHER PUBLICATIONS

D.D. Crane et al., "Chlamydia trachomatis polymorphic membrane protein D is a species-common pan-neutralizing antigen", *PNAS*, 103(6), pp. 1894-1899 (Feb. 2006).
H.D. Caldwell et al., "Purification of a Chlamydia Trachomatis-Specific Antigen by Immunoadsorption with Monospecific Antibody", *The Journal of Immunology*, 118(2), pp. 437-441 (Feb. 1977).
H.D. Caldwell et al., "Antigenic Analysis of Chlamydiae by Two-Dimensional Immunoelectrophoresis: I. Antigenic Heterogeneity between C. trachomatis and C. psittaci", *The Journal of Immunology*, 115(4), pp. 963-968 (Oct. 1975).
H.D. Caldwell et al., "Antigenic Analysis of Chlamydiae by Two-Dimensional Immunoelectrophoresis: II. A Trachoma-LGV Specific Antigen" *The Journal of Immunology*, vol. 115, pp. 969-975 (Oct. 1975).
I.R. Henderson et al., "The great escape: structure and function of the autotransporter proteins", *Trends in Microbiology*, 6(9), pp. 370-378 (Sep. 1998).
Altschul, et al., "Basic local alignment search tool", (1990) J. Mol. Biol. 215:403-410.
Anttila, et al. "Serotypes of chlamydia trachomatis and risk for development of cervical squamous cell carcinoma", (2001) JAMA 285, 47-51.
Banchereau and Steinman, "Dendritic cells and the control of immunity", Nature 392:245-251 (1998).
Barron, et al., "A new animal model for the study of chlamydia trachomatis genital infections: infection of mice with the agent of mouse pneumonitis", J Infect Dis 143, 63-66. (1981).
Batteiger, et al., "Partial protection against genital reinfection by immunization of guinea-pigs with isolated outer-membrane proteins of the chlamydial agent of guinea-pig inclusion conjunctivitis", J Gen Microbiol 139, 2965-2972 (1993).
Benvenisty, et al., Direct introduction of genes into rats and expression of genes (transfection) Proc. Natl. Acad. Sci. 83, 9551-9555 (1986).
Bodem, et al., "Regulation of gene expression by human foamy virus and potentials of foamy viral vectors", AlphaMed Press 15, 141-147 (1997).
Broglie, et al., "Light-regulated expression of a pea ribulose-1,5-bisphosphate carboxylase small subunit gene in transformed plant cells", Science 224:838-843 (1984).
Brunham, et al., "Correlation of host immune response with quantitative recovery of chlamydia trachomatis from the human endocervix", Infect Immun 39, 1491-1494 (1983).
Byrne, et al., "Workshop on in vitro neutralization of chlamydia trachomatis: summary of proceedings", J Infect Dis 168, 415-420 (1993).
Caldwell, et al. "Purification of a chlamydia trachomatis-specific antigen by immunoadsorption with monospecific antibody", J Immunol 118, 437-441 (1977).
Caldwell, et al., "Antigenic analysis of chlamydiae by two-dimensional immunoelectrophoresis: II. A Trachoma-LGV-Specific Antigen", J Immunol 115, 969-975 (1975).
Caldwell, et al., "Antigenic analysis of the major outer membrane protein of *Chlamydia* spp.", Infect Immun 35, 1024-1031 (1982).
Caldwell, et al., "Neutralization of chlamydia trachomatis infectivity with antibodies to the major outer membrane protein", Infect linmun 38, 745-754 (1982).
Caldwell, et al., "Purification and partial characterization of the major outer membrane protein of chlamydia trachomatis", Infect Immun 31, 1161-1176 (1981).
Carlson, et al., "Comparative genomic analysis of chlamydia trachomatis oculotropic and genitotropic strains", Infect Immun 73, 6407- 6418 (2005).
Carroll, MW, "Host range and cytopathogenicity of the highly attenuated MVA strain of vaccinia virus: propagation and generation of recombinant viruses in a nonhuman mammalian cell line", Virology. Nov. 24, 1997;238(2):198-211.
Caruthers, et al., "Nucleic acids synthesis: applications to molecular biology and genetic engineering", Nucl. Acids Res. Symp. Ser. 215-223 (1980).
CDC "Sexually Transmitted Disease Surveillance 2001", Atlanta, GA), pp. 1-20 (2002).
Chang, et al.,"Current status of adoptive immunotherapy of cancer", Crit. Rev. Oncol. Hematol, 22(3), 213-228 (1996).
Cheever, et al., "Therapy with Cultured T Cells: Principles Revisited", Immunological Reviews, 157:177-194 (1997).
Cohen, "Naked DNA points way to vaccines", Science 259:1691-1692 (1993).
Cole, et al., "Characterization of the functional specificity of a cloned T-cell receptor heterodimer recognizing the MART-1 melanoma antigen", Cancer Res. 55(4):748-752 (1995).
Cole, et al., "TheEBV-Hybridoma technique and its application to human lung cancer", Monoclonal Antibodies and Cancer Therapy, Alan R. Liss, Inc., pp. 77-96 (1985).
Coombes, et al., "Single dose, polymeric, microparticle-based vaccines: the influence of formulation conditions on the magnitude and duration of the immune response to a protein antigen", Vaccine 14:1429-1438 (1996).
Coruzzi, et al., "Tissue-specific and light-regulated expression of a pea nuclear gene encoding the small subunit of ribulose-1,5-bisphosphate carboxylase", EMBO J. 3:1671-1679 (1984).
Cote, et al., "Generation of human monoclonal antibodies reactive with cellular antigens", Proc. Natl. Acad. Sci USA 80:2026-2030 (1983).
Cotter, et al., "Protective efficacy of major outer membrane protein-specific immunoglobulin A (IgA) and IgG monoclonal antibodies in a murine model of chlamydia trachomatis genital tract infection", Infect Immun. 63, 4704-4714 (1995).
Dayhoff, "A model of evolutionary change in proteins" National Biomedical Research Foundation, Washington, DC vol. 5, Suppl.3, pp. 345-358 (1990) (Atlas of protein sequence and structure, pp. 345-358, 1978).
Engelhard, et al., "The insect tracheal system: a conduit for the systemic spread of Autographa californica M nuclear polyhedrosis virus", (1994) Proc. Natl. Acad. Sci. 91:3224-3227.
Eshhar, Z., "Tumor-specific t-bodies: towards clinical application", Cancer Immunol Immunother 45(3-4):131-136 (1997).
Fisher-Hoch, et al., "Protection of rhesus monkeys from fatal Lassa fever by vaccination with a recombinant vaccinia virus containing the Lassa virus glycoprotein gene", Proc. Natl. Acad. Sci. USA 86:317-321 (1989).
Flexner, et al., "Attenuation and immunogenicity in primates of vaccinia virus recombinants expressing human interleukin-2", Vaccine 8:17-21 (1990).
Garcia, et al., "Nucleotide sequence and expression of the pneumococcal autolysin gene from its own promoter in *Escherichia coli*", Gene; Gene 43:265-292 (1986) was "LYTA".
Gomez-Foix, et al., "Adenovirus-mediated transfer of the muscle glycogen phosphorylase gene into hepatocytes confers altered regulation of glycogen metabolism", Journal biological chemistry 267;25129-25134(1992).
Graham, et al., "Manipulation of adenovirus vectors", Methods Molecular Biology, 7:109-128 (1991).
Grayston, et al., "Trachoma and Related Disorders Caused by Chlamydial Agents", ed. Nichols, R. L. (Excerpta Medica, Boston, Massachusetts), pp. 377-385 (1971).
Grimwood, et al., Computational analysis of the polymorphic membrane protein superfamily of chlamydia trachomatis and chlamydia pneumoniae:, Microb Comp Genomics 4, 187-201 (1999).
Gustafsson, et al., "SPAM-8, a mouse-human heteromyeloma fusion partner in the production of human monoclonal antibodies. Establishment of a human monoclonal antibody against cytomegalovirus", Hum. Antibodies Hybridomas, vol. 2, 26-32 (1991).
Guzman, et al., "Efficient and selective adenovirus-mediated gene transfer into vascular neointima", Circulation 88:2838-2848 (1993).
Guzman, et al., "Efficient Gene Transfer into Myocardium by direct injection of adenovirus vectors", Cir. Res. 73:1202-1207 (1993).
Hein, "Unified approach to alignment and phylogenes" methods in enzymology vol. 183, pp. 626-645, Academic Press, Inc., San Diego, CA (1990).

(56) References Cited

OTHER PUBLICATIONS

Heller, et al., "Discovery and analysis of inflammatory disease-related genes using cDNA microarrays", Proc. Natl. Acad. Sci. USA 94:2150-2155 (1977).
Henderson, et al., "Polymorphic proteins of *Chlamydia* spp.—autotransporters beyond the proteobacteria", Trends Microbial 9, 573-579 (2001).
Henderson, et al., "The great escape: structure and function of the autotransporter proteins", Trends Microbiol 6, 370-378 (1998).
Henikoff, et al., "Amino acid substitution matrices from protein blocks", Proc. Natl. Acad. Sci USA 89:10915-10919 (1992).
Hermonat, et al., "Use of adeno-associated virus as a mammalian DNA cloning vector: transduction of neomycin resistance into mammalian tissue culture cells", Proc.Natl. Acad. Sci. 81:6466-6470 (1984).
Higgins, et al., "Fast and sensitive multiple sequence alignments on a microcomputer", CABIOS 5:151-153 (1989).
Horn, et al, "Synthesis of oligonucleotides on cellulose. Part II: design and synthetic strategy to the synthesis of 22 oligodeoxynucleotides coding for Gastric Inhibitory Polypeptide (GIP)", Nucl. Acids Res. Symp. Ser 225-232 (1980).
Hobbs, et al., McGraw Hill Yearbook of Science and Technology, 1992, pp. 191-196.
Huse, et al.,"Generation of a large combinatorial library of the immunoglobulin repertoire in phage lambda", Science 246:1275-1281 (1989).
Hwu, et al., "In Vivo Antitumor activity of T cells redirected with chimeric antibody/T-cell receptor genes", Cancer Res. 55(15):3369-3373 (1995).
Igietseme, et al., "Chlamydia vaccines strategies and status", (2002) Biodrugs 16, 19-35.
Jones, et al., "Baculovirus vectors for expression in insect cells", Current opinion in biotechnology 7:512-516 (1996).
Jones, et al., "Isolation of deletion and substitution mutants of adenovirus type 5", Cell 12:181-188 (1978).
Kalman, et al., "Comparative genomes of chlamydia pneumoniae and C. trachomatis", Nat Genet 21, 385-389 (1999).
Kass-Eisler, et al., "Quantitative determination of adenovirus-mediated gene delivery to rat cardiac myocytes in vitro and in vivo", Proc. Natl. Acad. Sci. USA 90:11498-11502 (1993).
Katocs, et al., "Biological Testing", Chapter 27 In: Remington's Pharmaceutical Sciences, 18th, Gennaro, ed., Mack Publishing Co., Easton, PA, 484-494 (1990).
Köhler, et al., "Continuous cultures of fused cells secreting antibody of predefined specificity", Nature 256:495-497 (1975).
Köhler, et al., "Derivation of specific antibody-producing tissue culture and tumor lines by cell fusion", Eur. J. Immunol 6:511-519 (1976).
Kolls, et al.,"Prolonged and effective blockade of tumor necrosis factor activity through adenorvirus-mediated gene transfer", Proc. Natl. Acad. Sci. USA 91:215-219 (1994).
Le Gal La Salle, et al., "An adenovirus vector for gene transfer into neurons and glia in the brain", Science 259:988-990 (1993).
Logan, et al., "Adenovirus tripartite leader sequence enhances translation of mRNAs late after injection", Proc. Natl. Acad, Sci. 81:3655-3659 (1984).
Mahvi, et al., "DNA cancer vaccines: a gene gun approach", Immunology and cell Biology 75:456-460 (1997).
Maratea, et al., "Deletion and fusion analysis of the phage oX174 lysis gene E", Gene 40:39-46 (1985).
McLaughlin, et al., "Adeno-associated virus general transduction vectors: analysis of proviral structures", Journal of Virology 62:1963-1973 (1988).
Merrifield,R.B., "Solid phase peptide synthesis. I. The synthesis of a tetrapeptide", J. Am. Chem Soc. 85:2149-2154 (1963).
Moore, et al., "Fc receptor regulation of protective immunity against chlamydia trachomatis", Immunology 105, 213-221 (2002).
Morrison, et al., "Chimeric human antibody molecules: mouse antigen-binding domains with human constant region domains", Proc. Natl. Acad. Sci USA 81:6851-6855 (1984).
Morrison, et al., "Immunity to murine chlamydial genital infection", Infect Immun 70, 2741-2751 (2002).
Mosmann, et al., "TH1 and TH2 cells: different patterns of lymphokine secretion lead to different functional properties", Ann. Rev. Immunol. 7:145-173 (1989).
Moss, et al. "Vaccinia virus expression vectors[a]", Ann. NY Acad. Sci. 569:86-103 (1989).
Murphy, et al., "Genetic construction, expression, and melanoma-selective cytotoxicity of a diphtheria toxin-related a-melanocyte-stimulating hormone fusion protein", Proc. Nat. Acad. Sci. USA 83:8258-8262 (1986).
Myers, et al., "Optimal alignments in linear space", CABIOS 4:11-17 (1988).
Needleman, et al., "A general method applicable to the search for similarities in the amino acid sequence of two proteins", J. Mol. Biol. 48:443 (1970).
Neuberger, et al., "Recombinant antibodies possessing novel effector functions", Nature 312:604-608 (1984).
Nies, et al., "Principles of therapeutics", Chapter 3 In: Goodman & Gilman's The Pharmacological Basis of Therapeutics, 9th Ed. 43-62 (1996).
O'Brien, et al., "Tissue-specific accumulation of latency-associated transcripts in herpes virus-infected rabbits", (1998) Invest Ophthalmol Vis Sci 39, 1847-1853.
Pal, et al., "Immunization with an acellular vaccine consisting of the outer membrane complex of chlamydia trachomatis induces protection against a genital challenge",(1997) Infect Immun 65, 3361-3369.
Pal, et al., "Vaccination of mice with DNA plasmids coding for the chlamydia trachomatis major outer membrane protein elicits an immune response but fails to protect against a genital challenge", (1999) Vaccine 17, 459-465.
Paul, "Immunogenicity and antigen structure", Fundamental Immunology, 3rd ed., 243:247 (Raven Press, 1993).
Pearson and Lipman, "Improved tools for biological sequence comparison", (1988) Proc. Natl. Acad. Sci. USA 85:2444-2448.
Plummer, et al., "Cofactors in male-female transmission of human immunodeficiency virus type 1", J Infect Dis 163:233-239 (1991).
Possee, R.D., "Baculoviruses as expression vectors", Current Opinion Biotechnology 8:569:572 (1997).
Racher, et al. "Culture of 293 cells in different cu lture systems: cell growth and recombinant adenovirus production", Biltechnology techniques, 9:169-174 (1995).
Read, et al., "Genome sequence of chlamydia trachomatis MoPn and chlamydia pneumoniae AR38", (2000) Nucleic Acids Res 28, 1397-1406.
Read, et al., "Genome sequence of chlamydophila caviae (Chlamydia psittaci GPIC): examining the role of niche-specific genes in the evolution of the chlamydiaceae", (2003) Nucleic Acids Res 31, 2134-2147.
Resnikoff, et al., "Global data on visual impairment in the year 2002", (2004) Bull World Health Organ 82, 844-851.
Roberge, et al., "A strategy for a convergent synthesis of n-linked glycopeptides on a solid support", (1995) Science 269:202-204.
Robinson, D.F., "Comparison of labeled trees with valency three", Comb. Theor 11:105-119 (1971).
Rolland, A.P., "From genes to gene medicines: recent advances in nonviral gene delivery", Crit. Rev. Therap. Drug Carrier Systems 15:143-198 (1998).
Rosenfield, et al., "Adenovirus-mediated transfer of a recombinant α1-antitrypsin gene to the lung epithelium in vitro", Science 252:431-434 (1991).
Sacket, et al., "Clinical Epidemiology: A Basic Science for Clinical Medicine", Little Brown and Co, pp. 106-107 (1985).
Saitou, et al., "The neighbor-joining method: a new method for reconstructing phylogenetic trees", Mol. Biol. Evol. 4:406-425 (1987).
Schena, et al., "Parallel human genome analysis: microarray-based expression monitoring of 1000 genes", Proc. Nat. Acad. Sci. USA 93:10614-10619 (1996).
Scidmore, et al., "Vesicular interactions of the chlamydia trachomatis inclusion are determined by chlamydial early protein synthesis rather than route of entry", (1996) Infect Immun 64, 5366-5372.

(56) References Cited

OTHER PUBLICATIONS

Smith, et al., "Comparison of biosequences", Add. APL. Math 2:482-489 (1981).
Stephens, et al. "Genome Sequence of an obligate intracellular pathogen of humans: chlamydia trachomatis", (1998) Science 282, 754-759.
Stoute, et al., "A preliminary evaluation of a recombinant circumsporozoite protein vaccine against plasmodium falciparum malaria", New Engl. J. Med, 336:86-91 (1997).
Strattford-Perricaudet, et al., "Evaluation of the transfer and expression in mice of an enzyme-encoding gene using a human adenovirus vector", Human Gene Therapy 1:241-256 (1990).
Su, et al., "Chlamydia trachomatis genital tract infection of antibody-deficient gene knockout mice", (1997) Infect Immun 65, 1993-1999.
Su, et al., "Chlamydia trachomatis-host cell interactions: role of the chlamydial major outer membrane protein as an adhesion", (1990) Infect Immun 58, 1017-1025.
Su, et al., "Expression of FcyRIII on HeLa 229 cells: possible effect on in vitro neutralization of chlamydia trachomatis", (1991) Infect Immun 59, 3811-3814.
Su, et al., "In vitro neutralization of chlamydia trachomatis by monovalent fab antibody specific to the major outer membrane protein", (1991) Infect Immun 59, 2843-2845.
Su, et al., "Protective efficacy of a parenterally administered MOMP-derived synthetic oligopeptide vaccine in a murine model of chlamydia trachomatis genital tract infection: serum neutralizing IgG antibodies do not protect against chlamydial genital tract infection", Vaccine 13, 1023-1032 (1995).
Takamatsu, "Expression of bacterial chloramphenicol acetyltransferase gene in tobacco plants mediated by TMV-RNA",(1987) EMBO J. 6:307-311.
Timmerman, et al., "Dendritic cell vaccines for cancer immunotherapy", Rev. Med. 50:507-529 (1999).
Tomanin, et al., "Development and characterization of a binary gene expression system based on bacteriophage T7 components in adenovirus vectors", Gene 193:129-140 (1997).
Tubulekas, et al., "Alphavirus expression vectors and their use as recombinant vaccines: a minireview", Gene 190:191-105 (1997).
Ulmer, et al., "Protective $CD4^+$ and $CD8^+$ T Cells against influenza virus induced by vaccination with nucleoprotein DNA", J. Virology 72:5648-5653 (1998).
Van Heeke, et al., "Expression of human asparagine synthetase in *Escherichia coli*", (1989) J. Biol. Chem. 264:5503-5509.
Wehrl, et al., "From the inside out—processing of the chlamydial autotransporter PmpD and its role in bacterial adhesion and activation of human host cells", (2004) Mo/Microbiol 51, 319-334.
Weström, et al., "Pelvic Inflammatory Disease and Fertility", Sex. Transm. Dis. 19, 185-192 (1992).
Whitcher, et al., "Corneal blindness: a global perspective", (2001) Bull World Health Organ 79, 214-221.
Who, "Global Prevalence and Incidence of Selected Curable Sexually Transmitted Infections: Overview and Estimates", Geneva, pp. 1-43 (2001).
Wilbur, et al., "Rapid similarity searches of nucleic acid and protein data banks", Proc. Natl. Acad., Sci USA 80:726-730 (1983).
Winter, et al., "6 the expression of heat shock protein and cognate genes during plant development", Results Probl. Cell Differ. 17:85-105 (1991).
Zhang, et al., "DNA vaccination with the major outer-membrane protein gene induces acquired immunity to chlamydia trachomatis (mouse pneumonitis) infection", J Infect Dis 176, 1035-1040 (1997).
Zhang, et al., "Protective monoclonal antibodies recognize epitopes located on the major outer membrane protein of chlamydia trachomatis", J Immunol 138, 575-581 (1987).
Altschul, et al., "Gapped BLAST and PSI-BLAST: a new generation of protein database search programs", (1997) Nucl. Acids Res. 25:3389-3402.
Berkner, "Development of adenovirus vectors for the expression of heterologous genes", Biotechniques 6:616-627 (1988).
Carroll MW, "Poxviruses as expression vectors", Curr Opin Biotechnol., Oct. 1997;8(5):573-577.
Coffin, et al. Molecular mechanisms of nucleic acid integration. J Med Virol. May 1990;31(1):43-49.
Couch, et al., immunization with types 4 and 7 adenovirus by selective infection of the intestinal tract. Am Rev Respir Dis. Sep. 1963;88:SUPPL 394-403.
Coupar, et al., A general method for the construction of recombinant vaccinia viruses expressing multiple foreign genes. Gene. Aug. 15, 1988;68(1):1-10.
Dubensky, et al., Direct transfection of viral and plasmid DNA into the liver or spleen of mice. Proc Natl Acad Sci U S A. Dec. 1984;81(23):7529-7533.
Friedmann, Progress toward human gene therapy. Science. Jun. 16, 1989;244(4910):1275-1281.
Ghosh-Choudhury, et al., Protein IX, a minor component of the human adenovirus capsid, is essential for the packaging of full length genomes. EMBO J. Jun. 1987;6(6):1733-1739.
Graham and Prevec, Adenovirus-based expression vectors and recombinant vaccines. Biotechnology. 1992;20:363-390.
Graham, F., Undercurrents, Adenoviruses as expression vectors and recombinant vaccines. Elsevier Science Publishers Ltd (UK) 8:85-86 (1990).
Grunhaus and Horwitz, Association of vaccinia virus-expressed adenovirus E3-19K glycoprotein with class I MHC and its effects on virulence in a murine pneumonia model. Virology. May 1, 1994;200(2):535-546.
Harrison, et al., Host-range mutants of adenovirus type 5 defective for growth in HeLa cells. Virology. Mar. 1977;77(1):319-329.
Herz and Gerard, Adenovirus-mediated transfer of low density lipoprotein receptor gene acutely accelerates cholesterol clearance in normal mice. Proc Natl Acad Sci U S A. Apr. 1, 1993;90(7):2812-2816.
Horwich, et al., Synthesis of hepadnavirus particles that contain replication-defective duck hepatitis B virus genomes in cultured HuH7 cells. J Virol. Feb. 1990;64(2):642-650.
Huang, Sindbis virus vectors for expression in animal cells. Curr Opin Biotechnol. Oct. 1996;7(5):531-535.
Jane, G., "Phylogenetic Analysis of a Multigene Family Conserved Between Chlamydia Trachomatis and Chlamydia Pneumoniae", (1998) in Proceedings of the ninth international symposium on Human Chlamydial infection, eds. (International Chlamydia Symposium, San Francisco), pp. 263-266.
Khatri, et al., Gene expression by atypical recombinant ovine adenovirus vectors during abortive infection of human and animal cells in vitro. Virology. Dec. 8, 1997;239(1):226-237.
Kim, et al., Construction of retroviral vectors with improved safety, gene expression, and versatility. J Virol. Feb. 1998;72(2):994-1004.
Klein, et al., Human neonatal lymphocytes immortalized after microinjection of Epstein-Barr virus DNA. J Virol. May 1987;61(5):1552-1558.
Koh, et al., Baculoviral transfer vectors for expression of FLAG fusion proteins in insect cells. Biotechniques. Oct. 1997;23(4):622-627.
Levrero, et al. Defective and nondefective adenovirus vectors for expressing foreign genes in vitro and in vivo. Gene. May 30, 1991;101(2):195-202.
Lindquist, et al, Lindquist, E. & Stephens, R., Transcriptional Activity of a Sequence Variable Protein Family in Chlamydia Trachomatis, (1998) in *Proceedings of the ninth international symposium on Human Chlamydial infection*, eds. (International Chlamydia Symposium, San Francisco), pp. 259-262.
Lundstrom, Alphaviruses as expression vectors. Curr Opin Biotechnol. Oct. 1997;8(5):578-582.
Mann, et al., Construction of a retrovirus packaging mutant and its use to produce helper-free defective retrovirus. Cell. May 1983;33(1):153-159.
Mulligan, The basic science of gene therapy. Science. May 14, 1993;260(5110):926-932.
Murakami, et al., High-level expression of exogenous genes by replication-competent retrovirus vectors with an internal ribosomal entry site. Gene. Nov. 20, 1997;202(1-2):23-29.

(56) References Cited

OTHER PUBLICATIONS

O'Reilly, Use of baculovirus expression vectors. Methods Mol Biol. 1997;62:235-246.

Oertli, et al., Artificial antigen-presenting cells engineered by recombinant vaccinia viruses expressing antigen, MHC class II, and costimulatory molecules elicit proliferation of CD4+ lymphocytes in vitro. Clin Exp Immunol. Oct. 1997; 110(1): 144-149 doi: 10.1046/j.1365-2249.1997.5061405.x.

Ortega, et al., "Single-step purification on deae-sephacel of recombinant polypeptides produced in *Escherichia coli*", Bio/technology 10:795-798 (1992).

Pal, et al., "Vaccination with the Chlamydia Trachomatis (CT) major ourter membrane protein (MOMP) can induce protection against a genital challenge", Proceedings Fifth Meeting of the European Society for Chlamydia Research, ed. Deak, J. (University of Szeged, Budapest, Hungary), pp. 394 (2004).

Paskind, et al., Dependence of moloney murine leukemia virus production on cell growth. Virology. Sep. 1975;67(1):242-248.

Rosenfeld, et al., In vivo transfer of the human cystic fibrosis transmembrane conductance regulator gene to the airway epithelium. Cell. Jan. 10, 1992;68(1):143-155.

Takeda, et al., "Construction of chimaeric processed immunoglobulin genes containing mouse variable and human constant region sequences", Nature 314:452-454 (1985).

Temin, Retroviruses and evolution. Cell Biophys. Dec. 1986;9(1-2):9-16.

Top, et al. Immunization with live types 7 and 4 adenovirus vaccines. II. Antibody response and protective effect against acute respiratory disease due to adenovirus type 7. J Infect Dis. Aug. 1971;124(2):155-160.

Top, et al., Immunization with live types 7 and 4 adenovirus vaccines. I. Safety, infectivity, antigenicity, and potency of adenovirus type 7 vaccine in humans. J Infect Dis. Aug. 1971;124(2):148-154.

Wang, et al, Expression of chemokine receptors in insect cells using baculovirus vectors. Methods Enzymol. 1997;288:38-55.

Wu, et al., Novel green fluorescent protein (GFP) baculovirus expression vectors. Gene. Apr. 29, 1997;190(1):157-162.

Zelenin, et al., High-velocity mechanical DNA transfer of the chloramphenicolacetyl transferase gene into rodent liver, kidney and mammary gland cells in organ explants and in vivo. FEBS Lett. Mar. 11, 1991;280(1):94-96.

Zitvogel, et al., Eradication of established murine tumors using a novel cell-free vaccine: dendritic cell-derived exosomes, Nature Med. 4:594-600 (1998).

* cited by examiner

CHLAMYDIA VACCINE

The present application is a divisional of U.S. application Ser. No. 12/087,952, filed Oct. 1, 2010, which issued as U.S. Pat. No. 9,259,463 on Feb. 16, 2016, which is the U.S. National Phase entry, pursuant to 35 U.S.C. § 371, of PCT International Application No. PCT/US2007/001213, filed Jan. 16, 2007, which claims the benefit of U.S. provisional application No. 60/760,970, filed Jan. 16, 2006. The entire contents of the aforementioned patent applications are hereby incorporated herein by reference.

GOVERNMENT SUPPORT

Research supporting this application was carried out by the United States of America as represented by the Secretary, Department of Health and Human Services.

SEQUENCE LISTING

The instant application contains a Sequence Listing containing sequences identified as SEQ ID NOs: 1 to 12.

BACKGROUND

Human infections caused by the obligate intracellular pathogen *Chlamydia trachomatis* have a marked impact on human health. *C. trachomatis* serovariants are the leading cause of bacterial sexually transmitted disease and infectious preventable blindness. Despite decades of effort, there is no practical vaccine against *C. trachomatis* diseases.

*C. trachomatis* is an obligate intracellular bacterial pathogen that colonizes and infects oculogenital mucosal surfaces. The organism exists as multiple serovariants that infect millions of people worldwide. Ocular infections cause trachoma, a chronic follicular conjunctivitis that results in scarring and blindness. WHO estimates that 300-500 million people are afflicted by trachoma (1), making it the most prevalent form of infectious preventable blindness (2). Urogenital infections are the leading cause of bacterial sexually transmitted disease (STD) in both industrialized and developing nations (3). Moreover, STD are risk factors for infertility (4), the transmission of HIV (5) and human papilloma virus induced cervical neoplasia (6). Control of *C. trachomatis* infections is an important public health goal. However, aggressive measures aimed at managing these infections have not altered incidence or disease severity (7). Thus, there is a need in the art for effective control of chlamydial diseases (8).

SUMMARY

The present invention provides compositions and methods for the diagnosis and therapy of *Chlamydia* infection. In one aspect, the present invention provides polypeptides comprising an immunogenic portion of a *Chlamydia* antigen, or a variant of such an antigen. Certain portions and other variants are immunogenic, such that the ability of the variant to react with antigen-specific antisera is not substantially diminished. Within certain embodiments, the polypeptide comprises an amino acid sequence encoded by a polynucleotide sequence selected from one or more of (a) a sequence of SEQ ID NOs: 1-3 or 10-12, (b) the complements of said sequences; (c) variants of SEQ ID NOs: 1-12, e.g., sequences of about 80-99% sequence identity, and (d) sequences that hybridize to a sequence of (a), (b), or (c) under moderately stringent conditions. In specific embodiments, the polypeptides of the present invention comprise at least a portion of a Chlamydial protein that includes an amino acid sequence selected from the group consisting of sequences recited in SEQ ID NOs: 4-9 and variants thereof.

In one aspect, polynucleotide sequences encoding the above polypeptides, recombinant expression vectors comprising one or more of these polynucleotide sequences and host cells transformed or transfected with such expression vectors are also provided.

In another aspect, the present invention provides fusion proteins comprising an inventive polypeptide, or, alternatively, an inventive polypeptide and a known *Chlamydia* antigen, as well as polynucleotides encoding such fusion proteins, in combination with a physiologically acceptable carrier or immunostimulant for use as pharmaceutical compositions and vaccines thereof.

The present invention further provides pharmaceutical compositions that comprise: (a) an antibody, both polyclonal and monoclonal, or antigen-binding fragment thereof that specifically binds to a Chlamydial protein; and (b) a physiologically acceptable carrier. Within other aspects, the present invention provides pharmaceutical compositions that comprise one or more *Chlamydia* polypeptides disclosed herein, for example, a polypeptide of SEQ ID NOs: 4-9, or a polynucleotide molecule encoding such a polypeptide, such as a polynucleotide sequence of SEQ ID NOs: 1-3 or 10-12, and a physiologically acceptable carrier. The invention also provides compositions for prophylactic and therapeutic purposes comprising one or more of the disclosed polynucleotides and/or polypeptides and an immunostimulant, e.g., an adjuvant.

In yet another aspect, methods are provided for stimulating an immune response in a patient, e.g., for inducing protective immunity in a patient, comprising administering to a patient an effective amount of one or more of the above pharmaceutical compositions or vaccines.

The present invention relates to vaccine compositions that comprise an immunologically effective amount of PmpD protein from *C. trachomatis* and a pharmaceutically acceptable carrier. According to some embodiments of the present invention, the vaccine composition comprises an immunologically effective amount of an immunogenic fragment of PmpD protein from *C. trachomatis* and a pharmaceutically acceptable carrier.

The present invention relates, to methods of immunizing individuals against *C. trachomatis*. The immune responses generated may be prophylactic or therapeutic. The methods comprise the steps of administering to the individual an immunologically effective amount of PmpD protein, or immunogenic fragment thereof, from *C. trachomatis*, or a nucleic acid molecule that encodes PmpD protein, or an immunogenic fragment thereof, from *C. trachomatis*. The present invention relates to methods of identifying individuals exposed to PmpD protein from *C. trachomatis* by detecting the presence of PmpD protein from *C. trachomatis* in a sample using antibodies which specifically bind to PmpD protein from *C. trachomatis*. The antibodies are preferably monoclonal antibodies. Quantification of the amount of PmpD protein from *C. trachomatis* present in a sample of an individual may be used in determining the prognosis of an infected individual. In one aspect, antibodies to PmpD are used to differentiate between *C. trachomatis* and other *Chlamydia* bacteria. This may be done by testing sample from a subject or from a cell culture for presence of PmpD with antibodies to PmpD.

In yet a further aspect, methods for the treatment of *Chlamydia* infection in a patient are provided, the methods comprising obtaining peripheral blood mononuclear cells (PBMC) from the patient, incubating the PBMC with a polypeptide of the present invention (or a polynucleotide that encodes such a polypeptide) to provide incubated T cells and administering the incubated T cells to the patient. The present invention additionally provides methods for the treatment of *Chlamydia* infection that comprise incubating antigen presenting cells with a polypeptide of the present invention (or a polynucleotide that encodes such a polypeptide) to provide incubated antigen presenting cells and administering the incubated antigen presenting cells to the patient. Proliferated cells may, but need not, be cloned prior to administration to the patient. In certain embodiments, the antigen presenting cells are selected from the group consisting of dendritic cells, macrophages, monocytes, B-cells, and fibroblasts. Compositions for the treatment of *Chlamydia* infection comprising T cells or antigen presenting cells that have been incubated with a polypeptide or polynucleotide of the present invention are also provided. Within related aspects, vaccines are provided that comprise: (a) an antigen presenting cell that expresses a polypeptide as described above and (b) an immunostimulant.

The present invention further provides, within other aspects, methods for removing Chlamydial-infected cells from a biological sample, comprising contacting a biological sample with T cells that specifically react with a Chlamydial protein, wherein the step of contacting is performed under conditions and for a time sufficient to permit the removal of cells expressing the protein from the sample.

Within related aspects, methods are provided for inhibiting the development of Chlamydial infection in a patient, comprising administering to a patient a biological sample treated as described above. In further aspects of the subject invention, methods and diagnostic kits are provided for detecting *Chlamydia* infection in a patient. In one embodiment, the method comprises: (a) contacting a biological sample with at least one of the polypeptides or fusion proteins disclosed herein; and (b) detecting in the sample the presence of binding agents that bind to the polypeptide or fusion protein, thereby detecting *Chlamydia* infection in the biological sample. Suitable biological samples include whole blood, sputum, serum, plasma, saliva, cerebrospinal fluid and urine. In one embodiment, the diagnostic kits comprise one or more of the polypeptides or fusion proteins disclosed herein in combination with a detection reagent. In yet another embodiment, the diagnostic kits comprise either a monoclonal antibody or a polyclonal antibody that binds with a polypeptide of the present invention.

The present invention relates to kits for identifying individuals exposed to *C. trachomatis* and reagents used in such kits. The kits comprise a first container which contains antibodies which specifically bind to PmpD protein from *C. trachomatis* and a second container which contains PmpD protein from *C. Trachomatis*. The antibodies are preferably monoclonal antibodies. The kits may be adapted for quantifying of the amount of PmpD protein from *C. trachomatis* present in a sample of an individual. Such information may be used in determining the prognosis of an infected individual.

The present invention relates to methods of identifying individuals exposed to *C. trachomatis* by detecting the presence of antibodies against PmpD protein from *C. trachomatis* in a sample using PmpD protein from *C. trachomatis*. Quantification of the amount of anti-PmpD protein from *C. trachomatis* antibodies present in a sample of an individual may be used in determining the prognosis of an infected individual.

The present invention relates to kits for identifying individuals exposed to *C. trachomatis* and reagents used therein. The kits comprise a first container which contains antibodies which were produced in response to exposure to PmpD protein from *C. trachomatis* and a second container which contains PmpD protein from *C. trachomatis*. The kits may be adapted for quantifying the amount of anti-PmpD protein from *C. trachomatis* antibodies present in a sample of an individual. Such information may be used in determining the prognosis of an infected individual.

In one aspect, provided are methods for stimulating an immune response to one or more of a *Chlamydia* bacterium serovariant in a subject, comprising administering to a subject a chlamydial polymorphic membrane protein D polypeptide in an amount sufficient to elicit production of antibodies.

In one embodiment, the chlamydial polymorphic membrane protein D polypeptide comprises one or more of a polymorphic membrane protein D polypeptide from a *Chlamydia trachomatis* serovariant.

In another embodiment, the chlamydial polymorphic membrane protein D polypeptide is provided in a recombinant microorganism.

In one embodiment, the recombinant microorganism is a recombinant virus comprising a chlamydial polymorphic membrane protein D polypeptide-encoding polynucleotide for expression in the subject.

In another embodiment, the administering comprises one or more of subcutaneous, intramuscular, intradermal, or intravenous.

In one embodiment, the antibodies are capable of neutralizing at least two serovariants of *Chlamydia.*

In one embodiment, the methods may further comprise providing a polymorphic membrane protein D polypeptide.

In one aspect, provided are methods of treating a *chlamydia* related disorder or condition in a subject comprising administering a polypeptide comprising one or more of 1) the amino acid sequence of SEQ ID NOs: 4-6; or 2) the amino acid sequence of SEQ ID NOs: 7-9.

In one embodiment, the methods may further comprise providing the polypeptide.

In one embodiment, the *chlamydia* related disorder or condition is an one or more of a sexually transmitted disease or trachoma.

In one aspect, provided are methods of treating an *chlamydia* related disorder or condition in a subject comprising: administering a nucleic acid construct comprising one or more of 1) the nucleotide sequence of SEQ ID NOs: 1-3; 2) the nucleotide sequence of SEQ ID NOs: 10-12; or 3) a nucleic acid molecule encoding a polypeptide comprising the amino acid SEQ ID NOs: 4-6 or 7-9 or fragments or variants thereof.

In one embodiment, the methods may further comprise providing the nucleic acid.

In one embodiment, the nucleic acid is contained in a vector.

In one embodiment, the methods may further comprise determining a polymorphic membrane protein D polypeptide antibody titer after administering the nucleic acid.

In one embodiment, the *Chlamydia* related disorder or condition is an one or more of a sexually transmitted disease or trachoma.

In one aspect, provided are methods of treating an individual exposed to a *Chlamydia* bacteria comprising administering a therapeutically effective amount of a polymorphic membrane protein D or a nucleic acid encoding polymorphic membrane protein D, or a immunogenic fragments thereof, from a *Chlamydia* bacteria.

In one aspect, provided are methods of protecting a subject from *Chlamydia* bacteria infection comprising administering a prophylactically effective amount of polymorphic membrane protein D or a nucleic acid encoding polymorphic membrane protein D, or immunogenic fragments thereof, from a *Chlamydia* bacteria.

In another embodiment, the *Chlamydia* bacteria is one or more of *Chlamydia trachomatis* serovariant.

In one embodiment, the serovariant is one or more of B complex (B, Ba, D, E, L2, L1), C complex (A, C, H, I, J), or Intermediate (F, G, K, L3).

In one aspect, provided are methods of treating a subject infected with one or more *Chlamydia* bacteria comprising administering a therapeutically effective amount of an antibody or binding portion thereof capable of binding to one or more of a *Chlamydia* polymorphic membrane protein D or fragment or variant thereof.

In another embodiment, the administering comprises one or more of oral, intradermal, intramuscular, intraperitoneal, intravenous, subcutaneous, or intranasal.

In one embodiment, the antibody is one or more of a monoclonal or polyclonal.

In another embodiment, a binding portion comprise one or more of a Fab fragment, a $F(ab')_2$ fragment, or a Fv fragment.

In one aspect, provided are methods for the treatment of a *Chlamydia* infection in a subject, comprising (a) incubating CD4+ and/or CD8+ T cells isolated from a patient with one or more of (i) a polypeptide comprising SEQ ID NOs:4-6 or 7-9; (ii) a polynucleotide comprising SEQ ID NOs:1-3 or 10-12; (iii) an antigen presenting cell that expresses a polypeptide sequence set forth in any one of SEQ ID NOs: 4-9; such that the T cells proliferate; and (b) administering to the patient a therapeutically effective amount of the proliferated T cells.

In one aspect, provided are vaccines for preventing *Chlamydia trachomatis* infection and disease in a subject comprising an isolated polypeptide comprising one or more of 1) an amino acid sequence of SEQ ID NOs: 4-6; or 2) an amino acid sequence of SEQ ID NOs: 7-9, or fragments or variants thereof.

In one embodiment, the polypeptide is purified:

In one aspect, provided are methods of vaccinating a subject against infection by a *Chlamydia* bacteria comprising administering a therapeutically effective amount of the vaccine according to one of the embodiments or aspects described herein.

In one embodiment, the administering is oral, intradermal, intramuscular, intraperitoneal, intravenous, subcutaneous, or intranasal.

In one embodiment, the methods may further comprise administering a second therapeutically effective amount of the vaccine according to an aspect or embodiment described herein to a subject.

In one aspect, provided are vaccines comprising an immunologically effective amount of a *Chlamydia* polymorphic membrane protein D, or an immunogenic fragment thereof and a pharmaceutically acceptable carrier.

In one embodiment, the *Chlamydia* is *Chlamydia trachomatis.*

In one aspect, provided are expression vectors comprising a one or more of the nucleotide sequence of SEQ ID NOs: 1-3, the nucleotide sequence of SEQ ID NOs: 10-12, or a nucleic acid molecule encoding a polypeptide comprising the amino acid SEQ ID NOs: 4-9 operably linked to an expression control sequence.

In one aspect, provided are host cells transformed or transfected with an expression vector according to an aspect or embodiment described herein.

In one aspect, provided are isolated antibodies, or antigen-binding fragments thereof, that specifically binds to a polypeptide of one or more of SEQ ID NOs: 4-9.

In one aspect, provided are diagnostic kits comprising at least one antibody aspect or embodiment described herein and a detection reagent, wherein the detection reagent comprises a reporter group.

In one aspect, provided are kits comprising an immunologically effective amount of a *Chlamydia* polymorphic membrane protein D, or an immunogenic fragment thereof, a pharmaceutically acceptable carrier, and instructions for use.

In one aspect, provided are pan neutralizing antigens comprising a *Chlamydia trachomatis* polymorphic membrane protein D polypeptide or a fragment or variant thereof.

As described herein, unless otherwise indicated, methods of virology, immunology, microbiology, molecular biology and recombinant DNA techniques within the skill of the art. Such techniques are explained fully in the literature. See, e.g., Sambrook et al., eds., Molecular Cloning: A Laboratory Manual (2' ed.) Cold Spring Harbor Laboratory Press, Cold Spring Harbor, N.Y. (1989); Ausubel et al., eds., Current Protocols in Molecular Biology, John Wiley & Sons, New York, N.Y. (2000); Glover, ed., DNA Cloning: A Practical Approach, Vols. I & II; Colowick & Kaplan, eds., Methods in Enzymology, Academic Press; Weir & Blackwell, eds., Handbook of Experimental Immunology, Vols. I-IV, Blackwell Scientific Pubs. (1986); Fields, Knipe, & Howley, eds., Fields Virology (3' ed.) Vols. I & II, Lippincott Williams & Wilkins Pubs. (1996); Coligan et al., eds., Current Protocols in Immunology, John Wiley & Sons, New York, N.Y. (2000), each of which is incorporated herein by reference.

DETAILED DESCRIPTION

Figure 1:
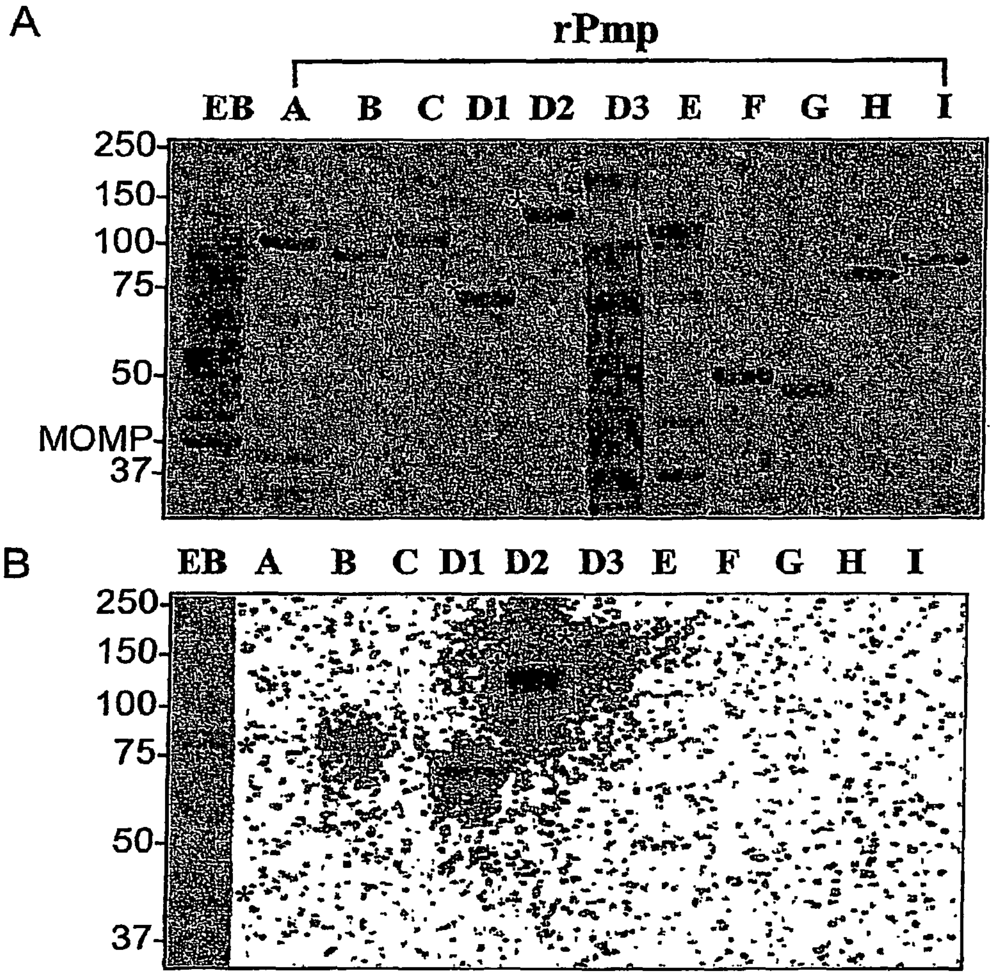
FIG. 1 depicts rabbit 155 kDa antiserum specific for PmpD. A. Protein gel of EB and rPmp *E. coli* lysates used in immunoblotting. B. Immunoblot with adsorbed rabbit 155 kDa antiserum. Lanes left to right: serovar E EB; partially purified rPmp polypeptides A, B, C, D1, D2, D3, E, F, G, H, and I. * The 155 kDa antiserum recognized 2 polypeptides (circa 80 and 42 kDa) in the EB lysate, and all 3 rPmpD polypeptides. The marked polypeptides in A correspond to the polypeptides recognized by the 155 kDa antiserum in B.

As noted above, the present invention is generally directed to compositions and methods for the diagnosis and treatment of Chlamydial infection. In one aspect, the compositions of the subject invention include polypeptides that comprise at least one immunogenic portion of a *Chlamydia* antigen, or a variant thereof.

In preferred aspects, methods are provided for stimulating an immune response to one or more of a *Chlamydia* bacterium serovariant in a subject, which methods may suitably comprise administering to a subject a passenger domain of a chlamydial polymorphic membrane protein D polypeptide in an amount sufficient to elicit production of antibodies, wherein the antibodies are capable of neutralizing at least two serovariants of *Chlamydia*, including at least three serovariants of *Chlamydia*.

Preferably, the passenger domain of the chlamydial polymorphic membrane protein D polypeptide comprises one or more of a polymorphic membrane protein D polypeptide from a *Chlamydia trachomatis* serovariant. A passenger domain also may be provided that comprises a polymorphic membrane protein D polypeptide.

Also preferred is where the passenger domain of the chlamydial polymorphic membrane protein D polypeptide is provided in a recombinant microorganism. The recombinant microorganism may be a recombinant virus comprising a passenger domain of a chlamydial polymorphic membrane protein D polypeptide-encoding polynucleotide for expression in the subject.

In specific embodiments, the subject invention includes polypeptides comprising an immunogenic portion of a *Chlamydia* antigen, wherein the *Chlamydia* antigen comprises an amino acid sequence encoded by a polynucleotide molecule including a sequence selected from the group consisting of (a) one or more nucleotide sequences recited in SEQ ID NOs: 1-3 or 10-12 (b) the complements of one or more of the nucleotide sequences, and (c) fragments or variants of the sequences.

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

As used in this specification and the appended claims, the singular forms “a,” “an” and “the” include plural references unless the content clearly dictates otherwise. Thus, for example, reference to “a cell” includes a mixture of two or more cells.

As used herein, the term “protein” refers to a polymer of amino acid residues, and is not limited to a minimum length. Polypeptides, peptides, oligopeptides, dimers, multimers, and the like, are included in the definition. Both full length proteins and fragments thereof are contemplated by the definition. The term also includes post-expression modifications to the protein, including, but not limited to, glycosylation, acetylation, phosphorylation.

As used herein, the phrase “functional fragment thereof” in reference to PmpD protein, refers to fragments of less than the full length of the protein that maintain the function of the PmpD protein, and are capable of inducing immunity or an immune response.

As used herein, the phrase “immunogenic fragment thereof” in reference to pdmpD protein, refers to fragments of less than the full length of the protein against which an immune response can be induced.

As used herein, “sufficient to elicit production of antibodies” refers to the amount that is sufficient for the subject to mount an immune response.

As used herein, “nucleic acid” includes DNA and RNA, as well as modified forms thereof, including modified sugars, bases, or backbone.

As used herein, “*Chlamydia* bacterium serovariant” and “*Chlamydia* bacteria” refer to the serovariants of *C. trachomatis*, including, for example, A, B, Ba, C, D, E, f, G, H, I, J, K, L1, L2, L3. *Chlamydia* infection and Chlamydial infection refer to the infection of a subject by a *Chlamydia* bacteria.

As used herein, “*chlamydia* related disorder or condition” refers to *Chlamydia* infections and related symptoms and conditions and to sexually transmitted diseases and trachoma.

As used herein, the phrase “free from *C. trachomatis* genome” used in reference to a nucleic acid encoding a PmpD protein, or functional fragment thereof, indicates that the nucleic acid is in a form that is in a recombinant form or construct, or that it is otherwise isolated from its natural state in a *C. trachomatis* genome.

As used herein, the phrase "free from *C. trachomatis* genome" used in reference to a nucleic acid encoding a PmpD protein, or functional fragment thereof, indicates that the nucleic acid is in a form that is in a recombinant form or construct, or that it is otherwise isolated from its natural state in a *C. trachomatis* genome.

As used herein, "injectable pharmaceutical composition" refers to pharmaceutically acceptable compositions for use in patients that are sterile, pyrogen-free, and free of any particulates. See, Remington's Pharmaceutical Sciences, 18th Ed., Gennaro, ed., Mack Publishing Co., Easton, Pa., 1990 and U.S.P., the standards of the U.S. Pharmacopeia, which is incorporated herein by reference.

As used herein, "pharmaceutically acceptable carrier" includes any carrier that does not itself induce a harmful effect to the individual receiving the composition. For example, a "pharmaceutically acceptable carrier" should not induce the production of antibodies harmful to the recipient. Suitable "pharmaceutically acceptable carriers" are known to those of skill in the art and are described in Remington's Pharmaceutical Sciences, supra.

As used herein, "treating" includes the amelioration and/or elimination of a disease or condition. The term "treating" is used in reference to individuals suffering from a *Chlamydia* infection or associated disease or condition characterized by *Chlamydia* infection and is also used in reference to individuals exposed to and/or infected with *C. trachomatis.*

As used herein, the phrase "effective amount" in reference to treating an individual having a disease or condition, means a quantity sufficient to effectuate treatment and ameliorate and/or eliminate the disease or condition.

As used herein, the phrase "immunologically effective amount" in reference to vaccine compositions, means a quantity sufficient to induce a therapeutic or prophylactic immune response.

As used herein, the phrase "prophylactic immune response" in reference to treating an individual against infection from a bacteria, means an immune response that is prophylactic and protects from challenge with the bacteria.

As used herein, the phrase "therapeutic immune response" in reference to treating an individual infected with a bacteria, means an immune response that ameliorates and/or eliminates the bacterial infection.

As used herein, the phrase "therapeutically effective amount" in reference to the amount of a vaccine administered to an individual, means a quantity sufficient to induce a therapeutic immune response in the individual.

As used herein, the phrase "prophylactically effective amount" in reference to the amount of a vaccine administered to an individual, means a quantity sufficient to induce a prophylactic immune response in the individual.

As used herein, "individual" refers to human and non-human animals that can be treated with pharmaceutical compositions or vaccine compositions of the invention.

As used herein, the term "administering" includes for example, injection, transdermal, parenteral, subcutaneous, intramuscular, oral, and topical delivery.

Polynucleotide Compositions

Another aspect of the present invention relates to pharmaceutical compositions that comprise a nucleic acid molecule that encodes a *C. trachomatis* PmpD protein, or a functional fragment thereof, and a pharmaceutically acceptable carrier or diluent. According to the present invention, genetic material that encodes *C. trachomatis* PmpD protein, or a functional fragment thereof, is delivered to an individual in an expressible form. The genetic material, DNA or RNA, is taken up by the cells of the individual and expressed. The *C. trachomatis* PmpD protein, or functional fragment thereof. Thus, pharmaceutical compositions comprising genetic material that encodes *C. trachomatis* PmpD protein, or functional fragment thereof, are useful in the same manner as pharmaceutical compositions comprising *C. trachomatis* PmpD protein, or functional fragments thereof for treating an individual having a pathology or condition characterized by or associated with *C. trachomatis* infection.

Thus, a further aspect of the present invention relates to a method of treating an individual suffering from a disease associated with *C. trachomatis* which comprises the step of administering to said individual an amount of nucleic acid that comprises a nucleotide sequence that encodes *C. trachomatis* PmpD protein, or a functional fragment thereof, operably linked to regulatory elements necessary for expression.

Another aspect of the present invention relates to vaccine compositions that comprise a nucleic acid molecule that encodes PmpD protein, or immunogenic fragment thereof, from *C. trachomatis*, and a pharmaceutically acceptable carrier or diluent. According to the present invention, genetic material that encodes PmpD protein, or an immunogenic fragment thereof, is delivered to an individual in an expressible form. The genetic material, DNA or RNA, is taken up by the cells of the individual and expressed. The PmpD protein, or immunogenic fragment thereof, that is thereby produced serves to induce an immune response in the individual. Thus, vaccine compositions comprising genetic material that encodes PmpD protein, or an immunogenic fragment thereof, from *C. trachomatis*, are useful in the same manner as vaccine compositions comprising PmpD protein for immunizing individuals. The immunity can be prophylactic if the individual is uninfected and therapeutic if the individual is infected. Accordingly, further aspects of the present invention relate to a method of preventing infection or treating infected individuals.

Nucleotide sequences that encode *C. trachomatis* PmpD protein, or a functional fragment thereof, operably linked to regulatory elements necessary for expression in the individual's cell, may be delivered as pharmaceutical compositions using gene therapy strategies which include, but are not limited to, either viral vectors such as adenovirus, vaccinia or retrovirus vectors or direct nucleic acid transfer. Methods of delivery of nucleic acids encoding proteins of interest, using viral vectors are widely reported. A recombinant viral vector such as a retroviral vector, vaccinia, adenovirus or adeno-associated viral vector is prepared using routine methods and starting materials. The recombinant viral vector comprises a nucleotide sequence that encodes *C. trachomatis* PmpD protein, or a functional fragment thereof. Such a vector is combined with a pharmaceutically acceptable carrier or diluent. The resulting pharmaceutical preparation may be administered to an individual. Once an individual is infected with the viral vector, *C. trachomatis* PmpD protein, or a functional fragment thereof, is produced in the infected cells.

Nucleotide sequences that encode *C. trachomatis* PmpD protein, or immunogenic fragments thereof, operably linked to regulatory elements necessary for expression in the individual's cell, may be delivered as vaccine compositions comprising viral vectors, such as adenovirus, adeno-associated virus, vaccinia virus or retrovirus vectors, or bacterial or mycobacterial vectors. Furthermore, the nucleotide sequences can be incorporated within live and/or attenuated vaccines.

Alternatively, a molecule which comprises a nucleotide sequence that encodes *C. trachomatis* PmpD protein, or a functional or immunogenic fragment thereof, can be administered as a pharmaceutical composition or vaccine by direct nucleic acid transfer, without the use of infectious vectors. The nucleic acid molecule may be DNA or RNA, preferably DNA. The DNA molecule may be linear or circular; it is preferably a plasmid. The nucleic acid molecule is combined with a pharmaceutically acceptable carrier or diluent.

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

Polynucleotides may comprise a native *Chlamydia* PmpD sequence or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native *Chlamydia* protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (e.g., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (e.g., the window size) and multiplying the results by 100 to yield the percentage of sequence identity.

Therefore, the present invention encompasses polynucleotide and polypeptide sequences having substantial identity to the sequences disclosed herein, e.g., SEQ ID NOs: 1-12, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using techniques such as, for example, hybridization, amplification and/or database sequence comparison.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

Polynucleotides may be identified, prepared and/or manipulated using any of a variety of well established techniques. For example, a polynucleotide may be identified, by screening a microarray of cDNAs for *Chlamydia* expression. Such screens may be performed, for example, using a Synteni microarray (Palo Alto, Calif.) according to the manufacturer's instructions (and essentially as described by Schena et al., Proc. Nat. Acad. Sci. USA 93:10614-10619, 1996 and Heller et al., Proc. Natl. Acad. Sci. USA 94:2150-2155, 1997). Alternatively, polynucleotides may be amplified from cDNA prepared from cells expressing the proteins described herein. Such polynucleotides may be amplified via polymerase chain reaction (PCR). For this approach, sequence-specific primers may be designed based on the sequences provided herein, and may be purchased or synthesized.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) Science 269:202-204) and automated synthesis may be achieved, for example, using the ABI 431A Peptide Synthesizer (Perkin Elmer, Palo Alto, Calif.).

In order to express a desired polypeptide, the nucleotide sequences encoding the polypeptide, or functional equivalents, may be inserted into appropriate expression vector, e.g., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector-enhancers, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) J. Biol. Chem. 264:5503-5509); and the like. PGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) EMBO J. 6:307-311. Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) Proc. Natl. Acad. Sci. 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

A host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

In addition to recombinant production methods, polypeptides of the invention, and fragments thereof, may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, as is well known in the art.

In Vivo Polynucleotide Delivery Techniques

In pharmaceutical compositions, the amount of nucleic acid is sufficient to be effectively expressed to induce cell death. If the nucleic acid encodes a fragment, the fragment must be a functional fragment. The pharmaceutical composition or vaccine comprising a nucleic acid sequence that encodes *C. trachomatis* or a other viruses including PmpD protein, or a functional fragment thereof, may be administered directly into the individual. The genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual. It is contemplated that otherwise non-immunogenic cells that have genetic constructs incorporated therein can be implanted into the individual even if the vaccinated cells were originally taken from another individual.

Genetic constructs may be administered, for example, by syringes, needleless injection devices, or "microprojectile bombardment gene guns." According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

According to the invention, the genetic vaccine may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection.

The pharmaceutical or vaccine compositions according to the present invention comprise about 1 nanogram to about 2000 micrograms of DNA. In some preferred embodiments, pharmaceutical or vaccine compositions according to the present invention comprise about 5 nanogram to about 1000 micrograms of DNA. In some preferred embodiments, the pharmaceutical or vaccine compositions contain about 10 nanograms to about 800 micrograms of DNA. In some preferred embodiments, the pharmaceutical or vaccine compositions contain about 0.1 to about 500 micrograms of DNA. In some preferred embodiments, the pharmaceutical or vaccine compositions contain about 1 to about 350 micrograms of DNA. In some preferred embodiments, the pharmaceutical or vaccine compositions contain about 25 to about 250 micrograms of DNA. In some preferred embodiments, the pharmaceutical or vaccine compositions contain about 100 to about 200 micrograms DNA.

The pharmaceutical or vaccine compositions according to the present invention are formulated according to the mode of administration to be used. In cases where pharmaceutical or vaccine compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

In some embodiments, nucleic acid molecules are delivered to the cells in conjunction with administration of a polynucleotide function enhancer or a "genetic vaccine facilitator" (GVF) agent. Polynucleotide function enhancers are described in U.S. Pat. Nos. 5,593,972, 5,981,505, and International Application Serial Number PCT/US94/00899, filed Jan. 26, 1994, which are each incorporated herein by reference. GVF agents are described in U.S. Pat. No. 5,739, 118, 5,837,533, and International Application Serial Number PCT/US99/04332, international filing date Feb. 26, 1999, each of which is incorporated herein by reference.

The co-agents, which are administered in conjunction with nucleic acid molecules, may be administered as a mixture with the nucleic acid molecule, or may be administered separately, simultaneously, before, or after administration of the nucleic acid molecules. In addition, other agents which may function as transfecting agents and/or replicating agents and/or inflammatory agents, and which may be co-administered with or without a GVF, include growth factors, cytokines, and lymphokines, such as .alpha.-interferon, .gamma.-interferon, platelet derived growth factor (PDGF), tumor necrosis factor (TNF), epidermal growth factor (EGF), interleukin-1 (IL-1), IL-2, IL-4, IL-6, IL-8, IL-10, and IL-12, as well as fibroblast growth factor, surface active agents, such as immune-stimulating complexes (ISCOMS), Freund's incomplete adjuvant, lipopolysaccharide (LPS) analogs, including monophosphoryl Lipid A (MPL), muramyl peptides, quinone analogs, vesicles, squalene, and squalene and hyaluronic acid. In some embodiments, an immunomodulating protein may be used as a GVF.

Nucleic acid molecules which are delivered to cells according to the invention may serve as genetic templates for proteins that function as prophylactic and/or therapeutic immunizing agents. In preferred embodiments, the nucleic acid the nucleic acid molecules comprise the necessary regulatory sequences for transcription and translation of the coding region in the cells of the animal.

The present invention relates to attenuated live vaccines and vaccines which use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, each of which is incorporated herein by reference. Gene constructs are provided which include the nucleotide sequence that encodes the PmpD protein is operably linked to regulatory sequences that can function in the vaccines to effect expression. The gene constructs are incorporated in the attenuated live vaccines and recombinant vaccines to produce vaccines according to the invention.

Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (tilts), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral pdmpD proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is beneficial to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Methods suitable to be here are exemplified by Racher et al. (1995), which disclosed improved methods for culturing 293 cells and propagating adenovirus.

The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it is most convenient to introduce the polynucleotide encoding the gene of interest at the position from which the E1-coding sequences have been removed. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Strafford-Perricaudet and Perricaudet, 1991; Strafford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

A large number of adenovirus-based expression vectors have been developed, primarily due to the advantages offered by these vectors in gene therapy applications. Adenovirus expression vectors and methods of using such vectors are the subject of a number of United States patents, including U.S. Pat. Nos. 5,698,202, 5,616,326, 5,585,362, and 5,518,913, all incorporated herein by reference.

Additional adenoviral constructs are described in Khatri et al. (1997) and Tomanin et al. (1997). Khatri et al. describe novel ovine adenovirus expression vectors and their ability to infect bovine nasal turbinate and rabbit kidney cells as well as a range of human cell type, including lung and foreskin fibroblasts as well as liver, prostate, breast, colon and retinal lines. Tomanin et al. describe adenoviral expression vectors containing the T7 RNA polymerase gene. When introduced into cells containing a heterologous gene operably linked to a T7 promoter, the vectors were able to drive gene expression from the T7 promoter. The authors suggest that this system may be useful for the cloning and expression of genes encoding cytotoxic proteins.

In one embodiment vaccinia virus and constructs thereof are useful. One of skill in the art would know how to make and use vaccinia virus constructs having the benefit of this present disclosure.

Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for pdmpD proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

To construct a retroviral vector, a nucleic acid encoding one or more oligonucleotide or polynucleotide sequences of interest is inserted into the viral genome in the place of certain viral sequences to produce a virus that is replication-defective. To produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

In certain embodiments, the genetic constructs comprising one or more polynucleotides of the invention are introduced into cells in vivo. This may be achieved by a variety of well known techniques, several of which are described below.

Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is enpdmpDated into pdmpD proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for PmpD protein VP1-3. Each ITR forms a T-shaped hairpin structure. These terminal repeats are the only essential cis components of the MV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the pdmpD proteins (Hermonat and Muzyczka, 1984).

Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

Murine leukemia virus (MLV)-based viral expression vectors have been developed by Kim et al. (1998). In creating the MLV vectors, Kim et al. found that the entire gag sequence, together with the immediate upstream region, could be deleted without significantly affecting viral packaging or gene expression. Further, it was found that nearly the entire U3 region could be replaced with the immediately-early promoter of human cytomegalovirus without deleterious effects. Additionally, MCR and internal ribosome entry sites (IRES) could be added without adverse effects. Based on their observations, Kim et al. have designed a series of MLV-based expression vectors comprising one or more of the features described above.

As more has been learned about human foamy virus (HFV), characteristics of HFV that are favorable for its use as an expression vector have been discovered. These characteristics include the expression of pol by splicing and start of translation at a defined initiation codon. Other aspects of HFV viral expression vectors are reviewed in Bodem et al. (1997).

Murakami et al. (1997) describe a Rous sarcoma virus (RSV)-based replication-competent avian retrovirus vectors, IR1 and IR2 to express a heterologous gene at a high level. In these vectors, the IRES derived from encephalomyocarditis virus (EMCV) was inserted between the env gene and the heterologous gene. The IR1 vector retains the splice-acceptor site that is present downstream of the env gene while the IR2 vector lacks it. Murakami et al. have shown high level expression of several different heterologous genes by these vectors.

Lentivirus-based retroviral expression vectors are also useful. Poxviruses are widely used for the expression of heterologous genes in mammalian cells. In an effort to diminish cytopathic effects and to increase safety, vaccinia virus mutant and other poxviruses that undergo abortive infection in mammalian cells are receiving special attention (Oertli et al., 1997). The use of poxviruses as expression vectors is reviewed in Carroll and Moss (1997).

Togaviral expression vectors, which includes alphaviral expression vectors have been used to study the structure and function of proteins and for protein production purposes. Attractive features of togaviral expression vectors are rapid and efficient gene expression, wide host range, and RNA genomes (Huang, 1996). Also, recombinant vaccines based on alphaviral expression vectors have been shown to induce a strong humoral and cellular immune response with good immunological memory and protective effects (Tubulekas et al., 1997). Alphaviral expression vectors and their use are discussed, for example, in Lundstrom (1997).

Baculoviral expression vectors have been used to express heterologous proteins in insect cells. Examples of proteins include mammalian chemokine receptors (Wang et al., 1997), reporter proteins such as green fluorescent protein (Wu et al., 1997), and FLAG fusion proteins (Wu et al., 1997; Koh et al., 1997). Recent advances in baculoviral expression vector technology, including their use in virion display vectors and expression in mammalian cells is reviewed by Possee (1997). Other reviews on baculoviral expression vectors include Jones and Morikawa (1996) and O'Reilly (1997).

Other suitable viral expression systems are disclosed, for example, in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. In other systems, the DNA may be introduced as "naked" DNA, as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

Non-Viral Vectors

To effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may comprise naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed, for example, one such device relies on a high voltage discharge to generate an electrical current, which in turn provides the motive force (Yang et al., 1990). The microprojectiles used have consisted of biologically inert substances such as tungsten or gold beads.

Selected organs, for example, include the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, e.g. ex vivo treatment. Again, DNA encoding a particular gene may be delivered via this method and still be incorporated by the present invention.

Polypeptide Compositions and Uses

*C. trachomatis* PmpD protein, or functional fragments thereof, may be produced by methods using readily available starting materials as described above. The nucleic acid sequence encoding *C. trachomatis* PmpD protein as well as the amino acid sequence of the protein are well known. The entire sequence of *C. trachomatis* PmpD is published and available in GenBank, including serovar A (accession number CP000051) and serovar D (accession number AE001273) both of which is incorporated herein by reference. There are a variety of publications relating to sequence information for the *C. trachomatis* genome, citations of which are linked to the sequence information in GenBank. Each of these references, including the publicly available sequence information, is incorporated herein by reference.

Sequence information for PmpD proteins can also be found in GenBank. By way of non-limiting examples, complete genome sequences of strains and isolates provided in GenBank, including serovar A (accession number CP000051) and serovar D (accession number AE001273) both of which is incorporated herein by, reference.

Provision of a suitable DNA sequence encoding a desired protein permits the production of the protein using recombinant techniques now known in the art. The coding sequence can be obtained by, for example, cloning it from infected cells, using PCR primers designed based upon the publicly available sequence information. The DNA sequence may also be prepared chemically using a DNA synthesizer. When the coding DNA is prepared synthetically, advantage can be taken of known codon preferences of the intended host where the DNA is to be expressed. Additionally, changes may be introduced into the coding sequence, such as point mutations, insertions, or deletions, to create controls and other modified forms of the PmpD protein.

One having ordinary skill in the art can, using well known techniques, obtain a DNA molecule encoding the *C. trachomatis* PmpD protein or a other viruses including PmpD protein and insert that DNA molecule into a commercially available expression vector for use in well known expression systems. For example, the commercially available plasmid pSE420 (Invitrogen, San Diego, Calif.) may be used for PmpD protein production in *E. coli* bacteria cells. The commercially available plasmid pYES2 (Invitrogen, San Diego, Calif.) may be used for production in yeast cells, such as *S. cerevisiae*. The commercially available MaxBac 2.0 Kit (Invitrogen, San Diego, Calif.), with the pBlueBac4 vector, is a complete baculovirus expression system that may be used for the production of PmpD protein in insect cells, such as Sf9 cells. The commercially available plasmid pcDNA I (nitrogen, San Diego, Calif.) may be used for the production of PmpD protein in mammalian cells, such as Chinese hamster ovary cells.

One having ordinary skill in the art can use these commercial expression vectors systems or others to produce *C. trachomatis* and other bacteria including PmpD proteins using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See, e.g., Ausubel et al., eds., Current Protocols in Molecular Biology, supra. Thus, the desired proteins can be prepared in both prokaryotic and eukaryotic systems, resulting in a spectrum of processed forms of the protein.

A commonly used prokaryotic system is *E. coli*, although other systems such as *Bacillus subtilis* and *Pseudomonas* are also useful. Suitable control sequences for prokaryotic systems include both constitutive and inducible promoters including, but not limited to, the lac promoter, the trp promoter, hybrid promoters such as the tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast cells, fungal cells, insect cells, mammalian cells, avian cells, and cells of higher plants. Suitable promoters are available which are compatible and operable for use in each of these host cell types. Also available, are termination sequences and enhancers, such as, for example, the baculovirus polyhedron promoter. As described above, promoters can be either constitutive or inducible. For example, in mammalian systems, the mouse metallothionine promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the *C. trachomatis* PmpD protein produced using such expression systems.

In addition to producing these proteins by recombinant techniques, automated amino acid synthesizers may also be employed to produce *C. trachomatis* PmpD protein, or functional fragments thereof. It should be further noted that if the proteins herein are made synthetically, substitution by amino acids which are not encoded by the gene may also be made. Alternative residues include, for example, the amino acids of the formula $H_2N(CH_2)_nCOOH$ wherein n is 2-6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

Pharmaceutical compositions used for treating diseases characterized by comprising a *C. trachomatis* PmpD protein, or functional fragment thereof; and a pharmaceutically acceptable carrier or diluent may be formulated by one of skill in the art with compositions selected depending upon the chosen mode of administration. Suitable pharmaceutical carriers are described in Remington's Pharmaceutical Sciences, supra., a reference text in this field.

A common requirement for any route of administration is efficient and easy delivery. In one embodiment of the invention, the pharmaceutical compositions are administered by injection. In a preferred embodiment, the compositions are administered by intra-tumoral injection. Other means of administration include, but are not limited to, transdermal, transcutaneous, subcutaneous, intraperitoneal, mucosal, or general persistent administration.

For parenteral administration, the *C. trachomatis* PmpD protein, or functional fragment thereof, can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

Although individual needs may vary, the determination of optimal ranges for effective amounts of formulations is within the skill of the art. Human doses can also readily be extrapolated from animal studies (Katocs et al., Chapter 27 In: Remington's Pharmaceutical Sciences, 18th Ed., Gennaro, ed., Mack Publishing Co., Easton, Pa., 1990, which is incorporated herein by reference). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: Goodman & Gilman's The Pharmacological Basis of Therapeutics, 9th Ed., Hardman et al., eds., McGraw-Hill, New York, N.Y., 1996, which is incorporated herein by reference). Usually, a daily dosage of *C. trachomatis* PmpD protein, or functional fragment thereof, can be about 1 μg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with therapies, which may be administered sequentially or simultaneously.

The pharmaceutical compositions comprising *C. trachomatis* PmpD protein, or functional fragments or derivatives thereof, may be administered by any means that enables the active agent to reach the agent's site of action in the body of the recipient. Because proteins are subject to digestion when administered orally, parenteral administration, e.g., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. If the individual to be treated is suffering from psoriasis, the *C. trachomatis* PmpD protein, or functional fragment thereof, may be formulated with a pharmaceutically acceptable topical carrier and the formulation may be administered topically as a creme, lotion or ointment for example.

Vaccine compositions, used for prophylactic or therapeutic treatment against *C. trachomatis* infection in an individual, comprising a *C. trachomatis* PmpD protein, or functional fragment thereof, and a pharmaceutically acceptable carrier or diluent, may be formulated by one of skill in the art with compositions selected depending upon the chosen mode of administration. Suitable pharmaceutical carriers for vaccines are described in Remington's Pharmaceutical Sciences, supra., a reference text in this field, and can include any carrier that does not itself induce the production of antibodies harmful to the individual receiving the composition. Suitable carriers include large, slowly metabolized macromolecules, such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria or tetanus.

Adjuvants that can be used with the vaccine compositions of the invention include, but are not limited to, (1) aluminum salts (alum), such as aluminum hydroxide, aluminum phosphate, aluminum sulfate, etc.; (2) oil-in-water emulsion formulations, such as for example, (a) Synthetic Adjuvant Formulation (SAF), available from Chiron (Emeryville, Calif.), and (b) Ribi Adjuvant System (RAS), (GlaxoSmith- Kline, Rixensart, Belgium.) containing detoxified endotoxin and mycobacterial cell wall components in 2% squalene; (3) water-in-oil formulations such as TiterMax, available from CytRx (Norcross, Ga.); (4) saponin adjuvants, such as Stimulon (Cambridge Bioscience, Worcester, Mass.) may be used or particles generated therefrom such as ISCOMS (immune-stimulating complexes); (4) Freund's Complete Adjuvant (FCA) and Freund's Incomplete Adjuvant (FIA); (5) cytokines, such as interleukins (IL-1, IL-2, etc.), macrophage colony stimulating factor (M-CSF), and tumor necrosis factor (INF), etc; and (6) other substances that act as immunostimulating agents to enhance the immunological effectiveness of the vaccine composition.

Vaccine compositions of the invention typically will contain diluents, such as water, saline, glycerol, ethanol, etc. Additionally, auxiliary substances, such as wetting or emulsifying agents, pH-buffering substances, and the like, may be present in such vehicles.

Vaccine compositions of the invention typically are prepared as injectables, either as liquid solutions or suspensions. Solid formulations, suitable for dissolving in, or suspending in, liquid vehicles prior to injection, may also be prepared: The preparation also may be emulsified or encapsulated in liposomes for enhanced adjuvant effect, as discussed above under pharmaceutically acceptable carriers.

The vaccine compositions of the present invention comprise an immunologically effective amount of *C. trachomatis* PmpD protein, or functional fragments or derivatives thereof, and may be administered by any method enabling the recipient's immune system to generate a prophylactic or therapeutic immune response. The immunologically effective amount of *C. trachomatis* PmpD protein, or functional fragments or derivatives thereof, is the quantity administered to an individual, either in a single dose or as part of a series, that is effective for therapeutic or prophylactic treatment of the individual. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating physician's assessment of the medical situation, and other relevant factors. It is expected that the amount will fall in a relatively broad range that can be determined through routine trials.

A common requirement for any route of administration is efficient and easy delivery. In one embodiment of the invention, the vaccine compositions are administered parenterally, e.g., by injection, either subcutaneous or intramuscular injection. Other means of administration include, but are not limited to, transdermal, transcutaneous, intraperitoneal, mucosal, or general persistent administration. Dosage treatment may be a single dose schedule or a multiple dose schedule. The vaccine may be administered in conjunction with other immunoregulatory agents and/or in conjunction with other vaccines.

The present invention, in other aspects, provides polypeptide compositions. Generally, a polypeptide of the invention will be an isolated polypeptide (or an epitope, variant, or active fragment thereof derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NOs: 1-12, or to active fragments, or to variants thereof, or to one or more nucleic acid sequences which hybridize to one or more of these sequences under conditions of moderate to high stringency.

As used herein, an active fragment of a polypeptide includes a whole or a portion of a polypeptide which is modified by techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a *Chlamydia* PmpD protein or a variant thereof, as described herein. Proteins that are *Chlamydia* proteins generally also react detectably within an immunoassay (such as an ELISA) with antisera from a patient with a Chlamydial infection. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (e.g., specifically bound) by a B-cell and/or T-cell surface antigen receptor. Such immunogenic portions generally comprise at least 5 amino acid residues, more preferably at least 10, and still more preferably at least 20 amino acid residues of a *Chlamydia* PmpD protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1-30 amino acids, preferably 5-15 amino acids), relative to the mature protein.

Immunogenic portions may generally be identified using well known techniques, such as those summarized in Paul, Fundamental Immunology, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (e.g., they react with the protein in an ELISA or other immunoassay, and do not react detectably with unrelated proteins). Such antisera and antibodies may be prepared as described herein, and using well known techniques. An immunogenic portion of a native *Chlamydia* protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native *Chlamydia* PmpD protein. A polypeptide "variant," as used herein, is a polypeptide that differs from a native *Chlamydia* protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His); or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known *Chlamydia* protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using techniques, for example, chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Nat. Acad. Sci. USA 83:8258-8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. New Engl. J. Med., 336:86-91, 1997).

Within preferred embodiments, an immunological fusion partner is derived from protein D, a surface protein of the gram-negative bacterium *Haemophilus* influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Therapeutic Compositions and Uses

The present invention also relates to vaccines comprising immunogenic fragments of *C. trachomatis* PmpD protein, and/or a nucleic acid encoding immunogenic fragments of *C. trachomatis* PmpD protein, to induce prophylactic or therapeutic immune responses in individuals. As used herein, an "immunogenic fragment" of "PmpD protein from *C. trachomatis*" refers to a fragment of *C. trachomatis* PmpD protein which is capable of inducing an immune response. Immunogenic fragments of *C. trachomatis* PmpD protein are at least about 10 amino acids in length, derived from *C. trachomatis* PmpD protein, and may comprise amino acid sequences that are not derived from *C. trachomatis* PmpD protein. One having ordinary skill in the art can readily determine whether a protein or peptide is an immunogenic fragment of *C. trachomatis* PmpD protein by the use of classical immunological assays to screen for antibody production in response to immunizations with fragments of *C. trachomatis* PmpD protein. These include, for example, 1) enzyme-linked immunosorbent assay (ELISA), 2) proliferation assays of cells from lymphoid organs, and 3) evaluation of the number of cells producing antibodies to a given antigen. Detailed protocols for these assays can be found in such manuals on immunology as Weir & Blackwell, eds., Handbook of Experimental Immunology, supra and Coligan et al., eds., Current Protocols in Immunology, supra. One having ordinary skill in the art can produce and identify immunogenic fragments of *C. trachomatis* PmpD protein following the disclosure provided herein and well known techniques. The immunogenic fragments thus identified may be used and formulated in place of full length *C. trachomatis* PmpD protein without undue experimentation.

Therapeutic aspects of the invention include use of *C. trachomatis* PmpD protein, a functional fragment of *C. trachomatis* PmpD protein, nucleic acid molecules encoding *C. trachomatis* PmpD protein, or nucleic acid molecules encoding a functional fragment of *C. trachomatis* PmpD protein in pharmaceutical compositions useful to treat an individual suffering from diseases characterized by or associated with *Chlamydia* infection, such as a sexually transmitted disease and/or trachoma.

According to one aspect of the invention, pharmaceutical compositions are provided which comprise either *C. trachomatis* PmpD protein, or a functional fragment thereof, or a nucleic acid molecule which comprises a DNA or RNA sequence that encodes *C. trachomatis* PmpD protein, or a functional fragment thereof.

Another aspect of the present invention relates to pharmaceutical compositions that comprise *C. trachomatis* PmpD protein, or a functional fragment thereof, and/or a nucleic acid molecule encoding *C. trachomatis* PmpD protein, or a functional fragment thereof, and a pharmaceutically acceptable carrier or diluent. Pharmaceutical compositions comprising *C. trachomatis* PmpD protein, or a functional fragment thereof, and/or a nucleic acid molecule encoding *C. trachomatis* PmpD protein, or a functional fragment thereof, are useful for treating an individual having a pathology or condition characterized by *Chlamydia* infection.

Another aspect of the present invention relates to vaccine compositions that comprise *C. trachomatis* PmpD protein, or an immunogenic fragment thereof, and/or a nucleic acid molecule encoding *C. trachomatis* PmpD protein, or an immunogenic fragment thereof, and a pharmaceutically acceptable carrier or diluent vaccine compositions comprising PmpD protein from *C. trachomatis*, or an immunogenic fragment thereof, are useful for immunizing an individual against *C. trachomatis*. The immunity may be prophylactic (to prevent infection) or therapeutic (to treat infection). Where the immunity is prophylactic, the individual is protected against challenge with the bacteria. Where the immunity is therapeutic, the individual's current *Chlamydia* infection is treated.

Accordingly, an aspect of the present invention is a method of treating an individual suffering from *C. trachomatis* infection, which comprises the step of administering to said individual an amount of PmpD protein, or an immunogenic fragment thereof, from *C. trachomatis*, sufficient to stimulate a therapeutic immune response.

Another aspect of the present invention is a method of preventing *C. trachomatis* infection in an individual, which comprises the step of administering to said individual an amount of PmpD protein, or an immunogenic fragment thereof, from *C. trachomatis*, sufficient to stimulate a prophylactic immune response.

When PmpD protein, or an immunogenic fragment thereof, from *C. trachomatis*, is delivered to an individual as a component in a vaccine (either directly as protein or by subsequent expression from a nucleic acid delivered in the vaccine), the PmpD protein, or immunogenic fragment thereof, becomes a target against which the individual develops an immune response, protecting from infection (prophylactic), or treating an infection (therapeutic). Those of skill in the art will recognize that the immune response can be both therapeutic and prophylactic, in that following a therapeutic treatment, the individual may be protected from further challenge with the bacteria.

In another aspect, the present invention provides methods for using one or more of the above polypeptides or fusion proteins (or polynucleotides encoding such polypeptides or fusion proteins) to induce protective immunity against Chlamydial infection in a patient. As used herein, a "patient" refers to any animal, preferably a human. A patient may be afflicted with a disease, or may be free of detectable disease and/or infection. In other words, protective immunity may be induced to prevent or treat Chlamydial infection or a Chlamydial related disorder.

In this aspect, the polypeptide, fusion protein or polynucleotide molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and an immunostimulant, such as an adjuvant or a liposome (into which the polypeptide is incorporated). Such pharmaceutical compositions and vaccines may also contain other *Chlamydia* antigens, either incorporated into a combination polypeptide or present within a separate polypeptide.

Alternatively, a vaccine may contain polynucleotides encoding one or more polypeptides or fusion proteins as described above, such that the polypeptide is generated in situ. In such vaccines, the polynucleotides may be present within any of a variety of delivery systems known to those of ordinary skill in the art, including nucleic acid expression systems, bacterial and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective) virus. Techniques for incorporating polynucleotides into such expression systems are well known to those of ordinary skill in the art. The polynucleotides may also be administered as "naked" plasmid vectors as described, for example, in Ulmer et al., Science 259:1745-1749, 1993 and reviewed by Cohen, Science 259:1691-1692, 1993. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The uptake of naked polynucleotides may be increased by incorporating the polynucleotides into and/or onto biodegradable beads, which are efficiently transported into the cells. The preparation and use of such systems is well known in the art.

In a related aspect, a polynucleotide vaccine as described above may be administered simultaneously with or sequentially to either a polypeptide of the present invention or a known *Chlamydia* antigen. For example, administration of polynucleotides encoding a polypeptide of the present invention, either "naked" or in a delivery system as described above, may be followed by administration of an antigen in order to enhance the protective immune effect of the vaccine.

Polypeptides and polynucleotides disclosed herein may also be employed in adoptive immunotherapy for the treatment of Chlamydial infection. Adoptive immunotherapy may be broadly classified into either active or passive immunotherapy. In active immunotherapy, treatment relies on the in vivo stimulation of the endogenous host immune system with the administration of immune response-modifying agents (for example, vaccines, bacterial adjuvants, and/or cytokines).

In passive immunotherapy, treatment involves the delivery of biologic reagents with established immune reactivity (such as effector cells or antibodies) that can directly or indirectly mediate anti-*Chlamydia* effects and does not necessarily depend on an intact host immune system. Examples of effector cells include T lymphocytes (for example, CD8+ cytotoxic T-lymphocyte, CD4+ T-helper), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

A method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," Immunological Reviews, 157:177, 1997).

The polypeptides disclosed herein may also be employed to generate and/or isolate chlamydial-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ or CD4+ T-cell clones may be isolated from the patient, expanded using tissue culture techniques, and returned to the patient.

Alternatively, peptides corresponding to immunogenic portions of the polypeptides may be employed to generate *Chlamydia* reactive T cell subsets by selective in vitro stimulation and expansion of autologous T cells to provide antigen-specific T cells which may be subsequently transferred to the patient as described, for example, by Chang et al, (Crit. Rev. Oncol. Hematol., 22(3), 213, 1996). Cells of the immune system, such as T cells, may be isolated from the peripheral blood of a patient, using a commercially available cell separation system, such as Isolex™ System, available from Nexell Therapeutics, Inc. Irvine, Calif. The separated cells are stimulated with one or more of the immunoreactive polypeptides contained within a delivery vehicle, such as a microsphere, to provide antigen-specific T cells. The population of antigen-specific T cells is then expanded using techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from *chlamydia* specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., Cancer Immunol Immunother, 45(3-4):131-6, 1997 and Hwu, P., et al, Cancer Res, 55(15):3369-73, 1995. Another embodiment may include the transfection of *chlamydia* antigen specific alpha and beta T cell receptor chains into alternate T cells, as in Cole, D J, et al, Cancer Res, 55(4):748-52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate disease in a murine model has been demonstrated by Cheever et al, Immunological Reviews, 157:177, 1997). Additionally, vectors expressing the disclosed polynucleotides may be introduced into stem cells taken from the patient and clonally propagated in vitro for autologous transplant back into the same patient.

In certain aspects, polypeptides, polynucleotides, T cells and/or binding agents disclosed herein may be incorporated into pharmaceutical compositions or immunogenic compositions (e.g., vaccines). Alternatively, a pharmaceutical composition may comprise an antigen-presenting cell (e.g. a dendritic cell) transfected with a Chlamydial polynucleotide such that the antigen presenting cell expresses a Chlamydial polypeptide. Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other Chlamydial antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope.

A vaccine may comprise a polynucleotide and/or a polypeptide component, as desired. It will also be apparent that a vaccine may contain pharmaceutically acceptable salts of the polynucleotides and/or polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *C. trachomatis* (add a space) derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, under select circumstances, the adjuvant composition may be designed to induce an immune response predominantly of the Th1 type or Th2 type. High levels of Th1-type cytokines (e.g., IFN-.gamma., tNF-alpha, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using assays. For a review of the families of cytokines, see Mosmann and Coffman, Ann. Rev. Immunol. 7:145-173, 1989.

Preferred adjuvants for use in eliciting a predominantly Th1 type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WO 99/33488. Immunostimulatory DNA sequences are also described, for example, by Sato et al., Science 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa Corporation; Seattle, Wash.), RC-529 (GlaxoSmithKline, Rixensart, Belgium.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any vaccine provided herein may be prepared using well known methods that result in a combination of antigen, immunostimulant and a suitable carrier or excipient. The compositions described herein may be administered as part of a sustained release formulation (e.g., a formulation such as a capsule, sponge or gel (composed of polysaccharides, for example) that effects a slow release of compound following administration). Such formulations may generally be prepared using well known technology (see, e.g., Coombes et al., Vaccine 14:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets *Chlamydia*-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-*Chlamydia* effects per se and/or to be immunologically compatible with the receiver (e.g., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic immunity (see Timmerman and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF-alpha to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF.alpha., CD40 ligand, LPS, flt3 ligand and/or other compound(s) that induce differentiation, maturation and proliferation of dendritic cells.

Dendritic cells are categorized, for example, as “immature” and “mature” cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fc receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a Chlamydial protein (or portion or other variant thereof such that the Chlamydial polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the Chlamydial polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Routes and frequency of administration of pharmaceutical compositions and vaccines, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1-36 week period. Preferably, 3 doses are administered, at intervals of 3-4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from Chlamydial infection for at least 1-2 years. In general, the amount of polypeptide present in a dose (or produced in situ by the DNA in a dose) ranges from about 1 pg to about 100 mg per kg of host, typically, from about 10 pg to about 1 mg, and preferably from about 100 pg to about 1 pg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In general, an appropriate dosage and treatment regimen provides the active compound(s) in an amount sufficient to provide therapeutic and/or prophylactic benefit. Such a response can be monitored by establishing an improved clinical outcome in treated patients as compared to non-treated patients. Increases in preexisting immune responses to a Chlamydial protein generally correlate with an improved clinical outcome. Such immune responses may generally be evaluated using, for example, proliferation, cytotoxicity or cytokine assays, which may be performed using samples obtained from a patient before and after treatment.

Antibodies

Antibodies

The differentiation of *C. trachomatis* from other *Chlamydia* may be accomplished with antibodies against PmpD. The presence of PmpD may be determined by several methods, including by immunofluorescence methods, for example using an anti-PmpD antibody, for example an antibody specific for a passenger domain of PmpD.

Various procedures known in the art may be used for the production of antibodies to PmpD, or fragments, derivatives, homologs or analogs of the proteins. Antibodies of the invention include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, i.e., molecules that contain an antigen binding site that immunospecifically binds to an antigen (e.g., one or more complementarity determining regions (CDRs) of an antibody).

For production of the antibody, various host animals can be immunized by injection with, e.g., a native PmpD protein or a synthetic version, or a derivative of the foregoing. Such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and *Corynebacterium parvum*. Although the following refers specifically to PmpD, any of the methods described herein apply equally to fragments thereof.

For preparation of monoclonal antibodies directed towards PmpD, any technique that provides for the production of antibody molecules by continuous cell lines in culture may be used. Such techniques include, but are not restricted to, the hybridoma technique originally developed by Kohler and Milstein (1975, Nature 256:495-497), the trioma technique (Gustafsson et al., 1991, Hum. Antibodies Hybridomas 2:26-32), the human s-cell hybridoma technique (Kozbor et al., 1983, Immunology Today 4:72), and the EBV hybridoma technique to produce human monoclonal antibodies (Cole et al., 1985, In: Monoclonal Antibodies and Cancer Therapy, Alan R. Liss, Inc., pp. 77-96). In an additional embodiment of the invention, monoclonal antibodies can be produced in germ-free animals utilizing recent technology described in International Patent Application PCT/US90/02545.

According to the present invention, human antibodies may be used and can be obtained by using human hybridomas (Cote et al., 1983, Proc. Natl. Acad. Sci. USA 80:2026-2030) or by transforming human B cells with EBV virus in vitro (Cole et al., 1985, In: Monoclonal Antibodies and Cancer Therapy, Alan R. Liss, Inc., pp. 77-96). In fact, according to the invention, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454) by splicing the genes from a mouse antibody molecule specific for PmpD together with genes from a human antibody molecule of appropriate biological activity can be used; such antibodies are within the scope of this invention.

According to the present invention, techniques described for the production of single chain antibodies (U.S. Pat. No. 4,946,778) can be adapted to produce PmpD-specific antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for PmpD proteins. Non-human antibodies can be "humanized" by known methods (e.g., U.S. Pat. No. 5,225,539).

Antibody fragments that contain the idiotypes of PmpD can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments. Synthetic antibodies, e.g., antibodies produced by chemical synthesis, are useful in the present invention.

In the production of antibodies, screening for the desired antibody can be accomplished by techniques known in the art, e.g., ELISA (enzyme-linked immunosorbent assay). To select antibodies specific to a particular domain of PmpD, or derivatives, homologs, or analogs thereof, one may assay generated hybridomas for a product that binds to the fragment of the PmpD, that contains such a domain.

An "epitope", as used herein, is a portion of a polypeptide that is recognized (i.e., specifically bound) by a B-cell and/or T-cell surface antigen receptor. Epitopes may generally be identified using well known techniques, such as those summarized in Paul, Fundamental Immunology, 3rd ed., 243-247 (Raven Press, 1993) and references cited therein, e.g., the passenger domains of the PmpD protein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

Methods for detecting the level of the protein may also include extracting the protein contents of the cells, or extracting fragments of protein from the membranes of the cells, or from the cytosol, for example, by lysis, digestive, separation, fractionation and purification techniques, and separating the proteinaceous contents of the cells (either the crude contents or the purified contents) on a western blot, and then detecting the presence of the protein, or protein fragment by various identification techniques known in the art. For example, the contents separated on a gel may be identified by using suitable molecular weight markers together with a protein identification technique, or using suitable detecting moieties (such as labeled antibodies, labeled lectins, labeled binding agents (agonists, antagonists, substrates, co-factors, ATP, etc.). The level of protein on the western blot may be normalized to a total protein level of the cell or to a standard internal protein, such as actin and/or GAPDH. The detection may also be by in situ, i.e., in the full tissue sample, by binding of specific recognition agents, to the biological markers when present in intact cells or in tissue. The presence of the labeled recognition moieties may be detected using techniques suited for the nature of the label. Where the recognition agents are fluorescent-labeled, the detection may be carried out by using a confocal microscope and directly viewing the level of the label bound (to the membranes). Where the recognition agents are labeled, for example, radio-labeled, the level may be determined by the determination of the radio-label level in the cells.

A sample may be tissue samples or cell from a subject, for example, obtained by biopsy, intact cells, for example cell that have been separated from a tissue sample, or intact cells present in blood or other body fluid, cells or tissue samples obtained from the subject, including paraffin embedded tissue samples, proteins extracted obtained from a cell, cell membrane, nucleus or any other cellular component or mRNA obtained from the nucleus or cytosol.

Alternatively it is possible to determine PmpD presence and/or localization by using labeled PmpD binding agents (e.g., antibodies, agonists, antagonists) especially fluorescent labeled binding agents. It is possible to monitor the localization of PmpD in cells, for example, using microscopy.

Detection and Diagnosis

In another aspect, the present invention provides methods for using the polypeptides described above to diagnose Chlamydial infection. In this aspect, methods are provided for detecting Chlamydial infection in a biological sample, using one or more of the above polypeptides, either alone or in combination. For clarity, the term "polypeptide" will be used when describing specific embodiments of the inventive diagnostic methods. However, it will be clear to one of skill in the art that the fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to *Chlamydia* antigens which may be indicative of *Chlamydia*-infection.

In embodiments in which more than one polypeptide is employed, the polypeptides used are preferably complementary (e.g., one component polypeptide will tend to detect infection in samples where the infection would not be detected by another component polypeptide). Complementary polypeptides may generally be identified by using each polypeptide individually to evaluate serum samples obtained from a series of patients known to be infected with *Chlamydia*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, Antibodies: A Laboratory Manual, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microliter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 pg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12-A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

To determine the presence or absence of anti-*Chlamydia* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for *Chlamydia*-infection. In an alternate preferred embodiment, the cut-off value is determined using a Receiver Operator Curve, according to the method of Sackett et al., Clinical Epidemiology: A Basic Science for Clinical Medicine, Little Brown and Co., 1985, pp. 106-107. Briefly, in this embodiment, the cut-off value may be determined from a plot of pairs of true positive rates (e.g., sensitivity) and false positive rates (100%−specificity) that correspond to each possible cut-off value for the diagnostic test result. The cut-off value on the plot that is the closest to the upper left-hand corner (e.g., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for Chlamydial infection.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*Chlamydia* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only. One example of an alternative assay protocol which may be usefully employed in such methods is a Western blot, wherein the proteins present in a biological sample are separated on a gel, prior to exposure to a binding agent. Such techniques are well known to those of skill in the art.

Binding Agents and Their Uses

The present invention further provides agents, such as antibodies and antigen-binding fragments thereof, that specifically bind to a Chlamydial PmpD protein. As used herein, an antibody, or antigen-binding fragment thereof, is said to "specifically bind" to a Chlamydial protein if it reacts at a detectable level (within, for example, an ELISA) with a Chlamydial protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a Chlamydial infection using the representative assays provided herein. In other words, antibodies or other binding agents that bind to a Chlamydial protein will generate a signal indicating the presence of a Chlamydial infection in at least about 20% of patients with the disease, and will generate a negative signal indicating the absence of the disease in at least about 90% of individuals without infection. To determine whether a binding agent satisfies this requirement, biological samples (e.g., blood, sera, sputum urine and/or tissue biopsies) from patients with and without Chlamydial infection (as determined using clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, Antibodies: A Laboratory Manual, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity (e.g., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using techniques known to those of skill in the art. Briefly, immunoglobulins may be purified from rabbit serum by affinity chromatography on Protein A bead columns (Harlow and Lane, Antibodies: A Laboratory Manual, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the met al, or met al oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in site-specific regions by appropriate methods. It will be evident that the precise dose of the antibody/immunoconjugate will vary depending upon the antibody used, the antigen density, and the rate of clearance of the antibody.

Antibodies may be used in diagnostic tests to detect the presence of *Chlamydia* antigens using assays similar to those detailed above and other techniques well known to those of skill in the art, thereby providing a method for detecting Chlamydial infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *Chlamydia*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

Kits

The present invention relates to methods of identifying individuals exposed to *C. trachomatis* by detecting presence of PmpD protein in a sample. The antibodies are preferably monoclonal antibodies. The antibodies are preferably raised against PmpD protein made in human cells, CHO cells, insect cells or yeast cells. Quantification of the amount of PmpD protein present in a sample of an individual may be used in determining the prognosis of an infected individual.

The present invention relates to antibodies which specifically bind to PmpD protein from *C. trachomatis*. The antibodies are preferably monoclonal antibodies. The antibodies are preferably raised against PmpD protein made in human cells, CHO cells, insect cells or yeast cells.

The present invention relates to kits for identifying individuals exposed to *C. trachomatis* comprising a first container which contains antibodies which specifically bind to PmpD protein from *C. trachomatis* and a second container which contains PmpD protein as a positive control. The antibodies are preferably monoclonal antibodies. The antibodies are preferably raised against PmpD protein made in human cells, CHO cells, insect cells or yeast cells. The PmpD protein is preferably made in human cells, CHO cells, insect cells or yeast cells. The kits may be adapted for quantifying of the amount of PmpD protein present in a sample of an individual.

Another aspect of the invention is a diagnostic test in which the presence and/or amount of anti-PmpD protein from *C. trachomatis* antibodies in a test sample is determined. In the diagnostic method of the present invention, the presence of anti-PmpD protein antibodies in a test sample from an individual is an indicator of infection.

The present invention relates to kits for identifying individuals exposed to *C. trachomatis* comprising a first container which contains antibodies which specifically bind to PmpD protein from *C. trachomatis* and a second container which contains PmpD protein. The PmpD protein is preferably produced in human cells, CHO cells, insect cells or yeast cells. The antibodies are preferably raised against PmpD made in human cells, CHO cells, insect cells or yeast cells. The kits may be adapted for quantifying the amount of anti-PmpD protein antibodies present in a sample of an individual. Such information may be used in determining the prognosis of an infected individual. The present invention also relates to methods of identifying individuals exposed to *C. trachomatis* by detecting presence of antibodies against PmpD protein from *C. trachomatis* in sample using PmpD protein. The PmpD protein is preferably produced in human cells, CHO cells' insect cells or yeast cells. Quantification of the amount of anti-PmpD protein antibodies present in a sample of an individual may be used in determining the prognosis of an infected individual. The present invention relates to isolated PmpD protein. The PmpD protein is preferably produced in human cells, CHO cells, insect cells or yeast cells. The proteins may be components of the kits.

Kits for the detection of PmpD protein from *C. trachomatis* and anti-PmpD protein from *C. trachomatis* antibodies are useful for research as well as diagnostic and prognostic purposes.

An "antibody composition" refers to the antibody or antibodies required for the detection of the protein. For example, the antibody composition used for the detection of PmpD protein in a test sample comprises a first antibody that binds to PmpD protein as well as a second or third detectable antibody that binds the first or second antibody, respectively.

In one embodiment, kits which are useful for the detection of PmpD protein in a test sample, comprise solid support, positive and negative controls, buffer, appropriate anti-PmpD protein antibodies and instructions for carrying out the capture ELISA assay essentially as previously described. Kits which are useful for the detection of anti-PmpD protein antibodies in a test sample, comprise solid support, positive and negative controls, buffer, PmpD protein and instructions for carrying out the capture ELISA assay essentially as previously described.

The compositions and methods of the present invention can be applied to veterinary medical uses as well. It is within the scope of the present invention to provide methods of treating non-human as well as human individuals. Accordingly, the present invention relates to a method of treating all animals, particularly mammalian species including human, bovine, ovine, porcine, equine, canine and feline species.

The invention is further illustrated by way of the following examples which are intended to elucidate the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLES

Chlamydial and Cell Cultures

*C. trachomatis* serovars A/HAR-13, B/TW-5/OT, Ba/Ap-2, C/TW-3/OT, D/UW-3/Cx, E/Bour, F/IC-Cal-3, G/UW- 524/Cx, H/UW-4/Cx, I/UW-12/Ur, J/UW-36/Cx, K/UW-31/Cx, L1/LGV-440, L2/LGV-434, L3/LGV-404, *C. muridarum* strain mouse pneumonitis (MoPn), *C. pneumoniae* (AR-39) and *C. caviae* strain guinea pig inclusion conjunctivitis (GPIC), were grown in HeLa 229 (ATCC CCL-2.1) and HaK (ATCC CCL-15) as previously described (29).

Antibodies

Rabbit polyclonal antiserum raised against L2 Ag-0.65 (155 kDa Ag) and the mouse mAb EVI-HI (genus-specific anti-LPS), Bb5 (anti-D MOMP), L21-45 (anti-L2 MOMP) and A57-B9 (anti-heat shock protein [HSP60]) were used in these studies.

Indirect Immunofluorescence

Chlamydial strains were grown on HeLa monolayers until mature inclusion formation, then methanol fixed and stained with either 155 kDa antiserum or mAb to LPS followed by Alexa Fluor 488 labeled secondary Abs (Invitrogen, Eugene, Oreg.).

Immunoblot Analysis

The pmp genes encoding Pmp A-I, including three different clones expressing overlapping polypeptides of the pmpD gene were expressed in *E. coli* as His-Tag fusion polypeptides (data not shown). Insoluble inclusion bodies were differentially extracted using Triton X-100 and sonication. The partially purified recombinant (r) Pmp polypeptides corresponding to amino acid (aa) residues 47-979 (rPmpA), 949-1747 (rPmpB), 994-1766 (rPmpC), 921-1528 (rPmpD1), 45-1079 (rPmpD2), 45-1528 (rPmpD3), 27-962 (rPmpE), 28-449 (rPmpF), 139-502 (rPmpG), 337-1009 (rPmpH) 30-879 (rPmpI) and serovar E EB were loaded on 10% SDS-PAGE gels and transferred to PVDF membranes (Amersham Biosciences, NJ, USA). Each lane was visually standardized by Coomassie Brilliant Blue staining to contain approximately 1-2 μg protein of full length rPmp or 10 μg of EB. Pre-immune and anti-155 kDa sera were pre-absorbed with inclusion bodies of the His-Tagged recombinant capsid protein from chlamydiaphage phiCPG1 (data not shown). The serum was diluted 1:1000 against rPmps and 1:500 against E EB. Membranes were blotted with the pre-absorbed serum followed by an HRP-conjugated anti-rabbit secondary Ab (KPL, MD, USA). The blots were visualized with ECL (SuperSignal West Dura Extended Duration Substrate, Pierce, Ill., USA) and read using ImageQuant (5.2) software.

Immunodot Blot

Viable serovar D EB were blotted onto a nitrocellulose membrane in a BIO-DOT microfiltration apparatus (Bio-Rad Laboratories, Richmond, Calif.) and reacted with mouse mAb specific to D MOMP, LPS, and HSP60, rabbit anti-155 kDa and pre-immune sera as previously described (21). Detection of primary Ab reactivity with EB surface Ag was modified from previous work by incubating nitrocellulose membrane with alkaline phosphatase conjugated secondary Ab (Zymed, Invitrogen, So. San Francisco, Calif.). Blots were developed with solutions of 5-bromo-4-chloro-3-indolyl phosphate plus nitroblue tetrazolium salt (Zymed) as described by the manufacturer.

Neutralization Assays

In vitro neutralization of chlamydial infectivity in HAK cells was performed by adding $1\times10^6$ EB/ml to two-fold dilutions of anti-155 kDa and pre-immune sera, and assaying for infection forming units (IFU) as previously described (30). Mouse mAb to MOMP, LPS, or isotype matched irrelevant mouse mAb were used as positive and negative controls, respectively. Percent specific neutralization was calculated as ([pre-immune IFU−immune IFU]/pre-immune IFU)×100 for each dilution. For blocking assays, primary (blocking) and secondary Ab concentrations were optimized for assay in either HaK or HeLa cells. For Hak 10 μg/ml of mAb and 1:50 dilution of sera was used; for Hela 100 μg/ml of mAb and 1:25 dilution of sera was used. EB were incubated with primary (blocking) Ab for 30 min, secondary Ab was added and incubation continued for 30 min. EB-Ab mixtures were plated onto monolayers and assayed for IFU as described above.

Rabbit Antiserum to 155 kDa Ag is Specific to PmpD

As part of a screen for Abs reactive with *C. trachomatis* rPmps, included was rabbit antiserum generated against the 155 kDa Ag. The rPmps and EB were immunoblotted with the rabbit 155 kDa antiserum (FIG. 1). The predominant rPmp present in each lysate is shown by gel electrophoresis in FIG. 1A. By immunoblot, 155 kDa antiserum reacted with only EB and rPmpD polypeptides (FIG. 1B). Pre-immune rabbit serum was not reactive with EB or rPmpD polypeptides (data not shown). The most intensely reacting rPmpD fragment was D2 (aa 45-1079). These findings indicate that antiserum to the 155 kDa Ag is specific for PmpD, a conclusion further supported by the predicted mass of *C. trachomatis* PmpD, which is ~161 kDa (31, 32). Interestingly, the antiserum specifically recognized two polypeptides of circa 80 and 42 kDa in EB lysates, suggesting that *C. trachomatis* PmpD is processed similarly to PmpD of *C. pneumoniae* (33). With these findings the 155 kDa antiserum is now referred to as PmpD antiserum.

PmpD is a *C. trachomatis* Species-Common Ag

Figure 2:
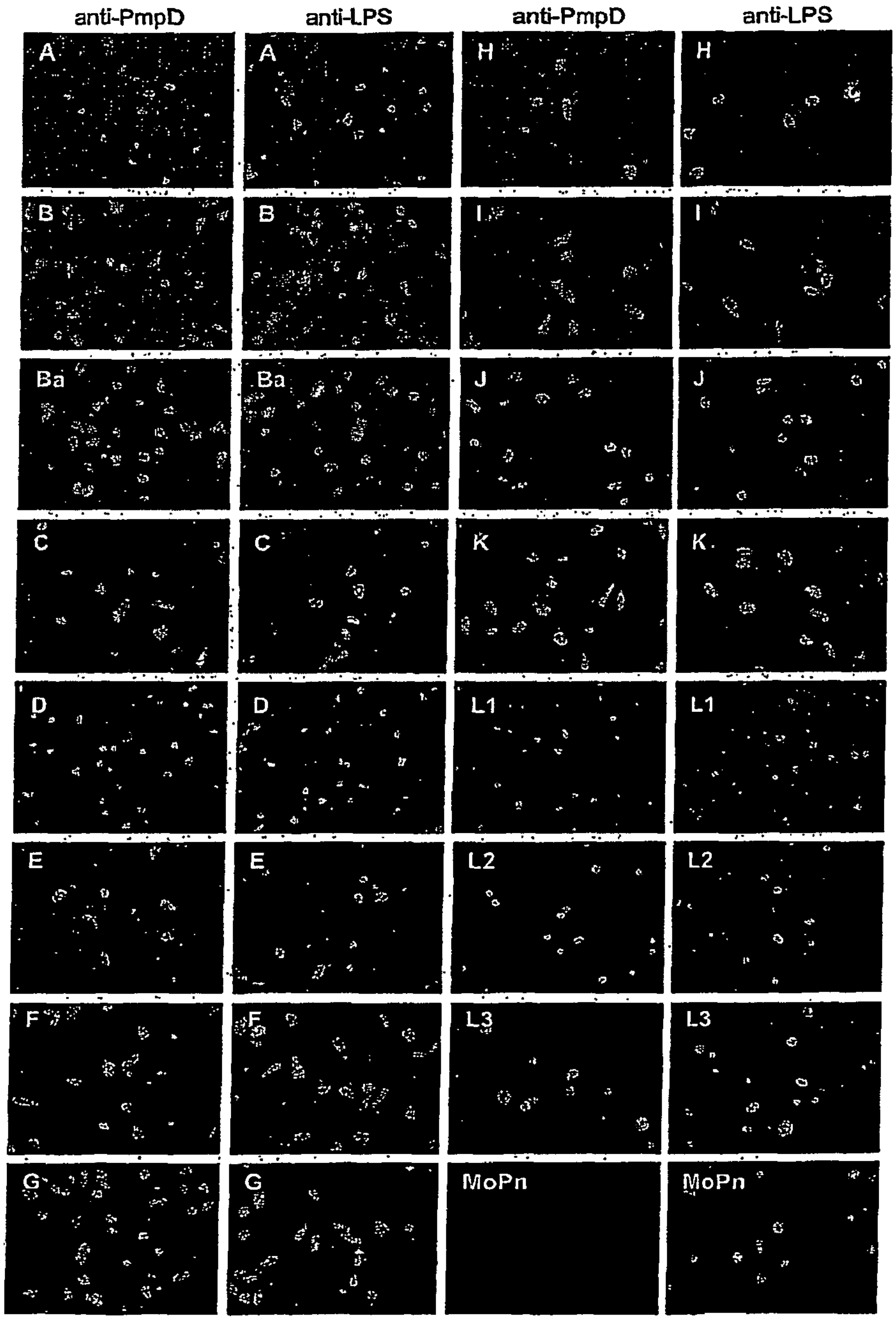
FIG. 2 depicts that PmpD is a species-common *C. trachomatis* Ag. HeLa cells infected with the 15 *C. trachomatis* (A-L3) serovars and *C. muridarum* (MoPn) were stained by IFA with PmpD antiserum. Inclusions for each of the *C. trachomatis* serovars (A-L3) reacted strongly with PmpD antiserum. In contrast, inclusions of *C. muridarum* (MoPn) failed to react. Inclusions of all 16 strains reacted with mAb to LPS.

As an initial characterization tested were chlamydial strains which reacted with PmpD antiserum by indirect fluorescent antibody (IFA). To confirm that PmpD is a *C. trachomatis* species-common Ag included were all 15 *C. trachomatis* serovars as well as *C. muridarum* (MoPn). PmpD sequence alignments are 99.15% identical between *C. trachomatis* serovars (31, 32). In contrast, PmpD of *C. trachomatis* is 71.46% identical to PmpD of *C. muridarum* (MoPn), 34.74% identical to PmpD of *C. pneumoniae*, and 36.50% identical to PmpD of *C. caviae* (34-36). Inclusions of all 15 *C. trachomatis* serovars, but not *C. muridarum* stained strongly with PmpD antiserum (FIG. 2). In contrast, mAb to genus-specific LPS stained both *C. trachomatis* and *C. muridarum* inclusions. To determine if PmpD antiserum reacted with equal intensity with all *C. trachomatis* serovars, endpoint titrations were conducted on HeLa cells infected with all 15 *C. trachomatis* serovars, *C. muridarum, C. pneumoniae*, and *C. caviae*. The endpoint titer was 1:3200 for each *C. trachomatis* serovar suggesting that the density and exposure of the PmpD protein was similar among *C. trachomatis* serovars. *C. muridarum, C. caviae*, and *C. pneumoniae* did not react with PmpD antiserum at any dilution tested (Table 1).

TABLE 1

Endpoint Titration of Anti-PmpD to Chlamydial Serovars/Strains

| *C. trachomatis* serotype/strain | anti-PmpD (reciprocal dilution) 100 | 200 | 400 | 800 | 1600 | 3200 | 6400 |
|---|---|---|---|---|---|---|---|
| B complex serotype | | | | | | | |
| B/TW-5 | +++[a] | +++ | ++ | ++ | + | + | − |
| Ba/AP-2 | +++ | +++ | ++ | ++ | + | + | − |
| D/UW-3 | +++ | +++ | ++ | ++ | + | + | − |
| E/Bour | +++ | +++ | ++ | ++ | + | + | − |
| L1/440 | +++ | +++ | ++ | ++ | + | + | − |
| L2/434 | +++ | +++ | ++ | ++ | + | + | − |

TABLE 1-continued

Endpoint Titration of Anti-PmpD to Chlamydial Serovars/Strains

| *C. trachomatis* | anti-PmpD (reciprocal dilution) | | | | | | |
|---|---|---|---|---|---|---|---|
| serotype/strain | 100 | 200 | 400 | 800 | 1600 | 3200 | 6400 |
| C complex serotype | | | | | | | |
| A/HAR-13 | +++ | +++ | ++ | ++ | + | + | − |
| C/TW-3 | +++ | +++ | ++ | ++ | + | + | − |
| H/UW-4 | +++ | +++ | ++ | ++ | + | + | − |
| I/UW-12 | +++ | +++ | ++ | ++ | + | + | − |
| J/UW-36 | +++ | +++ | ++ | ++ | + | + | − |
| Intermediate serotype | | | | | | | |
| F/IC-Cal | +++ | +++ | ++ | ++ | + | + | − |
| G/UW-524 | +++ | +++ | ++ | ++ | + | + | − |
| K/UW-31 | +++ | +++ | ++ | ++ | + | + | − |
| L3/404 | +++ | +++ | ++ | ++ | + | + | − |
| *C. muridarium* MoPn | − | − | − | − | − | − | − |
| *C. pneumoniae* | − | − | − | − | − | − | − |
| *C. psittaci* GPIC | − | − | − | − | − | − | − |

[a]fluorescence intensity: +++ strong, ++ moderate, + weak, − negative

PmpD is Surface Exposed

Figure 3:
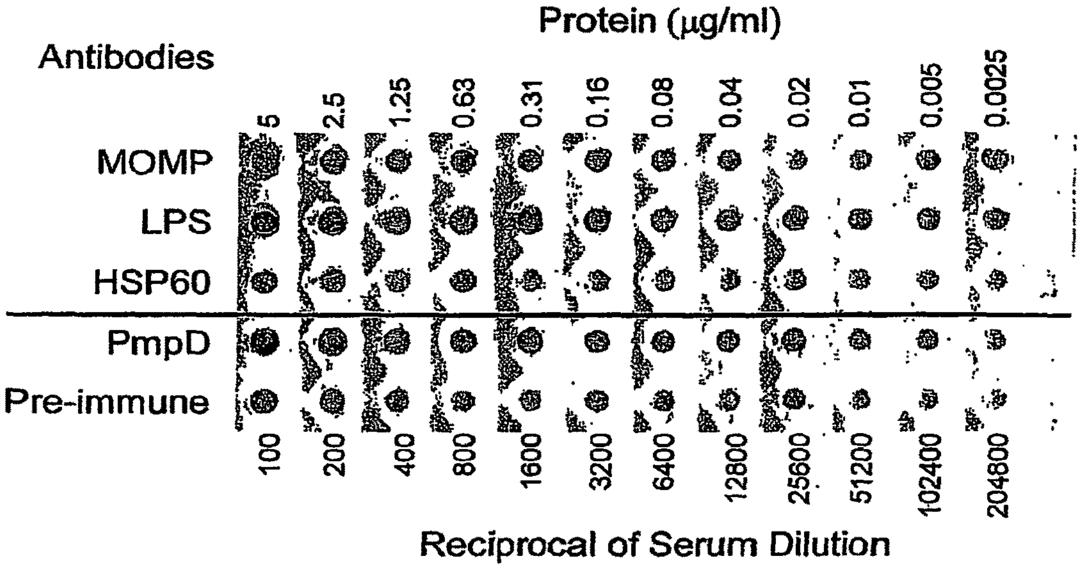
FIG. 3 depicts that PmpD is surface exposed. Viable serovar D EB were blotted onto nitrocellulose membrane and incubated with different mAb (upper panel) rabbit anti-PmpD and pre-immune sera (lower panel) to assay for PmpD surface exposure on native chlamydiae. MAb against MOMP and LPS reacted with EB whereas mAb specific to HSP60 was non-reactive. PmpD antiserum reacted with EB, but pre-immune serum was non-reactive. Protein concentrations are shown for mAb and reciprocal dilutions for anti-PmpD and pre-immune sera.

To determine if PmpD is surface exposed and a potential target of neutralizing Abs, viable EB were blotted onto a nitrocellulose membrane and reacted With PmpD antiserum or mAb against MOMP, LPS (which are both surface exposed) or HSP60 (a cytoplasmic non-surface exposed Ag) (FIG. 3). Consistent with previous reports (21, 30), mAb specific to MOMP and LPS, but not HSP60, were reactive with viable EB. PmpD antiserum, but not pre-immune serum, was also reactive with viable EB, demonstrating that PmpD is surface exposed. All mAb reacted with serovar D-infected HeLa cells by IFA (data not shown).

PmpD is a Species-Common Pan-Neutralizing Target

Figure 4:
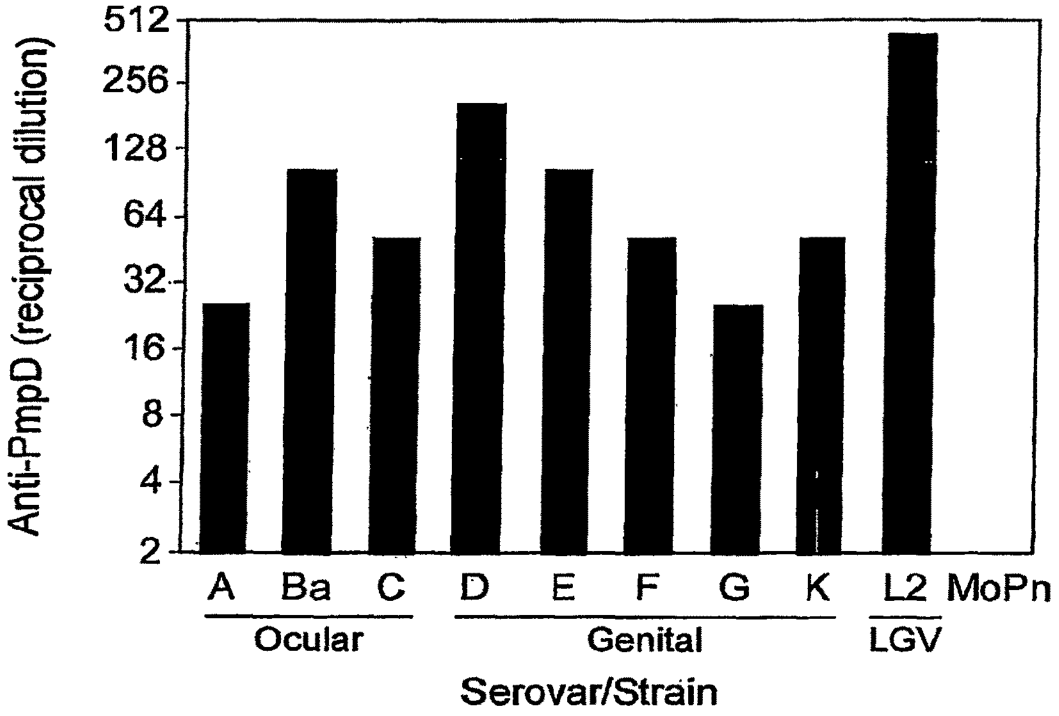
FIG. 4 depicts that PmpD is a target of neutralizing Abs. The neutralizing activity of PmpD antiserum was assayed against *C. trachomatis* serovars A, Ba, C, D, K, and L2 and *C. muridarum* (MoPn). Results are expressed as the reciprocal of the serum dilution resulting in 50% reduction in IFU (50% end-points). The experiment was repeated twice in triplicate; representative data from a single experiment is depicted. PmpD antiserum neutralized *C. trachomatis* serovars, but failed to neutralize the infectivity of *C. muridarum* (MoPn).

Surface exposure of PmpD suggested it might be a neutralizing target. MOMP is the only known target of neutralizing Abs (22). Chlamydial LPS is not a neutralizing target. LPS Abs actually enhance chlamydial infectivity (37). It was then determined whether PmpD antiserum was neutralizing or non-neutralizing. Neutralizing 50% endpoint determinations were performed in HaK cells on representative serovars from the three major *C. trachomatis* serogroups (B, C, and intermediate complex) representing ocular (A, Ba, and C), genital noninvasive (D and K), and genital invasive (L2) serovars. The PmpD antiserum titer that resulted in a 50% reduction in IFU for each serovar and for the negative control strain *C. muridarum* (MoPn) is shown in FIG. 4. The titers resulting in a 50% reduction in IFU varied for each serovar. B complex serovars (Ba, D, and L2) were more efficiently neutralized than C complex (A, C) and intermediate complex (K) serovars. PmpD antiserum failed to neutralize *C. muridarium*. These findings show that *C. trachomatis* PmpD is a species-common pan-neutralizing target.

Abs to MOMP and LPS Block the Neutralizing Ability of PmpD Antiserum

Figure 5:
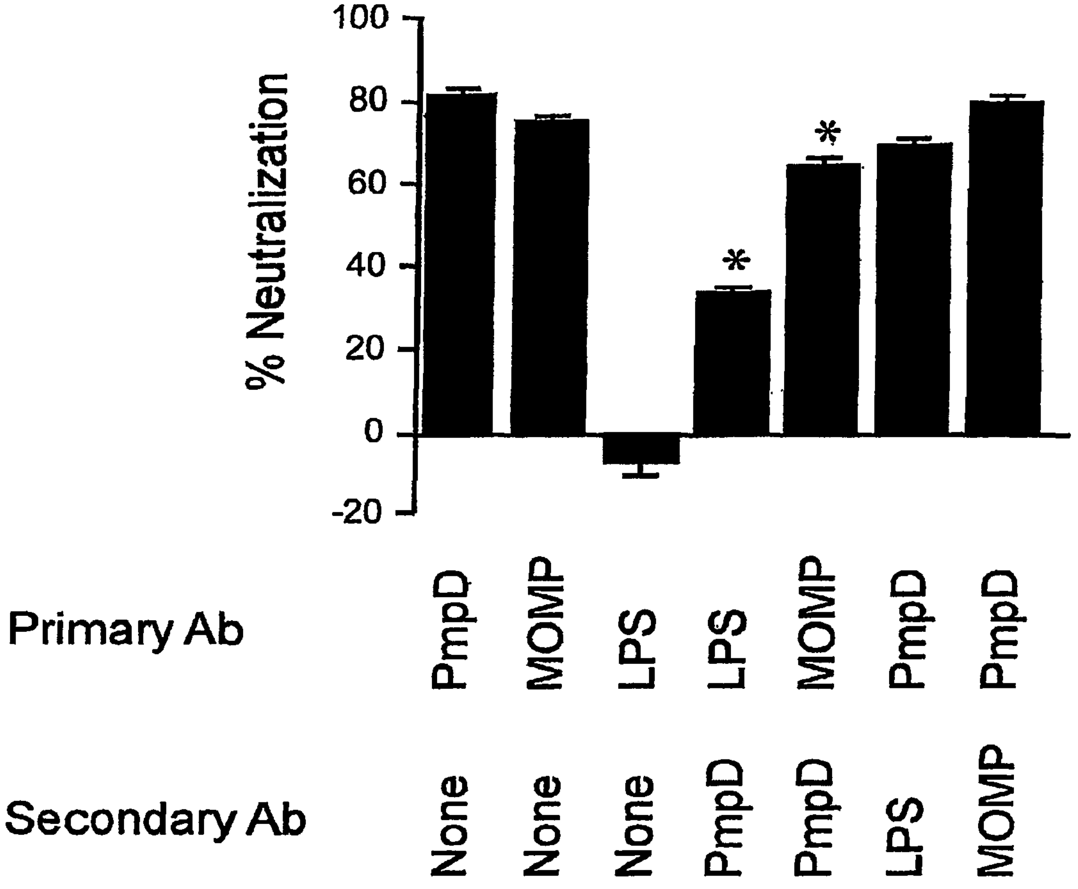
FIG. 5 depicts Abs to MOMP and LPS inhibit anti-PmpD mediated neutralization of chlamydial infectivity. Blocking neutralization assays using A) FcR negative HaK cells and B) FcR positive HeLa cells. Serovar D EB were incubated with different primary and secondary Abs then plated onto cell monolayers and assayed for IFU to determine percent neutralization. In HaK cells Abs to PmpD or MOMP Abs were neutralizing, whereas Abs to LPS were not neutralizing, but instead enhanced infectivity. Pre-incubation with Abs to LPS or MOMP significantly blocked the ability of anti-PmpD Abs to neutralize infectivity (*$P<0.05$). Pre-incubation with anti-PmpD Abs negated the blocking effect of Abs to LPS or MOMP. In HeLa cells anti-PmpD Abs were neutralizing, but Abs to both MOMP and LPS enhanced infectivity. Pre-incubation with Abs to either LPS or MOMP significantly blocked the ability of anti-PmpD Abs to neutralize infectivity (*$P<0.05$). Pre-incubation with anti-PmpD Abs negated the enhanced infectivity of anti-LPS or anti-MOMP Abs.

Without wishing to be bound by any scientific theories, it was hypothesized that MOMP immunodominant serovar-specific Abs might mask PmpD species-common neutralizing Ags and hence block the neutralizing activity of anti-PmpD Abs. To test this hypothesis EB were pre-incubated with serovar-specific mAb to MOMP or genus-specific mAb to LPS, followed by incubation with PmpD antiserum, and assayed for infectivity for HaK and Hela cells (FIG. 5). HaK cells lack FcR while HeLa cells express them; providing infection targets that are permissive, and non-permissive, respectively to IgG mediated neutralization (30, 38). In HeLa cells uptake of IgG bound chlamydiae is by Fc mediated endocytosis. Despite this alternate entry pathway, EB retain the ability to modify the nascent endocytic vesicle to form an inclusion permissive for pathogen replication (39). Thus, Abs that block attachment in FcR negative cells (HaK), such as Abs to MOMP, are unable to neutralize infectivity for HeLa cells (23). These two neutralization assay systems were used t to both determine if Abs to immunodominant Ags block anti-PmpD function and better understand the possible mechanism(s) of how anti-PmpD Abs neutralize infectivity.

When assayed in HaK cells PmpD antiserum or mAb to MOMP were neutralizing (FIG. 5A). mAb to LPS was non-neutralizing and enhanced infectivity. Anti-LPS mAB was very effective in blocking the neutralizing activity of PmpD antiserum ($P<0.05$). Anti-MOMP mAb also significantly blocked the neutralizing activity of PmpD antiserum ($P<0.05$), however this effect was less marked than that observed for anti-LPS mAb most likely because both anti-MOMP mAb and PmpD antiserum are neutralizing in HaK cells. When PmpD antiserum was incubated with EB prior to either anti-LPS or anti-MOMP mAbs the blocking effect of both Abs was negated.

Similar experiments were performed in FcR bearing HeLa cells (FIG. 5B). Both anti-MOMP and anti-LPS mAbs were non-neutralizing in HeLa cells, and increased infectivity due to the combined effect of FcR and ordinary EB mediated uptake. This enhanced infectivity is reflected by a negative neutralization value. Interestingly, PmpD antiserum retained neutralizing activity for HeLa cells despite FcR mediated EB uptake. These findings suggest that PmpD functions at an early step post-infection that is independent of chlamydial attachment and entry. Consistent with our findings in HaK cells, pre-incubation with either anti-MOMP or anti-LPS mAbs blocked the neutralizing activity of PmpD antiserum for HeLa cells ($P<0.05$). Conversely, pre-incubation with PmpD antiserum reversed the infection enhancing activities of both anti-MOMP and anti-LPS mAbs, suggesting that the function of PmpD is essential for early chlamydial development or growth.

Chlamydial Pmps resemble autotransporters of gram negative bacteria (40, 41). Despite functional diversity, autotransporters possess common characteristics that include translocation across the inner membrane in a Sec-dependent manner, secretion of the amino-terminal portion (the passenger domain) of the protein to the bacterial cell surface and a carboxy-terminal translocator domain (42). The translocator domain forms a beta-barrel structure through which the passenger domain transverses, resulting in a secreted product capable of interacting with the extracellular environment. The passenger domain may or may not be proteolytically cleaved upon translocation across the outer membrane (42). *C. trachomatis* possesses 9 different pmp genes, all of which are expressed (43). In *C. pneumoniae*, the pmp orthologs include 21 genes, which are divided into 6 gene families: A, B/C, D, E/F, G, and H (40). Among the pmps, pmpD is the least variable between species at both the nucleotide and amino acid level. Genes exhibiting a low degree of sequence variation between strains, as well as between species, often carry out essential functions. In contrast, polymorphic genes may: (i) be modified due to an altered functional selection, (ii) be under greater immunogenic pressure, (iii) act in a pathogen-host specific manner, or combinations thereof.

Recently, Wehrl et al. (33) reported that *C. pneumoniae* PmpD is surface exposed and a target of neutralizing Ab.

Figure 6:
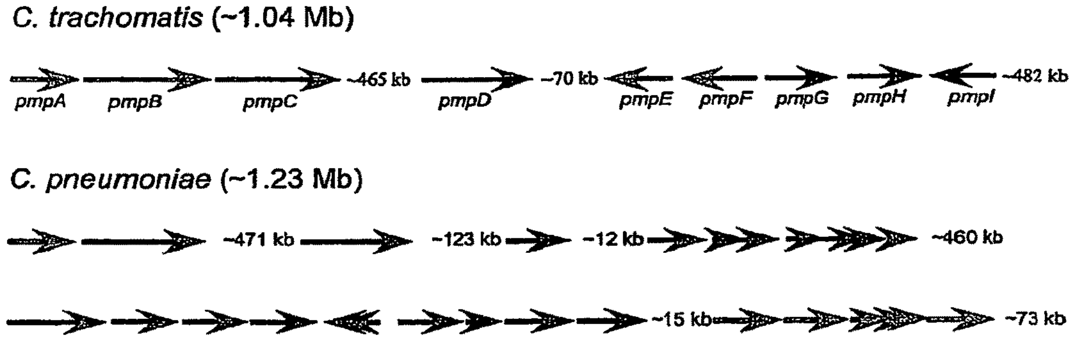
FIG. 6 depicts gene arrangement of the pmp gene family in the *C. trachomatis* and *C. pneumoniae* genomes. The sequenced *C. trachomatis* genomes are approximately 1.04 Mb while the *C. pneumoniae* genomes are approximately 1.23 Mb in size. The gene families are identified via differing colors, as originally assigned by Grimwood and Stephens (40). (pmpA=yellow, pmpB/C=green, pmpD=red, pmpE/F=orange, pmpG=blue, pmpH=purple, and pmpI=black) The chromosomal distance between each pmp gene/gene cluster is indicated in kilobases (kb).

These authors also showed PmpD is proteolytically cleaved and the amino-terminal portion translocates to the cell surface. The *C. trachomatis* pmpD gene, encoding a predicted polypeptide of 150 kDa, is virtually identical (99.15%) among *C. trachomatis* serovars (31, 32), but not among other chlamydial species (34-36). FIG. 6 shows the general chromosomal arrangement of the pmps in both *C. trachomatis* and *C. pneumoniae*. Although the pmp gene family is highly polymorphic, pmpD is unique. Organizationally the pmpD genes are physically isolated and unaltered in relative gene organization between the two species. Conservation of pmpD in *C. trachomatis* serovars suggests that if PmpD is surface accessible, similar to *C. pneumoniae* PmpD, it could function as a species-common pan-neutralizing target for *C. trachomatis* isolates. Our results demonstrating that *C. trachomatis* PmpD is surface exposed and a target of neutralizing Ab are consistent with those of Wehrl et al. (33) for *C. pneumoniae* PmpD. Moreover, the *C. trachomatis* PmpD also appears to be proteolytically processed in a fashion similar to that of *C. pneumoniae* PmpD. Based on the similarity of PmpD to autotransporters, the majority of the PmpD protein in the mature EB would be predicted to be in the processed, rather than full length form. Because PmpD is expressed by all *C. trachomatis* serovars, it likely serves a common function in pathogenesis. The ability of anti-PmpD serum to neutralize infectivity in FcR expressing HeLa cells suggests that PmpD functions early.

Preexisting Abs to MOMP or LPS effectively block anti-PmpD neutralization in vitro. However, this is not the case if PmpD Abs are preexisting. These in vitro findings have implications to in vivo immunity. MOMP and LPS are immunodominant Ags during natural infection of humans (17) and non-human primates (13, 26). Primary anti-MOMP responses are serovar-specific (21) and protection is homotypic (26). MOMP and LPS are abundant on the EB surface (30), while PmpD, appears to be a less abundant protein. In vivo, abundant immunodominant surface Ags may function as decoys for the immune system by blocking the binding of more broadly protective species-common pan-neutralizing Abs. This decoy function could explain serovar-specific immunity to re-infection because Abs to PmpD would be prevented from binding their cognate neutralizing target(s). Without wishing to be bound by any scientific theories, it is proposed that preexisting Abs to MOMP and LPS prevent Abs specific to PmpD from functioning in protective immunity.

Serovar A pmpD (SEQ ID NO.: 1)

ATGAGTTCCGAGAAAGATATAAAAAGCACCTGTTCTAAGTTTTCTTTATCTGTAGTAGCA

GCTATCCTTGCCTCTGTTAGCGGGTTAGCTAGTTGCGTAGATCTTCATGCTGGAGGACAG

TCTGTAAATGAGCTGGTATATGTAGGCCCTCAAGCGGTTTTATTGTTAGACCAAATTCGA

GATCTATTCGTTGGGTCTAAAGATAGTCAGGCTGAAGGACAGTATAGGTTAATTGTAGGA

GATCCAAGTTCTTTCCAAGAGAAAGATGCGGATACTCTTCCCGGGAAGGTAGAGCAAAGT

ACTTTGTTCTCAGTAACCAATCCCGTGGTTTTCCAAGGTGTGGACCAACAGGATCAAGTC

TCTTCCCAAGGGTTAATTTGTAGTTTTACGAGCAGCAACCTTGATTCTCCTCGTGACGGA

GAATCTTTTTTAGGTATTGCTTTTGTTGGGGATAGTAGTAAGGCTGGAATCACATTAACT

GACGTGAAAGCTTCTTTGTCTGGAGCGGCTTTATATTCTACAGAAGATCTTATCTTTGAA

AAGATTAAGGGTGGATTGGAATTTGCATCATGTTCTTCTCTAGAACAGGGGGGAGCTTGT

GCAGCTCAAAGTATTTTGATTCATGATTGTCAAGGATTGCAGGTTAAACACTGTACTACA

GCCGTGAATGCTGAGGGGTCTAGTGCGAATGATCATCTTGGATTTGGAGGAGGCGCTTTC

TTTGTTACGGGTTCTCTTTCTGGAGAGAAAAGTCTCTATATGCCTGCAGGAGATATGGTA

GTTGCGAATTGTGATGGGGCTATATCTTTTGAAGGAAACAGCGCGAACTTTGCTAATGGA

GGAGCGATTGCTGCCTCTGGGAAAGTGCTTTTTGTCGCTAATGATAAAAAGACTTCTTTT

ATAGAGAACCGAGCTTTGTCTGGAGGAGCGATTGCAGCCTCTTCTGATATTGCCTTTCAA

AACTGCGCAGAACTAGTTTTCAAAGGCAATTGTGCAATTGGAACAGAGGATAAAGGTTCT

TTAGGTGGAGGGGCTATATCTTCTCTAGGCACCGTTCTTTTGCAAGGGAATCACGGGATA

ACTTGTGATAAGAATGAGTCTGCTTCGCAAGGAGGCGCCATTTTTGGCAAAAATTGTCAG

ATTTCTGACAACGAGGGGCCAGTGGTTTTCAGAGATAGTACAGCTTGCTTAGGAGGAGGC

GCTATTGCAGCTCAAGAAATTGTTTCTATTCAGAACAATCAGGCTGGGATTTCCTTCGAG

GGAGGTAAGGCTAGTTTCGGAGGAGGTATTGCGTGTGGATCTTTTTCTTCCGCAGGTGGT

GCTTCTGTTTTAGGGACCATTGATATTTCGAAGAATTTAGGCGCGATTTCGTTCTCTCGT

ACTTTATGTACGACCTCAGATTTAGGACAAATGGAGTACCAGGGAGGAGGAGCTCTATTT

GGTGAAAATATTTCTCTTTCTGAGAATGCTGGTGTGCTCACCTTTAAAGACAACATTGTG

-continued

AAGACTTTTGCTTCGAATGGGAAAATTCTGGGAGGAGGAGCGATTTTAGCTACTGGTAAG

GTGGAAATTACCAATAATTCCGAAGGAATTTCTTTTACAGGAAATGCGAGAGCTCCACAA

GCTCTTCCAACTCAAGAGGAGTTTCCTTTATTCAGCAAAAAAGAAGGGCGACCACTCTCT

TCAGGATATTCTGGGGGAGGAGCGATTTTAGGAAGAGAAGTAGCTATTCTCCACAACGCT

GCAGTAGTATTTGAGCAAAATCGTTTGCAGTGCAGCGAAGAAGAAGCGACATTATTAGGT

TGTTGTGGAGGAGGCGCTGTTCATGGGATGGATAGCACTTCGATTGTTGGCAACTCTTCA

GTAAGATTTGGTAATAATTACGCAATGGGACAAGGAGTCTCAGGAGGAGCTCTTTTATCT

AAAACAGTGCAGTTAGCTGGAAATGGAAGCGTCGATTTTTCTCGAAATATTGCTAGTTTG

GGAGGAGdAGCTCTTCAAGCTTCTGAAGGAAATTGTGAGCTAGTTGATAACGGCTATGTG

CTATTCAGAGATAATCGAGGGAGGGTTTATGGGGGTGCTATTTCTTGCTTACGTGGAGAT

GTAGTCATTTCTGGAAACAAGGGTAGAGTTGAATTTAAAGACAACATAGCAACACGTCTT

TATGTGGAAGAAACTGTAGAAAAGGTTGAAGAGGTAGAGCCAGCTCCTGAGCAAAAAGAC

AATAATGAGCTTTCTTTCTTAGGGAGTGCAGAACAGAGTTTTATTACTGCAGCTAATCAA

GCTCTTTTCGCATCTGAAGATGGGGATTTATCACCTGAGTCATCCATTTCTTCTGAAGAA

CTTGTGAAAAGAAGAGAGTGTGCTGGAGGAGCTATTTTTGCAAAACGGGTTCGTATTGTA

GATAACCAAGAGGCCGTTGTATTCTCGAATAACTTCTCTGATATTTATGGCGGCGCCATT

TTTACAGGTTCTCTTCGAGAAGAGGATAAGTTAGATGGGCAAATCCCTGAAGTCTTGATC

TCAGGCAATGCAGGGGATGTTGTTTTTTCCGGAAATTCCTCGAAGCGTGATGAGCATCTT

CCTCATACAGGTGGGGGAGCCATTTGTACTCAAAATTTGACGATTTCTCAGAATACAGGG

AATGTTCTGTTTTATAACAACGTGGCCTGTTCGGGAGGAGCTGTTCGTATAGAGGATCAT

GGTAATGTTCTTTTAGAAGCTTTTGGAGGAGATATTATTTTTAAAGGAAATTCTTCTTTC

AGAGCACAAGGATCCGATGCTATCTATTTTGCAGGTAAAGAATCGCATATTACAGCCCTG

AATGCTACGGAAGGACATGCTATTGTTTTCCACGACGCATTAGTTTTTGAAAATCTAGAA

GAAAGGAAATCTGCTGAAGTATTGTTAATCAATAGTCGAGAAAATCCAGGTTACACTGGA

TCTATTCGATTTTTAGAAGCAGAAAGTAAAGTTCCTCAATGTATTCATGTACAACAAGGA

AGCCTTGAGTTGCTAAATGGAGCCACATTATGTAGTTATGGTTTTAAACAAGATGCTGGA

GCTAAGTTGGTATTGGCTGCTGGAGCTAAACTGAAGATTTTAGATTCAGGAACTCCTGTA

CAACAAGGGCATGCTATCAGTAAACCTGAAGCAGAAATCGAGTCATCTTCTGAACCAGAG

GGTGCACATTCTCTTTGGATTGCGAAGAATGCTCAAACAACAGTTCCTATGGTTGATATC

CATACTATTTCTGTAGATTTAGCCTCCTTCTCTTCTAGTCAACAGGAGGGGACAGTAGAA

GCTCCTCAGGTTATTGTTCCTGGAGGAAGTTATGTTCGATCTGGAGAGCTTAATTTGGAG

TTAGTTAACACAACAGGTACTGGTTATGAAAATCATGCTTTGTTGAAGAATGAGGCTAAA

GTTCCATTGATGTCTTTCGTTGCTTCTGGTGATGAAGCTTCAGCCGAAATCAGTAACTTG

TCGGTTTCTGATTTACAGATTCATGTAGTAACTCCAGAGATTGAAGAAGACACATACGGC

CATATGGGAGATTGGTCTGAGGCTAAAATTCAAGATGGAACTCTTGTCATTAGTTGGAAT

CCTACTGGATATCGATTAGATCCTCAAAAAGCAGGGGCTTTAGTATTTAATGCATTATGG

GAAGAAGGGGCTGTCTTGTCTGCTCTGAAAAATGCACGCTTTGCTCATAATCTCACTGCT

CAGCGTATGGAATTCGATTATTCTACAAATGTGTGGGGATTCGCCTTTGGTGGTTTCCGA

ACTCTATCTGCAGAGAATCTGGTTGCTATTGATGGATACAAAGGAGCTTATGGTGGTGCT

TCTGCTGGAGTCGATATTCAATTGATGGAAGATTTTGTTCTAGGAGTTAGTGGAGCTGCT

-continued

TTCCTAGGTAAAATGGATAGTCAGAAGTTTGATGCGGAGGTTTCTCGGAAGGGAGTTGTT

GGTTCTGTATATACAGGATTTTTAGCTGGATCCTGGTTCTTCAAAGGACAATATAGCCTT

GGAGAAACACAGAACGATATGAAAACGCGTTATGGAGTACTAGGAGAGTCGAGTGCTTCT

TGGACATCTCGAGGAGTACTGGCAGATGCTTTAGTTGAATACCGAAGTTTAGTTGGTCCT

GTGAGACCTACTTTTTATGCTTTGCATTTCAATCCTTATGTCGAAGTATCTTATGCTTCT

ATGAAATTCCCTGGCTTTACAGAACAAGGAAGAGAAGCGCGTTCTTTTGAAGACGCTTCC

CTTACCAATATCACCATTCCTTTAGGGATGAAGTTTGAATTGGCGTTCATAAAAGGACAG

TTTTCAGAGGTGAACTCTTTGGGAATAAGTTATGCATGGGAAGCTTATCGAAAAGTAGAA

GGAGGCGCGGTGCAGCTTTTAGAAGCTGGGTTTGATTGGGAGGGAGCTCCAATGGATCTT

CCTAGACAGGAGCTGCGTGTCGCTCTGGAAAATAATACGGAATGGAGTTCTTACTTCAGC

ACAGTCTTAGGATTAACAGCTTTTTGTGGAGGATTTACTTCTACAGATAGTAAACTAGGA

TATAAGGCGAATACTGGATTGCGATTGATCTTTTAA

Serovar D pmpD (SEQ ID NO.: 2)

ATGAGTTCCGAGAAAGATATAAAAAGCACCTGTTCTAAGTTTTCTTTGTCTGTAGTAGCA

GCTATCCTTGCCTCTGTTAGCGGGTTAGCTAGTTGCGTAGATCTTCATGCTGGAGGACAG

TCTGTAAATGAGCTGGTATATGTAGGCCCTCAAGCGGTTTTATTGTTAGACCAAATTCGA

GATCTATTCGTTGGGTCTAAAGATAGTCAGGCTGAAGGACAGTATAGGTTAATTGTAGGA

GATCCAAGTTCTTTCCAAGAGAAAGATGCGGATACTCTTCCCGGGAAGGTAGAGCAAAGT

ACTTTGTTCTCAGTAACCAATCCCGTGGTTTTCCAAGGTGTGGACCAACAGGATCAAGTC

TCTTCCCAAGGGTTAATTTGTAGTTTTACGAGCAGCAACCTTGATTCTCCTCGTGACGGA

GAATCTTTTTTAGGTATTGCTTTTGTTGGGGATAGTAGTAAGGCTGGAATCACATTAACT

GACGTGAAAGCTTCTTTGTCTGGAGCGGCTTTATATTCTACAGAAGATCTTATCTTTGAA

AAGATTAAGGGTGGATTGGAATTTGCATCATGTTCTTCTCTAGAACAGGGGGGAGCTTGT

GCAGCTCAAAGTATTTTGATTCATGATTGTCAAGGATTGCAGGTTAAACACTGTACTACA

GCCGTGAATGCTGAGGGGTCTAGTGCGAATGATCATCTTGGATTTGGAGGAGGCGCTTTC

TTTGTTACGGGTTCTCTTTCTGGAGAGAAAAGTCTCTATATGCCTGCAGGAGATATGGTA

GTTGCGAATTGTGATGGGGCTATATCTTTTGAAGGAAACAGCGCGAACTTTGCTAATGGA

GGAGCGATTGCTGCCTCTGGGAAAGTGCTTTTTGTCGCTAATGATAAAAAGACTTCTTTT

ATAGAGAACCGAGCTTTGTCTGGAGGAGCGATTGCAGCCTCTTCTGATATTGCCTTTCAA

AACTGCGCAGAACTAGTTTTCAAAGGCAATTGTGCAATTGGAACAGAGGATAAAGGTTCT

TTAGGTGGAGGGGCTATATCTTCTCTAGGCACCGTTCTTTTGCAAGGGAATCACGGGATA

ACTTGTGATAAGAATGAGTCTGCTTCGCAAGGAGGCGCCATTTTTGGCAAAAATTGTCAG

ATTTCTGACAACGAGGGGCCAGTGGTTTTCAGAGATAGTACAGCTTGCTTAGGAGGAGGC

GCTATTGCAGCTCAAGAAATTGTTTCTATTCAGAACAATCAGGCTGGGATTTCCTTCGAG

GGAGGTAAGGCTAGTTTCGGAGGAGGTATTGCGTGTGGATCTTTTTCTTCCGCAGGTGGT

GCTTCTGTTTTAGGGACCATTGATATTTCGAAGAATTTAGGCGCGATTTCGTTCTCTCGT

ACTTTATGTACGACCTCAGATTTAGGACAAATGGAGTACCAGGGAGGAGGAGCTCTATTT

GGTGAAAATATTTCTCTTTCTGAGAATGCTGGTGTGCTCACCTTTAAAGACAACATTGTG

AAGACTTTTGCTTCGAATGGGAAAATTCTGGGAGGAGGAGCGATTTTAGCTACTGGTAAG

GTGGAAATTACTAATAATTCCGAAGGAATTTCTTTTACAGGAAATGCGAGAGCTCCACAA

GCTCTTCCAACTCAAGAGGAGTTTCCTTTATTCAGCAAAAAAGAAGGGCGACCACTCTCT

-continued

TCAGGATATTCTGGGGGAGGAGCGATTTTAGGAAGAGAAGTAGCTATTCTCCACAACGCT

GCAGTAGTATTTGAGCAAAATCGTTTGCAGTGCAGCGAAGAAGAAGCGACATTATTAGGT

TGTTGTGGAGGAGGCGCTGTTCATGGGATGGATAGCACTTCGATTGTTGGCAACTCTTCA

GTAAGATTTGGTAATAATTACGCAATGGGACAAGGAGTCTCAGGAGGAGCTCTTTTATCT

AAAACAGTGCAGTTAGCTGGGAATGGAAGCGTCGATTTTTCTCGAAATATTGCTAGTTTG

GGAGGAGGAGCTCTTCAAGCTTCTGAAGGAAATTGTGAGCTAGTTGATAACGGCTATGTG

CTATTCAGAGATAATCGAGGGAGGGTTTATGGGGGTGCTATTTCTTGCTTACGTGGAGAT

GTAGTCATTTCTGGAAACAAGGGTAGAGTTGAATTTAAAGACAACATAGCAACACGTCTT

TATGTGGAAGAAACTGTAGAAAAGGTTGAAGAGGTAGAGCCAGCTCCTGAGCAAAAAGAC

AATAATGAGCTTTCTTTCTTAGGGAGAGCAGAACAGAGTTTTATTACTGCAGCTAATCAA

GCTCTTTTCGCATCTGAAGATGGGGATTTATCACCTGAGTCATCCATTTCTTCTGAAGAA

CTTGCGAAAAGAAGAGAGTGTGCTGGAGGAGCTATTTTTGCAAAACGGGTTCGTATTGTA

GATAACCAAGAGGCCGTTGTATTCTCGAATAACTTCTCTGATATTTATGGCGGCGCCATT

TTTACAGGTTCTCTTCGAGAAGAGGATAAGTTAGATGGGCAAATCCCTGAAGTCTTGATC

TCAGGCAATGCAGGGGATGTTGTTTTTTCCGGAAATTCCTCGAAGCGTGATGAGCATCTT

CCTCATACAGGTGGGGGAGCCATTTGTACTCAAAATTTGACGATTTCTCAGAATACAGGG

AATGTTCTGTTTTATAACAACGTGGCCTGTTCGGGAGGAGCTGTTCGTATAGAGGATCAT

GGTAATGTTCTTTTAGAAGCTTTTGGAGGAGATATTGTTTTTAAAGGAAATTCTTCTTTC

AGAGCACAAGGATCCGATGCTATCTATTTTGCAGGTAAAGAATCGCATATTACAGCCCTG

AATGCTACGGAAGGACATGCTATTGTTTTCCACGACGCATTAGTTTTTGAAAATCTAGAA

GAAAGGAAATCTGCTGAAGTATTGTTAATCAATAGTCGAGAAAATCCAGGTTACACTGGA

TCTATTCGATTTTTAGAAGCAGAAAGTAAAGTTCCTCAATGTATTCATGTACAACAAGGA

AGCCTTGAGTTGCTAAATGGAGCCACATTATGTAGTTATGGTTTTAAACAAGATGCTGGA

GCTAAGTTGGTATTGGCTGCTGGAGCTAAACTGAAGATTTTAGATTCAGGAACTCCTGTA

CAACAAGGGCATGCTATCAGTAAACCTGAAGCAGAAATCGAGTCATCTTCTGAACCAGAG

GGTGCACATTCTCTTTGGATTGCGAAGAATGCTCAAACAACAGTTCCTATGGTTGATATC

CATACTATTTCTGTAGATTTAGCCTCCTTCTCTTCTAGTCAACAGGAGGGGACAGTAGAA

GCTCCTCAGGTTATTGTTCCTGGAGGAAGTTATGTTCGATCTGGAGAGCTTAATTTGGAG

TTAGTTAACACAACAGGTACTGGTTATGAAAATCATGCTTTATTGAAGAATGAGGCTAAA

GTTCCATTGATGTCTTTCGTTGCTTCTGGTGATGAAGCTTCAGCCGAAATCAGTAACTTG

TCGGTTTCTGATTTACAGATTCATGTAGTAACTCCAGAGATTGAAGAAGACACATACGGC

CATATGGGAGATTGGTCTGAGGCTAAAATTCAAGATGGAACTCTTGTCATTAGTTGGAAT

CCTACTGGATATCGATTAGATCCTCAAAAAGCAGGGGCTTTAGTATTTAATGCATTATGG

GAAGAAGGGGCTGTCTTGTCTGCTCTGAAAAATGCACGCTTTGCTCATAATCTCACTGCT

CAGCGTATGGAATTCGATTATTCTACAAATGTGTGGGGATTCGCCTTTGGTGGTTTCCGA

ACTCTATCTGCAGAGAATCTGGTTGCTATTGATGGATACAAAGGAGCTTATGGTGGTGCT

TCTGCTGGAGTCGATATTCAATTGATGGAAGATTTTGTTCTAGGAGTTAGTGGAGCTGCT

TTCCTAGGTAAAATGGATAGTCAGAAGTTTGATGCGGAGGTTTCTCGGAAGGGAGTTGTT

GGTTCTGTATATACAGGATTTTTAGCTGGATCCTGGTTCTTCAAAGGACAATATAGCCTT

GGAGAAACACAGAACGATATGAAAACGCGTTATGGAGTACTAGGAGAGTCGAGTGCTTCT

-continued

TGGACATCTCGAGGAGTACTGGCAGATGCTTTAGTTGAATACCGAAGTTTAGTTGGTCCT

GTGAGACCTACTTTTTATGCTTTGCATTTCAATCCTTATGTCGAAGTATCTTATGCTTCT

ATGAAATTCCCTGGCTTTACAGAACAAGGAAGAGAAGCGCGTTCTTTTGAAGACGCTTCC

CTTACCAATATCACCATTCCTTTAGGGATGAAGTTTGAATTGGCGTTCATAAAAGGACAG

TTTTCAGAGGTGAACTCTTTGGGAATAAGTTATGCATGGGAAGCTTATCGAAAAGTAGAA

GGAGGCGCGGTGCAGCTTTTAGAAGCTGGGTTTGATTGGGAGGGAGCTCCAATGGATCTT

CCTAGACAGGAGCTGCGTGTCGCTCTGGAAAATAATACGGAATGGAGTTCTTACTTCAGC

ACAGTCTTAGGATTAACAGCTTTTGTGGAGGATTTACTTCTACAGATAGTAAACTAGGA

TATGAGGCGAATACTGGATTGCGATTGATCTTTTAA

Serovar L2 pmpD (SEQ ID NO.: 3)

ATGAGTTCCGAGAAAGATATAAAAAGCACCTGTTCTAAGTTTTCTTTGTCTGTAGTAGCA

GCTATCCTTGCCTCTGTTAGCGGGTTAGCTAGTTGCGTAGATCTTCATGCTGGAGGACAG

TCTGTAAATGAGCTGGTATATGTAGGCCCTCAAGCGGTTTTATTGTTAGACCAAATTCGA

GATCTATTCGTTGGGTCTAAAGATAGTCAGGCTGAAGGACAGTATAGGTTAATTGTAGGA

GATCCAAGTTCTTTCCAAGAGAAAGATGCAGATACTCTTCCCGGGAAGGTAGAGCAAAGT

ACTTTGTTCTCAGTAACCAATCCCGTGGTTTTCCAAGGTGTGGACCAACAGGATCAAGTC

TCTTCCCAAGGGTTAATTTGTAGTTTTACGAGCAGCAACCTTGATTCTCCCCGTGACGGA

GAATCTTTTTTAGGTATTGCTTTTGTTGGGGATAGTAGTAAGGCTGGAATCACATTAACT

GACGTGAAAGCTTCTTTGTCTGGAGCGGCTTTATATTCTACAGAAGATCTTATCTTTGAA

AAGATTAAGGGTGGATTGGAATTTGCATCATGTTCTTCTCTAGAACAGGGGGGAGCTTGT

GCAGCTCAAAGTATTTTGATTCATGATTGTCAAGGATTGCAGGTTAAACACTGTACTACA

GCCGTGAATGCTGAGGGGTCTAGTGCGAATGATCATCTTGGATTTGGAGGAGGCGCTTTC

TTTGTTACGGGTTCTCTTTCTGGAGAGAAAAGTCTCTATATGCCTGCAGGAGATATGGTA

GTTGCGAATTGTGATGGGGCTATATCTTTTGAAGGAAACAGCGCGAACTTTGCTAATGGA

GGAGCGATTGCTGCCTCTGGGAAAGTGCTTTTTGTCGCTAATGATAAAAAGACTTCTTTT

ATAGAGAACCGAGCTTTGTCTGGAGGAGCGATTGCAGCCTCTTCTGATATTGCCTTTCAA

AACTGCGCAGAACTAGTTTTCAAAGGCAATTGTGCAATTGGAACAGAGGATAAAGGTTCT

TTAGGTGGAGGGGCTATATCTTCTCTAGGCACCGTTCTTTTGCAAGGGAATCACGGGATA

ACTTGTGATAAGAATGAGTCTGCTTCGCAAGGAGGCGCCATTTTTGGCAAAAATTGTCAG

ATTTCTGACAACGAGGGGCCAGTGGTTTTCAGAGATAGTACAGCTTGCTTAGGAGGAGGC

GCTATTGCAGCTCAAGAAATTGTTTCTATTCAGAACAATCAGGCTGGGATTTCCTTCGAG

GGAGGTAAGGCTAGTTTCGGAGGAGGTATTGCGTGTGGATCTTTTTCTTCCGCAGGCGGT

GCTTCTGTTTTAGGGACTATTGATATTTCGAAGAATTrAGGCGCGATTTCGTTCTCTCGT

ACTTTATGTACGACCTCAGATTTAGGACAAATGGAGTACCAGGGAGGAGGAGCTCTATTT

GGTGAAAATATTTCTCTTTCTGAGAATGCTGGTGTGCTCACCTTTAAAGACAACATTGTG

AAGACTTTTGCTTCGAATGGGAAAATTCTGGGAGGAGGAGCGATTTTAGCTACTGGTAAG

GTGGAAATTACCAATAATTCCGGAGGAATTTCTTTTACAGGAAATGCGAGAGCTCCACAA

GCTCTTCCAACTCAAGAGGAGTTTCCTTTATTCAGCAAAAAAGAAGGGCGACCACTCTCT

TCAGGATATTCTGGGGGAGGAGCGATTTTAGGAAGAGAAGTAGCTATTCTCCACAACGCT

GCAGTAGTATTTGAGCAAAATCGTTTGCAGTGCAGCGAAGAAGAAGCGACATTATTAGGT

TGTTGTGGAGGAGGCGCTGTTCATGGGATGGATAGCACTTCGATTGTTGGCAACTCTTCA

-continued

GTAAGATTTGGTAATAATTACGCAATGGGACAAGGAGTCTCAGGAGGAGCTCTTTTATCT

AAAACAGTGCAGTTAGCTGGAAATGGAAGCGTCGATTTTTCTCGAAATATTGCTAGTTTG

GGAGGAGGAGCTCTTCAAGCTTCTGAAGGAAATTGTGAGCTAGTTGATAACGGCTATGTG

CTATTCAGAGATAATCGAGGGAGGGTTTATGGGGGTGCTATTTCTTGCTTACGTGGAGAT

GTAGTCATTTCTGGAAACAAGGGTAGAGTTGAATTTAAAGACAACATAGCAACACGTCTT

TATGTGGAAGAAACTGTAGAAAAGGTTGAAGAGGTAGAGCCAGCTCCTGAGCAAAAAGAC

AATAATGAGCTTTCTTTCTTAGGGAGTGTAGAACAGAGTTTTATTACTGCAGCTAATCAA

GCTCTTTTCGCATCTGAAGATGGGGATTTATCACCTGAGTCATCCATTTCTTCTGAAGAA

CTTGCGAAAAGAAGAGAGTGTGCTGGAGGAGCTATTTTTGCAAAACGGGTTCGTATTGTA

GATAACCAAGAGGCCGTTGTATTCTCGAATAACTTCTCTGATATTTATGGCGGCGCCATT

TTTACAGGTTCTCTTCGAGAAGAGGATAAGTTAGATGGGCAAATCCCTGAAGTCTTGATC

TCAGGCAATGCAGGGGATGTTGTTTTTTCCGGAAATTCCTCGAAGCGTGATGAGCATCTT

CCTCATACAGGTGGGGGAGCCATTTGTACTCAAAATTTGACGATTTCTCAGAATACAGGG

AATGTTCTGTTTTATAACAACGTGGCCTGTTCGGGAGGAGCTGTTCGTATAGAGGATCAT

GGTAATGTTCTTTTAGAAGCTTTTGGAGGAGATATTGTTTTTAAAGGAAATTCTTCTTTC

AGAGCACAAGGATCCGATGCTATCTATTTTGCAGGTAAAGAATCGCATATTACAGCCCTG

AATGCTACGGAAGGACATGCTATTGTTTTCCACGACGCATTAGTTTTTGAAAATCTAAAA

GAAAGGAAATCTGCTGAAGTATTGTTAATCAATAGTCGAGAAAATCCAGGTTACACTGGA

TCTATTCGATTTTTAGAAGCAGAAAGTAAAGTTCCTCAATGTATTCATGTACAACAAGGA

AGCCTTGAGTTGCTAAATGGAGCTACATTATGTAGTTATGGTTTTAAACAAGATGCTGGA

GCTAAGTTGGTATTGGCTGCTGGATCTAAACTGAAGATTTTAGATTCAGGAACTCCTGTA

CAAGGGCATGCTATCAGTAAACCTGAAGCAGAAATCGAGTCATCTTCTGAACCAGAGGGT

GCACATTCTCTTTGGATTGCGAAGAATGCTCAAACAACAGTTCCTATGGTTGATATCCAT

ACTATTTCTGTAGATTTAGCCTCCTTCTCTTCTAGTCAACAGGAGGGGACAGTAGAAGCT

CCTCAGGTTATTGTTCCTGGAGGAAGTTATGTTCGATCTGGAGAGCTTAATTTGGAGTTA

GTTAACACAACAGGTACTGGTTATGAAAATCATGCTTTGTTGAAGAATGAGGCTAAAGTT

CCATTGATGTCTTTCGTTGCTTCTAGTGATGAAGCTTCAGCCGAAATCAGTAACTTGTCG

GTTTCTGATTTACAGATTCATGTAGCAACTCCAGAGATTGAAGAAGACACATACGGCCAT

ATGGGAGATTGGTCTGAGGCTAAAATTCAAGATGGAACTCTTGTCATTAATTGGAATCCT

ACTGGATATCGATTAGATCCTCAAAAAGCAGGGGCTTTAGTATTTAATGCATTATGGGAA

GAAGGGGCTGTCTTGTCTGCTCTGAAAAATGCACGCTTTGCTCATAATCTCACTGCTCAG

CGTATGGAATTCGATTATTCTACAAATGTGTGGGGATTCGCCTTTGGTGGTTTCCGAACT

CTATCTGCAGAGAATCTGGTTGCTATTGATGGATACAAAGGAGCTTATGGTGGTGCTTCT

GCTGGAGTCGATATTCAATTGATGGAAGATTTTGTTCTAGGAGTTAGTGGAGCTGCTTTC

CTAGGTAAAATGGATAGTCAGAAGTTTGATGCGGAGGTTTCTCGGAAGGGAGTTGTTGGT

TCTGTATATACAGGATTTTTAGCTGGATCCTGGTTCTTCAAAGGACAATATAGCCTTGGA

GAAACACAGAACGATATGAAAACGCGTTATGGAGTACTAGGAGAGTCGAGTGCTTCTTGG

ACATCTCGAGGAGTACTGGCAGATGCTTTAGTTGAATACCGAAGTTTAGTTGGTCCTGTG

AGACCTACTTTTTATGCTTTGCATTTCAATCCTTATGTCGAAGTATCTTATGCTTCTATG

AAATTCCCTGGCTTTACAGAACAAGGAAGAGAAGCGCGTTCTTTTGAAGACGCTTCCCTT

-continued

ACCAATATCACCATTCCTTTAGGGATGAAGTTTGAATTGGCGTTCATAAAAGGACAGTTT

TCAGAGGTGAACTCTTTGGGAATAAGTTATGCATGGGAAGCTTATCGAAAAGTAGAAGGA

GGCGCGGTGCAGCTTTTAGAAGCTGGGTTTGATTGGGAGGGAGCTCCAATGGATCTTCCT

AGACAGGAGCTGCGTGTCGCTCTGGAAAATAATACGGAATGGAGTTCTTACTTCAGCACA

GTCTTAGGATTAACAGCTTTTTGTGGAGGATTTACTTCTACAGATAGTAAACTAGGATAT

GAGGCGAATGCTGGATTGCGATTGATCTTTTAA

Serovar A PmpD (SEQ ID NO.: 4)

MSSEKDIKSTCSKFSLSVVAAILASVSGLASCVDLHAGGQSVNELVYVGPQAVLLLDQIR

DLFVGSKDSQAEGQYRLIVGDPSSFQEKDADTLPGKVEQSTLFSVTNPVVFQGVDQQDQV

SSQGLICSFTSSNLDSPRDGESFLGIAFVGDSSKAGITLTDVKASLSGAALYSTEDLIFE

KIKGGLEFASCSSLEQGGACAAQSILIHDCQGLQVKHCTTAVNAEGSSANDHLGFGGGAF

FVTGSLSGEKSLYMPAGDMVVANCDGAISFEGNSANFANGGAIAASGKVLFVANDKKTSF

IENRALSGGAIAASSDIAFQNCAELVFKGNCAIGTEDKGSLGGGAISSLGTVLLQGNHGI

TCDKNESASQGGAIFGKNCQISDNEGPVVFRDSTACLGGGAIAAQEIVSIQNNQAGISFE

GGKASFGGGIACGSFSSAGGASVLGTIDISKNLGAISFSRTLCTTSDLGQMEYQGGGALF

GENISLSENAGVLTFKDNIVKTFASNGKILGGGAILATGKVEITNNSEGISFTGNARAPQ

ALPTQEEFPLFSKKEGRPLSSGYSGGGAILGREVAILHNAAVVFEQNRLQCSEEEATLLG

CCGGGAVHGMDSTSIVGNSSVRFGNNYAMGQGVSGGALLSKTVQLAGNGSVDFSRNIASL

GGGALQASEGNCELVDNGYVLFRDNRGRVYGGAISCLRGDVVISGNKGRVEFKDNIATRL

YVEETVEKVEEVEPAPEQKDNNELSFLGSAEQSFITAANQALFASEDGDLSPESSISSEE

LVKRRECAGGAIFAKRVRIVDNQEAVVFSNNFSDIYGGAIFTGSLREEDKLDGQIPEVLI

SGNAGDVVFSGNSSKRDEHLPHTGGGAICTQNLTISQNTGNVLFYNNVACSGGAVRIEDH

GNVLLEAFGGDIVFKGNSSFRAQGSDAIYFAGKESHITALNATEGHAIVFHDALVFENLE

ERKSAEVLLINSRENPGYTGSIRFLEAESKVPQCIHVQQGSLELLNGATLCSYGFKQDAG

AKLVLAAGAKLKILDSGTPVQQGHAISKPEAEIESSSEPEGAHSLWIAKNAQTTVPMVDI

HTISVDLASFSSSQQEGTVEAPQVIVPGGSYVRSGELNLELVNTTGTGYENHALLKNEAK

VPLMSFVASGDEASAEISNLSVSDLQIHVVTPEIEEDTYGHMGDWSEAKIQDGTLVISWN

PTGYRLDPQKAGALVFNALWEEGAVLSALKNARFAHNLTAQRMEFDYSTNVWGFAFGGFR

TLSAENLVAIDGYKGAYGGASAGVDIQLMEDFVLGVSGAAFLGKMDSQKFDAEVSRKGVV

GSVYTGFLAGSWFFKGQYSLGETQNDMKTRYGVLGESSASWTSRGVLADALVEYRSLVGP

VRPTFYALHFNPYVEVSYASMKFPGFTEQGREARSFEDASLTNITIPLGMKFELAFIKGQ

FSEVNSLGISYAWEAYRKVEGGAVQLLEAGFDWEGAPMDLPRQELRVALENNTEWSSYFS

TVLGLTAFCGGFTSTDSKLGYKANTGLRLIF

Serovar D PmpD (SEQ ID NO.: 5)

MSSEKDIKSTCSKFSLSVVAAILASVSGLASCVDLHAGGQSVNELVYVGPQAVLLLDQIR

DLFVGSKDSQAEGQYRLIVGDPSSFQEKDADTLPGKVEQSTLFSVTNPVVFQGVDQQDQV

SSQGLICSFTSSNLDSPRDGESFLGIAFVGDSSKAGITLTDVKASLSGAALYSTEDLIFE

KIKGGLEFASCSSLEQGGACAAQSILIHDCQGLQVKHCTTAVNAEGSSANDHLGFGGGAF

FVTGSLSGEKSLYMPAGDMVVANCDGAISFEGNSANFANGGAIAASGKVLFVANDKKTSF

IENRALSGGAIAASSDIAFQNCAELVFKGNCAIGTEDKGSLGGGAISSLGTVLLQGNHGI

TCDKNESASQGGAIFGKNCQISDNEGPVVFRDSTACLGGGAIAAQEIVSIQNNQAGISFE

-continued

GGKASFGGGIACGSFSSAGGASVLGTIDISKNLGAISFSRTLCTTSDLGQMEYQGGGALF

GENISLSENAGVLTFKDNIVKTFASNGKILGGGAILATGKVEITNNSEGISFTGNARAPQ

ALPTQEEFPLFSKKEGRPLSSGYSGGGAILGREVAILHNAAVVFEQNRLQCSEEEATLLG

CCGGGAVHGMDSTSIVGNSSVRFGNNYAMGQGVSGGALLSKTVQLAGNGSVDFSRNIASL

GGGALQASEGNCELVDNGYVLFRDNRGRVYGGAISCLRGDVVISGNKGRVEFKDNIATRL

YVEETVEKVEEVEPAPEQKDNNELSFLGRAEQSFITAANQALFASEDGDLSPESSISSEE

LAKRRECAGGAIFAKRVRIVDNQEAVVFSNNFSDIYGGAIFTGSLREEDKLDGQIPEVLI

SGNAGDVVFSGNSSKRDEHLPHTGGGAICTQNLTISQNTGNVLFYNNVACSGGAVRIEDH

GNVLLEAFGGDIVFKGNSSFRAQGSDAIYFAGKESHITALNATEGHAIVFHDALVFENLE

ERKSAEVLLINSRENPGYTGSIRFLEAESKVPQCIHVQQGSLELLNGATLCSYGFKQDAG

AKLVLAAGAKLKILDSGTPVQQGHAISKPEAEIESSSEPEGAHSLWIAKNAQTTVPMVDI

HTISVDLASFSSSQQEGTVEAPQVIVPGGSYVRSGELNLELVNTTGTGYENHALLKNEAK

VPLMSFVASGDEASAEISNLSVSDLQIHVVTPEIEEDTYGHMGDWSEAKIQDGTLVISWN

PTGYRLDPQKAGALVFNALWEEGAVLSALKNARFAHNLTAQRMEFDYSTNVWGFAFGGFR

TLSAENLVAIDGYKGAYGGASAGVDIQLMEDFVLGVSGAAFLGKMDSQKFDAEVSRKGVV

GSVYTGFLAGSWFFKGQYSLGETQNDMKTRYGVLGESSASWTSRGVLADALVEYRSLVGP

VRPTFYALHFNPYVEVSYASMKFPGFTEQGREARSFEDASLTNITIPLGMKFELAFIKGQ

FSEVNSLGISYAWEAYRKVEGGAVQLLEAGFDWEGAPMDLPRQELRVALENNTEWSSYFS

TVLGLTAFCGGFTSTDSKLGYEANTGLRLIF

Serovar L2 PmpD (SEQ ID NO.: 6)

MSSEKDIKSTCSKFSLSVVAAILASVSGLASCVDLHAGGQSVNELVYVGPQAVLLLDQIR

DLFVGSKDSQAEGQYRLIVGDPSSFQEKDADTLPGKVEQSTLFSVTNPVVFQGVDQQDQV

SSQGLICSFTSSNLDSPRDGESFLGIAFVGDSSKAGITLTDVKASLSGAALYSTEDLIFE

KIKGGLEFASCSSLEQGGACAAQSILIHDCQGLQVKHCTTAVNAEGSSANDHLGFGGGAF

FVTGSLSGEKSLYMPAGDMVVANCDGAISFEGNSANFANGGAIAASGKVLFVANDKKTSF

IENRALSGGAIAASSDIAFQNCAELVFKGNCAIGTEDKGSLGGGAISSLGTVLLQGNHGI

TCDKNESASQGGAIFGKNCQISDNEGPVVFRDSTACLGGGAIAAQEIVSIQNNQAGISFE

GGKASFGGGIACGSFSSAGGASVLGTIDISKNLGAISFSRTLCTTSDLGQMEYQGGGALF

GENISLSENAGVLTFKDNIVKTFASNGKILGGGAILATGKVEITNNSGGISFTGNARAPQ

ALPTQEEFPLFSKKEGRPLSSGYSGGGAILGREVAILHNAAVVFEQNRLQCSEEEATLLG

CCGGGAVHGMDSTSIVGNSSVRFGNNYAMGQGVSGGALLSKTVQLAGNGSVDFSRNIASL

GGGALQASEGNCELVDNGYVLFRDNRGRVYGGAISCLRGDVVISGNKGRVEFKDNIATRL

YVEETVEKVEEVEPAPEQKDNNELSFLGSVEQSFITAANQALFASEDGDLSPESSISSEE

LAKRRECAGGAIFAKRVRIVDNQEAVVFSNNFSDIYGGAIFTGSLREEDKLDGQIPEVLI

SGNAGDVVFSGNSSKRDEHLPHTGGGAICTQNLTISQNTGNVLFYNNVACSGGAVRIEDH

GNVLLEAFGGDIVFKGNSSFRAQGSDAIYFAGKESHITALNATEGHAIVFHDALVFENLK

ERKSAEVLLINSRENPGYTGSIRFLEAESKVPQCIHVQQGSLELLNGATLCSYGFKQDAG

AKLVLAAGSKLKILDSGTPVQGHAISKPEAEIESSSEPEGAHSLWIAKNAQTTVPMVDIH

TISVDLASFSSSQQEGTVEAPQVIVPGGSYVRSGELNLELVNTTGTGYENHALLKNEAKV

PLMSFVASSDEASAEISNLSVSDLQIHVATPEIEEDTYGHMGDWSEAKIQDGTLVINWNP

-continued

TGYRLDPQKAGALVFNALWEEGAVLSALKNARFAHNLTAQRMEFDYSTNVWGFAFGGFRT

LSAENLVAIDGYKGAYGGASAGVDIQLMEDFVLGVSGAAFLGKMDSQKFDAEVSRKGVVG

SVYTGFLAGSWFFKGQYSLGETQNDMKTRYGVLGESSASWTSRGVLADALVEYRSLVGPV

RPTFYALHFNPYVEVSYASMKFPGFTEQGREARSFEDASLTNITIPLGMKFELAFIKGQF

SEVNSLGISYAWEAYRKVEGGAVQLLEAGFDWEGAPMDLPRQELRVALENNTEWSSYFST

VLGLTAFCGGFTSTDSKLGYEANAGLRLIF (Sequences above In bold are the passenger domain and without wishing to be bound by any scientific theory are more likely to be Immunogenic).

Passenger domain of Serovar A PmpD (SEQ ID NO.: 7)

SGLASCVDLHAGGQSVNELVYVGPQAVLLLDQIR

DLFVGSKDSQAEGQYRLIVGDPSSFQEKDADTLPGKVEQSTLFSVTNPVVFQGVDQQDQV

SSQGLICSFTSSNLDSPRDGESFLGIAFVGDSSKAGITLTDVKASLSGAALYSTEDLIFE

KIKGGLEFASCSSLEQGGACAAQSILIHDCQGLQVKHCTTAVNAEGSSANDHLGFGGGAF

FVTGSLSGEKSLYMPAGDMVVANCDGAISFEGNSANFANGGAIAASGKVLFVANDKKTSF

IENRALSGGAIAASSDIAFQNCAELVFKGNCAIGTEDKGSLGGGAISSLGTVLLQGNHGI

TCDKNESASQGGAIFGKNCQISDNEGPVVFRDSTACLGGGAIAAQEIVSIQNNQAGISFE

GGKASFGGGIACGSFSSAGGASVLGTIDISKNLGAISFSRTLCTTSDLGQMEYQGGGALF

GENISLSENAGVLTFKDNIVKTFASNGKILGGGAILATGKVEITNNSEGISFTGNARAPQ

ALPTQEEFPLFSKKEGRPLSSGYSGGGAILGREVAILHNAAVVFEQNRLQCSEEEATLLG

CCGGGAVHGMDSTSIVGNSSVRFGNNYAMGQGVSGGALLSKTVQLAGNGSVDFSRNIASL

GGGALQASEGNCELVDNGYVLFRDNRGRVYGGAISCLRGDVVISGNKGRVEFKDNIATRL

YVEETVEKVEEVEPAPEQKDNNELSFLGSAEQSFITAANQALFASEDGDLSPESSISSEE

LVKRRECAGGAIFAKRVRIVDNQEAVVFSNNFSDIYGGAIFTGSLREEDKLDGQIPEVLI

SGNAGDVVFSGNSSKRDEHLPHTGGGAICTQNLTISQNTGNVLFYNNVACSGGAVRIEDH

GNVLLEAFGGDIVFKGNSSFRAQGSDAIYFAGKESHITALNATEGHAIVFHDALVFENLE

ERKSAEVLLINSRENPGYTGSIRFLEAESKVPQCIHVQQGSLELLNGATLCSYGFKQDAG

AKLVLAAGAKLKILDSGTPVQQGHAISKPEAEIESSSEPEGA

Passenger domain of Serovar D PmpD (SEQ ID NO.: 8)

SCVDLHAGGQSVNELVYVGPQAVLLLDQIR

DLFVGSKDSQAEGQYRLIVGDPSSFQEKDADTLPGKVEQSTLFSVTNPVVFQGVDQQDQV

SSQGLICSFTSSNLDSPRDGESFLGIAFVGDSSKAGITLTDVKASLSGAALYSTEDLIFE

KIKGGLEFASCSSLEQGGACAAQSILIHDCQGLQVKHCTTAVNAEGSSANDHLGFGGGAF

FVTGSLSGEKSLYMPAGDMVVANCDGAISFEGNSANFANGGAIAASGKVLFVANDKKTSF

IENRALSGGAIAASSDIAFQNCAELVFKGNCAIGTEDKGSLGGGAISSLGTVLLQGNHGI

TCDKNESASQGGAIFGKNCQISDNEGPVVFRDSTACLGGGAIAAQEIVSIQNNQAGISFE

GGKASFGGGIACGSFSSAGGASVLGTIDISKNLGAISFSRTLCTTSDLGQMEYQGGGALF

GENISLSENAGVLTFKDNIVKTFASNGKILGGGAILATGKVEITNNSEGISFTGNARAPQ

ALPTQEEFPLFSKKEGRPLSSGYSGGGAILGREVAILHNAAVVFEQNRLQCSEEEATLLG

CCGGGAVHGMDSTSIVGNSSVRFGNNYAMGQGVSGGALLSKTVQLAGNGSVDFSRNIASL

GGGALQASEGNCELVDNGYVLFRDNRGRVYGGAISCLRGDVVISGNKGRVEFKDNIATRL

YVEETVEKVEEVEPAPEQKDNNELSFLGRAEQSFITAANQALFASEDGDLSPESSISSEE

-continued

LAKRRECAGGAIFAKRVRIVDNQEAVVFSNNFSDIYGGAIFTGSLREEDKLDGQIPEVLI

SGNAGDVVFSGNSSKRDEHLPHTGGGAICTQNLTISQNTGNVLFYNNVACSGGAVRIEDH

GNVLLEAFGGDIVFKGNSSFRAQGSDAIYFAGKESHITALNATEGHAIVFHDALVFENLE

ERKSAEVLLINSRENPGYTGSIRFLEAESKVPQCIHVQQGSLELLNGATLCSYGFKQDAG

AKLVLAAGAKLKILDSGTPVQQGHAISKPEAEIESSSEPEGA

Passenger domain of Serovar L2 PmpD (SEQ ID NO.: 9)

SCVDLHAGGQSVNELVYVGPQAVLLLDQIR

DLFVGSKDSQAEGQYRLIVGDPSSFQEKDADTLPGKVEQSTLFSVTNPVVFQGVDQQDQV

SSQGLICSFTSSNLDSPRDGESFLGIAFVGDSSKAGITLTDVKASLSGAALYSTEDLIFE

KIKGGLEFASCSSLEQGGACAAQSILIHDCQGLQVKHCTTAVNAEGSSANDHLGFGGGAF

FVTGSLSGEKSLYMPAGDMVVANCDGAISFEGNSANFANGGAIAASGKVLFVANDKKTSF

IENRALSGGAIAASSDIAFQNCAELVFKGNCAIGTEDKGSLGGGAISSLGTVLLQGNHGI

TCDKNESASQGGAIFGKNCQISDNEGPVVFRDSTACLGGGAIAAQEIVSIQNNQAGISFE

GGKASFGGGIACGSFSSAGGASVLGTIDISKNLGAISFSRTLCTTSDLGQMEYQGGGALF

GENISLSENAGVLTFKDNIVKTFASNGKILGGGAILATGKVEITNNSGGISFTGNARAPQ

ALPTQEEFPLFSKKEGRPLSSGYSGGGAILGREVAILHNAAVVFEQNRLQCSEEEATLLG

CCGGGAVHGMDSTSIVGNSSVRFGNNYAMGQGVSGGALLSKTVQLAGNGSVDFSRNIASL

GGGALQASEGNCELVDNGYVLFRDNRGRVYGGAISCLRGDVVISGNKGRVEFKDNIATRL

YVEETVEKVEEVEPAPEQKDNNELSFLGSVEQSFITAANQALFASEDGDLSPESSISSEE

LAKRRECAGGAIFAKRVRIVDNQEAVVFSNNFSDIYGGAIFTGSLREEDKLDGQIPEVLI

SGNAGDVVFSGNSSKRDEHLPHTGGGAICTQNLTISQNTGNVLFYNNVACSGGAVRIEDH

GNVLLEAFGGDIVFKGNSSFRAQGSDAIYFAGKESHITALNATEGHAIVFHDALVFENLK

ERKSAEVLLINSRENPGYTGSIRFLEAESKVPQCIHVQQGSLELLNGATLCSYGFKQDAG

AKLVLAAGSKLKILDSGTPVQGHAISKPEAEIESSSEPEGA

Passenger domain of Serovar A pmpD (SEQ ID NO.: 10)

AGTTGCGTAGATCTTCATGCTGGAGGACAG

TCTGTAAATGAGCTGGTATATGTAGGCCCTCAAGCGGTTTTATTGTTAGACCAAATTCGA

GATCTATTCGTTGGGTCTAAAGATAGTCAGGCTGAAGGACAGTATAGGTTAATTGTAGGA

GATCCAAGTTCTTTCCAAGAGAAAGATGCGGATACTCTTCCCGGGAAGGTAGAGCAAAGT

ACTTTGTTCTCAGTAACCAATCCCGTGGTTTTCCAAGGTGTGGACCAACAGGATCAAGTC

TCTTCCCAAGGG1TAATTTGTAGTTTTACGAGCAGCAACCTTGATTCTCCTCGTGACGGA

GAATCTTTTTTAGGTATTGCTTTTGTTGGGGATAGTAGTAAGGCTGGAATCACATTAACT

GACGTGAAAGCTTCTTTGTCTGGAGCGGCTTTATATTCTACAGAAGATCTTATCTTTGAA

AAGATTAAGGGTGGATTGGAATTTGCATCATGTTCTTCTCTAGAACAGGGGGGAGCTTGT

GCAGCTCAAAGTATTTTGATTCATGATTGTCAAGGATTGCAGGTTAAACACTGTACTACA

GCCGTGAATGCTGAGGGGTCTAGTGCGAATGATCATCTTGGATTTGGAGGAGGCGCTTTC

TTTGTTACGGGTTCTCTTTCTGGAGAGAAAAGTCTCTATATGCCTGCAGGAGATATGGTA

GTTGCGAATTGTGATGGGGCTATATCTTTTGAAGGAAACAGCGCGAACTTTGCTAATGGA

GGAGCGATTGCTGCCTCTGGGAAAGTGLTTTTTGTCGCTAATGATAAAAAGACTTCTTTT

ATAGAGAACCGAGCTTTGTCTGGAGGAGCGATTGCAGCCTCTTCTGATATTGCCTTTCAA

-continued

AACTGCGCAGAACTAGTTTTCAAAGGCAATTGTGCAATTGGAACAGAGGATAAAGGTTCT

TTAGGTGGAGGGGCTATATCTTCTCTAGGCACCGTTCTTTTGCAAGGGAATCACGGGATA

ACTTGTGATAAGAATGAGTCTGCTTCGCAAGGAGGCGCCATTTTTGGCAAAAATTGTCAG

ATTTCTGACAACGAGGGGCCAGTGGTTTTCAGAGATAGTACAGCTTGCTTAGGAGGAGGC

GCTATTGCAGCTCAAGAAATTGTTTCTATTCAGAACAATCAGGCTGGGATTTCCTTCGAG

GGAGGTAAGGCTAGTTTCGGAGGAGGTATTGCGTGTGGATCTTTTTCTTCCGCAGGTGGT

GCTTCTGTTTTAGGGACCATTGATATTTCGAAGAATTTAGGCGCGATTTCGTTCTCTCGT

ACTTTATGTACGACCTCAGATTTAGGACAAATGGAGTACCAGGGAGGAGGAGCTCTATTT

GGTGAAAATATTTCTCTTTCTGAGAATGCTGGTGTGCTCACCTTTAAAGACAACATTGTG

AAGACTTTTGCTTCGAATGGGAAAATTCTGGGAGGAGGAGCGATTTTAGCTACTGGTAAG

GTGGAAATTACCAATAATTCCGAAGGAATTTCTTTTACAGGAAATGCGAGAGCTCCACAA

GCTCTTCCAACTCAAGAGGAGTTTCCTTTATTCAGCAAAAAAGAAGGGCGACCACTCTCT

TCAGGATATTCTGGGGGAGGAGCGATTTTAGGAAGAGAAGTAGCTATTCTCCACAACGCT

GCAGTAGTATTTGAGCAAAATCGTTTGCAGTGCAGCGAAGAAGAAGCGACATTATTAGGT

TGTTGTGGAGGAGGCGCTGTTCATGGGATGGATAGCACTTCGATTGTTGGCAACTCTTCA

GTAAGATTTGGTAATAATTACGCAATGGGACAAGGAGTCTCAGGAGGAGCTCTTTTATCT

AAAACAGTGCAGTTAGCTGGAAATGGAAGCGTCGATTTTTCTCGAAATATTGCTAGTTTG

GGAGGAGGAGCTCTTCAAGCTTCTGAAGGAAATTGTGAGCTAGTTGATAACGGCTATGTG

CTATTCAGAGATAATCGAGGGAGGGTTTATGGGGGTGCTATTTCTTGCTTACGTGGAGAT

GTAGTCATTTCTGGAAACAAGGGTAGAGTTGAATTTAAAGACAACATAGCAACACGTCTT

TATGTGGAAGAAACTGTAGAAAAGGTTGAAGAGGTAGAGCCAGCTCCTGAGCAAAAAGAC

AATAATGAGCTTTCTTTCTTAGGGAGTGCAGAACAGAGTTTTATTACTGCAGCTAATCAA

GCTCTTTTCGCATCTGAAGATGGGGATTTATCACCTGAGTCATCCATTTCTTCTGAAGAA

CTTGTGAAAAGAAGAGAGTGTGCTGGAGGAGCTATTTTTGCAAAAACGGGTTCGTATTGTA

GATAACCAAGAGGCCGTTGTATTCTCGAATAACTTCTCTGATATTTATGGCGGCGCCATT

TTTACAGGTTCTCTTCGAGAAGAGGATAAGTTAGATGGGCAAATCCCTGAAGTCTTGATC

TCAGGCAATGCAGGGGATG1TGTTTTTTCCGGAAATTCCTCGAAGCGTGATGAGCATCTT

CCTCATACAGGTGGGGGAGCCATTTGTACTCAAAATTTGACGATTTCTCAGAATACAGGG

AATGTTCTGTTTTATAACAACGTGGCCTGTTCGGGAGGAGCTGTTCGTATAGAGGATCAT

GGTAATGTTCTTTTAGAAGCTTTTGGAGGAGATATTGTTTTTAAAGGAAATTCTTCTTTC

AGAGCACAAGGATCCGATGCTATCTATTTTGCAGGTAAAGAATCGCATATTACAGCCCTG

AATGCTACGGAAGGACATGCTATTGTTTTCCACGACGCATTAGTTTTTGAAAATCTAGAA

GAAAGGAAATCTGCTGAAGTATTGTTAATCAATAGTCGAGAAAATCCAGGTTACACTGGA

TCTATTCGATTTTTAGAAGCAGAAAGTAAAGTTCCTCAATGTATTCATGTACAACAAGGA

AGCCTTGAGTTGCTAAATGGAGCCACATTATGTAGTTATGGTTTTAAACAAGATGCTGGA

GCTAAGTTGGTATTGGCTGCTGGAGCTAAACTGAAGATTTTAGATTCAGGAACTCCTGTA

CAACAAGGGCATGCTATCAGTAAACCTGAAGCAGAAATCGAGTCATCTTCTGAACCAGAG

GGTGCA

Passenger domain of Serovar D pmpD (SEQ ID NO.: 11)

AGTTGCGTAGATCTTCATGCTGGAGGACAG

TCTGTAAATGAGCTGGTATATGTAGGCCCTCAAGCGGTTTTATTGTTAGACCAAATTCGA

-continued

GATCTATTCGTTGGGTCTAAAGATAGTCAGGCTGAAGGACAGTATAGGTTAATTGTAGGA

GATCCAAGTTCTTTCCAAGAGAAAGATGCGGATACTCTTCCCGGGAAGGTAGAGCAAAGT

ACTTTGTTCTCAGTAACCAATCCCGTGGTTTTCCAAGGTGTGGACCAACAGGATCAAGTC

TCTTCCCAAGGGTTAATTTGTAGTTTTACGAGCAGCAACCTTGATTCTCCTCGTGACGGA

GAATCTTTTTTAGGTATTGCTTTTGTTGGGGATAGTAGTAAGGCTGGAATCACATTAACT

GACGTGAAAGCTTCTTTGTCTGGAGCGGCTTTATATTCTACAGAAGATCTTATCTTTGAA

AAGATTAAGGGTGGATTGGAATTTGCATCATGTTCTTCTCTAGAACAGGGGGGAGCTTGT

GCAGCTCAAAGTATTTTGATTCATGATTGTCAAGGATTGCAGGTTAAACACTGTACTACA

GCCGTGAATGCTGAGGGGTCTAGTGCGAATGATCATCTTGGATTTGGAGGAGGCGCTTTC

TTTGTTACGGGTTCTCTTTCTGGAGAGAAAAGTCTCTATATGCCTGCAGGAGATATGGTA

GTTGCGAATTGTGATGGGGCTATATCTTTTGAAGGAAACAGCGCGAACTTTGCTAATGGA

GGAGCGATTGCTGCCTCTGGGAAAGTGCTTTTTGTCGCTAATGATAAAAAGACTTCTTTT

ATAGAGAACCGAGCTTTGTCTGGAGGAGCGATTGCAGCCTCTTCTGATATTGCCTTTCAA

AACTGCGCAGAACTAGTTTTCAAAGGCAATTGTGCAATTGGAACAGAGGATAAAGGTTCT

TTAGGTGGAGGGGCTATATCTTCTCTAGGCACCGTTCTTTTGCAAGGGAATCACGGGATA

ACTTGTGATAAGAATGAGTCTGCTTCGCAAGGAGGCGCCATTTTTGGCAAAAATTGTCAG

ATTTCTGACAACGAGGGGCCAGTGGTTTTCAGAGATAGTACAGCTTGCTTAGGAGGAGGC

GCTATTGCAGCTCAAGAAATTGTTTCTATTCAGAACAATCAGGCTGGGATTTCCTTCGAG

GGAGGTAAGGCTAGTTTCGGAGGAGGTATTGCGTGTGGATCTTTTTCTTCCGCAGGTGGT

GCTTCTGTTTTAGGGACCATTGATATTTCGAAGAATTTAGGCGCGATTTCGTTCTCTCGT

ACTTTATGTACGACCTCAGATTTAGGACAAATGGAGTACCAGGGAGGAGGAGCTCTATTT

GGTGAAAATATTTCTCTTTCTGAGAATGCTGGTGTGCTCACCTTTAAAGACAACATTGTG

AAGACTTTTGCTTCGAATGGGAAAATTCTGGGAGGAGGAGCGATTTTAGCTACTGGTAAG

GTGGAAATTACTAATAATTCCGAAGGAATTTCTTTTACAGGAAATGCGAGAGCTCCACAA

GCTCTTCCAACTCAAGAGGAGTTTCCTTTATTCAGCAAAAAAGAAGGGCGACCACTCTCT

TCAGGATATTCTGGGGGAGGAGCGATTTTAGGAAGAGAAGTAGCTATTCTCCACAACGCT

GCAGTAGTATTTGAGCAAAATCGTTTGCAGTGCAGCGAAGAAGAAGCGACATTATTAGGT

TGTTGTGGAGGAGGCGCTGTTCATGGGATGGATAGGACTTCGATTGTTGGCAACTCTTCA

GTAAGATTTGGTAATAATTACGCAATGGGACAAGGAGTCTCAGGAGGAGCTCTTTTATCT

AAAACAGTGCAGTTAGCTGGGAATGGAAGCGTCGATTTTTCTCGAAATATTGCTAGTTTG

GGAGGAGGAGCTCTTCAAGCTTCTGAAGGAAATTGTGAGCTAGTTGATAACGGCTATGTG

CTATTCAGAGATAATCGAGGGAGGGTTTATGGGGGTGCTATTTCTTGCTTACGTGGAGAT

GTAGTCATTTCTGGAAACAAGGGTAGAGTTGAATTTAAAGACAACATAGCAACACGTCTT

TATGTGGAAGAAACTGTAGAAAAGGTTGAAGAGGTAGAGCCAGCTCCTGAGCAAAAAGAC

AATAATGAGGTTTCTTTCTTAGGGAGAGCAGAACAGAGTTTTATTACTGCAGCTAATCAA

GCTCTTTTCGCATCTGAAGATGGGGATTTATCACCTGAGTCATCCATTTCTTCTGAAGAA

CTTGCGAAAAGAAGAGAGTGTGCTGGAGGAGCTATTTTTGCAAAACGGGTTCGTATTGTA

GATAACCAAGAGGCCGTTGTATTCTCGAATAACTTCTCTGATATTTATGGCGGCGCCATT

TTTACAGGTTCTCTTCGAGAAGAGGATAAGTTAGATGGGCAAATCCCTGAAGTCTTGATC

TCAGGCAATGCAGGGGATGTTGTTTTTTCCGGAAATTCCTCGAAGCGTGATGAGCATCTT

-continued
CCTCATACAGGTGGGGGAGCCATTTGTACTCAAAATTTGACGATTTCTCAGAATACAGGG

AATGTTCTGTTTTATAACAACGTGGCCTGTTCGGGAGGAGCTGTTCGTATAGAGGATCAT

GGTAATGTTCTTTTAGAAGCTTTTGGAGGAGATATTGTTTTTAAAGGAAATTCTTCTTTC

AGAGCACAAGGATCCGATGCTATCTATTTTGCAGGTAAAGAATCGCATATTACAGCCCTG

AATGCTACGGAAGGACATGCTATTGTTTTCCACGACGCATTAGTTTTTGAAAATCTAGAA

GAAAGGAAATCTGCTGAAGTATTGTTAATCAATAGTCGAGAAAATCCAGGTTACACTGGA

TCTATTCGATTTTTAGAAGCAGAAAGTAAAGTTCCTCAATGTATTCATGTACAACAAGGA

AGCCTTGAGTTGCTAAATGGAGCCACATTATGTAGTTATGGTTTTAAACAAGATGCTGGA

GCTAAGTTGGTATTGGCTGCTGGAGCTAAACTGAAGATTTTAGATTCAGGAACTCCTGTA

CAACAAGGGCATGCTATCAGTAAACCTGAAGCAGAAATCGAGTCATCTTCTGAACCAGAG

GGTGCA

Passenger domain of Serovar L2 pmpD (SEQ ID NO.: 12)

AGTTGCGTAGATCTTCATGCTGGAGGACAG

TCTGTAAATGAGCTGGTATATGTAGGCCCTCAAGCGGTTTTATTGTTAGACCAAATTCGA

GATCTATTCGTTGGGTCTAAAGATAGTCAGGCTGAAGGACAGTATAGGTTAATTGTAGGA

GATCCAAGTTCTTTCCAAGAGAAAGATGCAGATACTCTTCCCGGGAAGGTAGAGCAAAGT

ACTTTGTTCTCAGTAACCAATCCCGTGGTTTTCCAAGGTGTGGACCAACAGGATCAAGTC

TCTTCCCAAGGGTTAATTTGTAGTTTTACGAGCAGCAACCTTGATTCTCCCCGTGACGGA

GAATCTTTTTTAGGTATTGCTTTTGTTGGGGATAGTAGTAAGGCTGGAATCACATTAACT

GACGTGAAAGCTTCTTTGTCTGGAGCGGCTTTATATTCTACAGAAGATCTTATCTTTGAA

AAGATTAAGGGTGGATTGGAATTTGCATCATGTTCTTCTCTAGAACAGGGGGGAGCTTGT

GCAGCTCAAAGTATTTTGATTCATGATTGTCAAGGATTGCAGGTTAAACACTGTACTACA

GCCGTGAATGCTGAGGGGTCTAGTGCGAATGATCATCTTGGATTTGGAGGAGGCGCTTTC

TTTGTTACGGGTTCTCTTTCTGGAGAGAAAAGTCTCTATATGCCTGCAGGAGATATGGTA

GTTGCGAATTGTGATGGGGCTATATCTTTTGAAGGAAACAGCGCGAACTTTGCTAATGGA

GGAGCGATTGCTGCCTCTGGGAAAGTGCTTTTTGTCGCTAATGATAAAAAGACTTCTTTT

ATAGAGAACCGAGCTTTGTCTGGAGGAGCGATTGCAGCCTCTTCTGATATTGCCTTTCAA

AACTGCGCAGAACTAGTTTTCAAAGGCAATTGTGCAATTGGAACAGAGGATAAAGGTTCT

TTAGGTGGAGGGGCTATATCTTCTCTAGGCACCGTTCTTTTGCAAGGGAATCACGGGATA

ACTTGTGATAAGAATGAGTCTGCTTCGCAAGGAGGCGCCATTTTTGGCAAAAATTGTCAG

ATTTCTGACAACGAGGGGCCAGTGGTTTTCAGAGATAGTACAGCTTGCTTAGGAGGAGGC

GCTATTGCAGCTCAAGAAATTGTTTCTATTCAGAACAATCAGGCTGGGATTTCCTTCGAG

GGAGGTAAGGCTAGTTTCGGAGGAGGTATTGCGTGTGGATCTTTTTCTTCCGCAGGCGGT

GCTTCTGTTTTAGGGACTATTGATATTTCGAAGAATTTAGGCGCGATTTCGTTCTCTCGT

ACTTTATGTACGACCTCAGATTTAGGACAAATGGAGTACCAGGGAGGAGGAGCTCTATTT

GGTGAAAATATTTCTCTTTCTGAGAATGCTGGTGTGCTCACCTTTAAAGACAACATTGTG

AAGACTTTTGCTTCGAATGGGAAAATTCTGGGAGGAGGAGCGATTTTAGCTACTGGTAAG

GTGGAAATTACCAATAATTCCGGAGGAATTTCTTTTACAGGAAATGCGAGAGCTCCACAA

GCTCTTCCAACTCAAGAGGAGTTTCCTTTATTCAGCAAAAAAGAAGGGCGACCACTCTCT

TCAGGATATTCTGGGGGAGGAGCGATTTTAGGAAGAGAAGTAGCTATTCTCCACAACGCT

GCAGTAGTATTTGAGCAAAATCGTTTGCAGTGCAGCGAAGAAGAAGCGACATTATTAGGT

-continued

```
TGTTGTGGAGGAGGCGCTGTTCATGGGATGGATAGCACTTCGATTGTTGGCAACTCTTCA

GTAAGATTTGGTAATAATTACGCAATGGGACAAGGAGTCTCAGGAGGAGCTCTTTTATCT

AAAACAGTGCAGTTAGCTGGAAATGGAAGCGTCGATTTTTCTCGAAATATTGCTAGTTTG

GGAGGAGGAGCTCTTCAAGCTTCTGAAGGAAATTGTGAGCTAGTTGATAACGGCTATGTG

CTATTCAGAGATAATCGAGGGAGGGTTTATGGGGGTGCTATTTCTTGCTTACGTGGAGAT

GTAGTCATTTCTGGAAACAAGGGTAGAGTTGAATTTAAAGACAACATAGCAACACGTCTT

TATGTGGAAGAAACTGTAGAAAAGGTTGAAGAGGTAGAGCCAGCTCCTGAGCAAAAAGAC

AATAATGAGCTTTCTTTCTTAGGGAGTGTAGAACAGAGTTTTATTACTGCAGCTAATCAA

GCTCTTTTCGCATCTGAAGATGGGGATTTATCACCTGAGTCATCCATTTCTTCTGAAGAA

CTTGCGAAAAGAAGAGAGTGTGCTGGAGGAGCTATTTTTGCAAAACGGGTTCGTATTGTA

GATAACCAAGAGGCCGTTGTATTCTCGAATAACTTCTCTGATATTTATGGCGGCGCCATT

TTTACAGGTTCTCTTCGAGAAGAGGATAAGTTAGATGGGCAAATCCCTGAAGTCTTGATC

TCAGGCAATGCAGGGGATGTTGTTTTTTCCGGAAATTCCTCGAAGCGTGATGAGCATCTT

CCTCATACAGGTGGGGGAGCCATTTGTACTCAAAATTTGACGATTTCTCAGAATACAGGG

AATGTTCTGTTTTATAACAACGTGGCCTGTTCGGGAGGAGCTGTTCGTATAGAGGATCAT

GGTAATGTTCTTTTAGAAGCTTTTGGAGGAGATATTGTTTTTAAAGGAAATTCTTCTTTC

AGAGCACAAGGATCCGATGCTATCTATTTTGCAGGTAAAGAATCGCATATTACAGCCCTG

AATGCTACGGAAGGACATGCTATTGTTTTCCACGACGCATTAGTTTTTGAAAATCTAAAA

GAAAGGAAATCTGCTGAAGTATTGTTAATCAATAGTCGAGAAAATCCAGGTTACACTGGA

TCTATTCGATTTTTAGAAGCAGAAAGTAAAGTTCCTCAATGTATTCATGTACAACAAGGA

AGCCTTGAGTTGCTAAATGGAGCTACATTATGTAGTTATGGTTTTAAACAAGATGCTGGA

GCTAAGTTGGTATTGGCTGCTGGATCTAAACTGAAGATTTTAGATTCAGGAACTCCTGTA

CAAGGGCATGCTATCAGTAAACCTGAAGCAGAAATCGAGTCATCTTCTGAACCAGAGGGT

GCA
```

REFERENCES

The following documents are referenced above including by a corresponding number as listed below within parentheses.

1. Resnikoff, S., Pascolini, D., Etya'ale, D., Kocur, I., Pararajasegaram, R., Pokharel, G. P. & Mariotti, S. P. (2004) *Bull World Health Organ* 82, 844-851.
2. Whitcher, J. P., Srinivasan, M. & Upadhyay, M. P. (2001) *Bull World Health Organ* 79, 214-221.
3. WHO (2001) in *Global Prevalence and Incidence of Selected Curable Sexually Transmitted Infections: Overview and Estimates*, Geneva), pp. 1-43.
4. Westrom, L., Joesoef, R., Reynolds, G., Hagdu, A. & Thompson, S. E. (1992) *Sex. Transm. Dis.* 19, 185-192.
5. Plummer, F., Simonsen, J. N., Cameron, D. W., Ndinya-AchOla, J., Kreiss, J. K., Gakinya, M. N., Waiyaki, P., Cheang, M., Piot, P. & Ronald, A_ R. (1991) *J Infect Dis* 164, 1236-1237.
6. Anttila, T., Saikku, P., Koskela, P., Bloigu, A., Dillner, J., Ikaheimo, I., Jellum, E., Lehtinen, M., Lenner, P., Hakulinen, T., et al. (2001) *JAMA* 285, 47-51.
7. CDC (2002) in *Sexually Transmitted Disease Surveillance,* 2001, Atlanta, Ga.), pp. 1-20.
8. Igietseme, J. U., Black, C. M. & Caldwell, H. D. (2002) *Biodrugs* 16, 19-35.
9. Cotter, T. W., Meng, Q., Shen, Z. L., Zhang, Y. X., Su, H. & Caldwell, H. D. (1995) *Infect Immun* 63, 4704-4714.
10. Pal, S., Barnhart, K. M., Wei, Q., Abai, A. M., Peterson, E. M. & de la Maza, L. M. (1999) *Vaccine* 17, 459-465.
11. Pal, S., Theodor, I., Peterson, E. M. & de la Maza, L. M. (1997) *Infect Immun* 65, 3361-3369.
12. Su, H., Parnell, M. & Caldwell, H. D. (1995) *Vaccine* 13, 1023-1032.
13. Taylor, H. R., Whittum-Hudson, J., Schachter, J., Caldwell, H. D. & Prendergast, R. A. (1988) *Invest Ophthalmol Vis Sci* 29, 1847-1853.
14. Zhang, D., Yang, X., Berry, J., Shen, C., McClarty, G. & Brunham, R. C. (1997) *J Infect Dis* 176, 1035-1040.
15. Barron, A. L., White, H. J., Rank, R. G., Soloff, B. L. & Moses, E. B. (1981) *J Infect Dis* 143, 63-66.
16. Morrison, R. P. & Caldwell, H. D. (2002) *Infect Immun* 70, 2741-2751.
17. Branham, R. C., Kuo, C. C., Cles, L. & Holmes, K. K. (1983) *Infect Immun* 39, 1491-1494.
18. Su, H., Feilzer, K., Caldwell, H. D. & Morrison, R. P. (1997) *Infect Immun* 65, 1993-1999.
19. Moore, T., Ananaba, G. A., Bolier, J., Bowers, S., Belay, T., Eko, F. O. & Igietseme, J. U. (2002) *Immunology* 105, 213-221.
20. Caldwell, H. D. & Schachter, J. (1982) *Infect Immun* 35, 1024-1031.

21. Zhang, Y, X., Stewart, S., Joseph, T., Taylor, H. R. & Caldwell, H. D. (1987) *J Immunol* 138, 575-581.
22. Caldwell, H. D. & Perry, L. J. (1982) *Infect Immun* 38, 745-754.
23. Su, H. & Caldwell, H. D. (1991) *Infect Immun* 59, 2843-2845.
24. Batteiger, B. E., Rank, R. G., Bavoil, P. M. & Soderberg, L. S. (1993) *J Gen Microbiol* 139, 2965-2972.
25. Pal, S., Peterson, E. M. & de la Maza, L. M. (2004) in *Proceedings Fifth Meeting of the Europen Society for Chlamydia Research*, ed. Deak, J. (University of Szeged, Budapest, Hungary), pp. 394-397.
26. Grayston, J. T., Kim, K. S. W., Alexander, E. R. & Wang, S.-P. (1971) in *Trachoma and Related Disorders Caused by Chlamydial Agents*, ed. Nichols, R. L. (Excerpta Medica, Boston, Mass.), pp. 377-385.
27. Caldwell, H. D. & Kuo, C. C. (1977) *J Immunol* 118, 437-441.
28. Caldwell, H. D., Kuo, C. C. & Kenny, G. E. (1975) *J Immunol* 115, 969-975.
29. Caldwell, H. D., Kromhout, J. & Schachter, J. (1981) *Infect Immun* 31, 1161-1176.
30. Su, H., Watkins, N. G., Zhang, Y. X. & Caldwell, H. D. (1990) *Infect Immun* 58, 1017-1025.
31. Carlson, J. H., Porcella, S. F., McClarty, G. & Caldwell, H. D. (2005) *Infect Immun* 73, 6407-6418.
32. Stephens, R. S., Kalman, S., Lammel, C., Fan, J., Marathe, R., Aravind, L., Mitchell, W., Olinger, L., Tatusov, R. L., Zhao, Q., et al. (1998) *Science* 282, 754-759.
33. Wehrl, W., Brinkmann, V., Jungblut, P. R., Meyer, T. F. & Szczepek, A. J. (2004) *Mol Microbiol* 51, 319-334.
34. Kalman, S., Mitchell, W., Marathe, R., Lammel, C., Fan, J., Hyman, R. W., Olinger, L., Grimwood, J., Davis, R. W. & Stephens, R. S. (1999) *Nat Genet* 21, 385-389.
35. Read, T. D., Brunham, R. C., Shen, C., Gill, S. R, Heidelberg, J. F., White, O., Hickey, E. K., Peterson, J., Utterback, T., Berry, K., et al. (2000) *Nucleic Acids Res* 28, 1397-1406.
36. Read, T. D., Muers, G. S., Brunham, R. C., Nelson, W. C., Paulsen, I. T., Heidelberg, J. F., Holtzapple, E., Khouri, H., Federova, N. B., Carty, H. A., et al. (2003) *Nucleic Acids Res* 31, 2134-2147.
37. Byrne, G. I., Stephens, R. S., Ada, G., Caldwell, H. D., Su, H., Morrison, R. P., Van der Pol, B., Bavoil, B., Bobo, L. & Everson, S. (1993) *J Infect Dis* 168, 415-420.
38. Su, H., Spangrude, G. J. & Caldwell, H. D. (1991) *Infect Immun* 59, 3811-3814.
39. Scidmore, M. A., Rockey, D. D., Fischer, E. R., Heinzen, R. A. & Hackstadt, T. (1996) *Infect Immun* 64, 5366-5372.
40. Grimwood, J. & Stephens, R. S. (1999) *Microb Comp Genomics* 4, 187-201.
41. Henderson, I. R. & Lam, A. C. (2001) *Trends Microbiol* 9, 573-578.
42. Henderson, I. R., Navarro-Garcia, F. & Nataro, J. P. (1998) *Trends Microbiol* 6, 370-378.
43. Lindquist, E. & Stephens, R. (1998) in *Proceedings of the ninth international symposium on Human Chlamydial infection*, eds. Stephens, R., Byrne, G., Christiansen, G., Clarke, I., Grayston, J., Rank, R., Ridgway, G., Saikku, P., Schachter, J. & Stamm, W. (international *Chlamydia* Symposium, San Francisco), pp. 259-262.

What is claimed is:

1. An immunogenic composition for inducing neutralizing antibodies against *Chlamydia trachomatis* in a subject, comprising: (A) at least one isolated polypeptide comprising a passenger domain of PmpD of *Chlamydia trachomatis* and (B) an adjuvant in an immunostimulatory amount, wherein the polypeptide is in an amount effective for inducing a neutralizing antibody immune response in the subject, wherein the passenger domain of PmpD is from *Chlamydia trachomatis* serovar A and comprises the amino acid sequence of SEQ ID NOs: 4 or 7.

2. The immunogenic composition of claim 1, wherein the *Chlamydia trachomatis* in the subject is at least two serovars.

3. An immunogenic composition for inducing neutralizing antibodies against *Chlamydia trachomatis* in a subject, comprising: (A) at least one isolated polypeptide (1) comprising the amino acid sequence of SEQ ID NO: 6 or (2) consisting of the amino acid sequence of SEQ ID NO: 9 and (B) an adjuvant in an immunostimulatory amount, wherein the polypeptide is in an amount effective for inducing a neutralizing antibody immune response in the subject.

4. The immunogenic composition of claim 3, wherein the *Chlamydia trachomatis* in the subject is at least two serovars.

5. The immunogenic composition of claim 1, wherein the effective amount of the at least one isolated polypeptide comprising a passenger domain of PmpD of *Chlamydia trachomatis* compensates for the blocking effect of preexisting antibodies to immunodominant antigens MOMP and LPS.

6. The immunogenic composition of claim 3, wherein the effective amount of the at least one isolated polypeptide compensates for the blocking effect of preexisting antibodies to immunodominant antigens MOMP and LPS.

7. A method of inducing neutralizing antibodies against *Chlamydia trachomatis* in a subject by administering an immunologically effective amount of the immunogenic composition of claim 1.

8. The method of claim 7, wherein the administering step is performed after reducing or eliminating preexisting antibodies to immunodominant antigens MOMP and LPS.

9. A method of inducing neutralizing antibodies against *Chlamydia trachomatis* in a subject by administering an immunologically effective amount of the immunogenic composition of claim 3.

10. The method of claim 9, wherein the administering step is performed after reducing or eliminating preexisting antibodies to immunodominant antigens MOMP and LPS.

11. The immunogenic composition of claim 3, wherein the isolated polypeptide comprises the amino acid sequence of SEQ ID NO: 6.

12. The immunogenic composition of claim 3, wherein the isolated polypeptide consists of the amino acid sequence of SEQ ID NO: 9.

* * * * *

SEQUENCE LISTING

<160> NUMBER OF SEQ ID NOS: 12

<210> SEQ ID NO 1
<211> LENGTH: 4596
<212> TYPE: DNA
<213> ORGANISM: Chlamydia trachomatis

<400> SEQUENCE: 1

```
atgagttccg agaaagatat aaaaagcacc tgttctaagt tttctttatc tgtagtagca      60

gctatccttg cctctgttag cgggttagct agttgcgtag atcttcatgc tggaggacag     120

tctgtaaatg agctggtata tgtaggccct caagcggttt tattgttaga ccaaattcga     180

gatctattcg ttgggtctaa agatagtcag gctgaaggac agtataggtt aattgtagga     240

gatccaagtt ctttccaaga gaaagatgcg gatactcttc ccgggaaggt agagcaaagt     300

actttgttct cagtaaccaa tcccgtggtt ttccaaggtg tggaccaaca ggatcaagtc     360

tcttcccaag ggttaatttg tagttttacg agcagcaacc ttgattctcc tcgtgacgga     420

gaatcttttt taggtattgc ttttgttggg gatagtagta aggctggaat cacattaact     480

gacgtgaaag cttctttgtc tggagcggct ttatattcta cagaagatct tatctttgaa     540

aagattaagg gtggattgga atttgcatca tgttcttctc tagaacaggg gggagcttgt     600

gcagctcaaa gtattttgat tcatgattgt caaggattgc aggttaaaca ctgtactaca     660

gccgtgaatg ctgaggggtc tagtgcgaat gatcatcttg gatttggagg aggcgctttc     720

tttgttacgg gttctctttc tggagagaaa agtctctata tgcctgcagg agatatggta     780

gttgcgaatt gtgatggggc tatatctttt gaaggaaaca gcgcgaactt tgctaatgga     840

ggagcgattg ctgcctctgg gaaagtgctt tttgtcgcta atgataaaaa gacttctttt     900
```

-continued

```
atagagaacc gagctttgtc tggaggagcg attgcagcct cttctgatat tgcctttcaa    960
aactgcgcag aactagtttt caaaggcaat tgtgcaattg gaacagagga taaaggttct   1020
ttaggtggag ggctatatc ttctctaggc accgttcttt tgcaagggaa tcacgggata   1080
acttgtgata agaatgagtc tgcttcgcaa ggaggcgcca tttttggcaa aaattgtcag   1140
atttctgaca acgaggggcc agtggttttc agagatagta cagcttgctt aggaggaggc   1200
gctattgcag ctcaagaaat tgtttctatt cagaacaatc aggctgggat ttccttcgag   1260
ggaggtaagg ctagtttcgg aggaggtatt gcgtgtggat ctttttcttc cgcaggtggt   1320
gcttctgttt tagggaccat tgatatttcg aagaatttag gcgcgatttc gttctctcgt   1380
actttatgta cgacctcaga tttaggacaa atggagtacc agggaggagg agctctattt   1440
ggtgaaaata tttctctttc tgagaatgct ggtgtgctca cctttaaaga caacattgtg   1500
aagacttttg cttcgaatgg gaaaattctg ggaggaggag cgattttagc tactggtaag   1560
gtggaaatta ccaataattc cgaaggaatt tcttttacag gaaatgcgag agctccacaa   1620
gctcttccaa ctcaagagga gtttccttta ttcagcaaaa aagaagggcg accactctct   1680
tcaggatatt ctgggggagg agcgatttta ggaagagaag tagctattct ccacaacgct   1740
gcagtagtat ttgagcaaaa tcgtttgcag tgcagcgaag aagaagcgac attattaggt   1800
tgttgtggag gaggcgctgt tcatgggatg gatagcactt cgattgttgg caactcttca   1860
gtaagatttg gtaataatta cgcaatggga caaggagtct caggaggagc tcttttatct   1920
aaaacagtgc agttagctgg aaatggaagc gtcgattttt ctcgaaatat tgctagtttg   1980
ggaggaggag ctcttcaagc ttctgaagga aattgtgagc tagttgataa cggctatgtg   2040
ctattcagag ataatcgagg gagggtttat gggggtgcta tttcttgctt acgtggagat   2100
gtagtcattt ctggaaacaa gggtagagtt gaatttaaag acaacatagc aacacgtctt   2160
tatgtggaag aaactgtaga aaaggttgaa gaggtagagc cagctcctga gcaaaaagac   2220
aataatgagc tttctttctt agggagtgca gaacagagtt ttattactgc agctaatcaa   2280
gctcttttcg catctgaaga tggggattta tcacctgagt catccatttc ttctgaagaa   2340
cttgtgaaaa gaagagagtg tgctggagga gctatttttg caaaacgggt tcgtattgta   2400
gataaccaag aggccgttgt attctcgaat aacttctctg atatttatgg cggcgccatt   2460
tttacaggtt ctcttcgaga agaggataag ttagatgggc aaatccctga agtcttgatc   2520
tcaggcaatg caggggatgt tgtttttttcc ggaaattcct cgaagcgtga tgagcatctt   2580
cctcatacag gtgggggagc catttgtact caaaatttga cgatttctca gaatacaggg   2640
aatgttctgt tttataacaa cgtggcctgt tcgggaggag ctgttcgtat agaggatcat   2700
ggtaatgttc ttttagaagc ttttggagga gatattgttt ttaaaggaaa ttcttctttc   2760
agagcacaag gatccgatgc tatctatttt gcaggtaaag aatcgcatat tacagccctg   2820
aatgctacgg aaggacatgc tattgttttc cacgacgcat tagtttttga aaatctagaa   2880
gaaaggaaat ctgctgaagt attgttaatc aatagtcgag aaaatccagg ttacactgga   2940
tctattcgat tttagaagc agaaagtaaa gttcctcaat gtattcatgt acaacaagga   3000
agccttgagt tgctaaatgg agccacatta tgtagttatg gttttaaaca agatgctgga   3060
gctaagttgg tattggctgc tggagctaaa ctgaagattt tagattcagg aactcctgta   3120
caacaagggc atgctatcag taaacctgaa gcagaaatcg agtcatcttc tgaaccagag   3180
ggtgcacatt ctctttggat tgcgaagaat gctcaaacaa cagttcctat ggttgatatc   3240
```

-continued

```
catactattt ctgtagattt agcctccttc tcttctagtc aacaggaggg gacagtagaa   3300

gctcctcagg ttattgttcc tggaggaagt tatgttcgat ctggagagct taatttggag   3360

ttagttaaca caacaggtac tggttatgaa aatcatgctt tgttgaagaa tgaggctaaa   3420

gttccattga tgtctttcgt tgcttctggt gatgaagctt cagccgaaat cagtaacttg   3480

tcggtttctg atttacagat tcatgtagta actccagaga ttgaagaaga cacatacggc   3540

catatgggag attggtctga ggctaaaatt caagatggaa ctcttgtcat tagttggaat   3600

cctactggat atcgattaga tcctcaaaaa gcaggggctt tagtatttaa tgcattatgg   3660

gaagaagggg ctgtcttgtc tgctctgaaa aatgcacgct ttgctcataa tctcactgct   3720

cagcgtatgg aattcgatta ttctacaaat gtgtggggat tcgcctttgg tggtttccga   3780

actctatctg cagagaatct ggttgctatt gatggataca aaggagctta tggtggtgct   3840

tctgctggag tcgatattca attgatggaa gattttgttc taggagttag tggagctgct   3900

ttcctaggta aaatggatag tcagaagttt gatgcggagg tttctcggaa gggagttgtt   3960

ggttctgtat atacaggatt tttagctgga tcctggttct tcaaaggaca atatagcctt   4020

ggagaaacac agaacgatat gaaaacgcgt tatggagtac taggagagtc gagtgcttct   4080

tggacatctc gaggagtact ggcagatgct ttagttgaat accgaagttt agttggtcct   4140

gtgagaccta ctttttatgc tttgcatttc aatccttatg tcgaagtatc ttatgcttct   4200

atgaaattcc ctggctttac agaacaagga agagaagcgc gttcttttga agacgcttcc   4260

cttaccaata tcaccattcc tttagggatg aagtttgaat tggcgttcat aaaaggacag   4320

ttttcagagg tgaactcttt gggaataagt tatgcatggg aagcttatcg aaaagtagaa   4380

ggaggcgcgg tgcagctttt agaagctggg tttgattggg agggagctcc aatggatctt   4440

cctagacagg agctgcgtgt cgctctggaa aataatacgg aatggagttc ttacttcagc   4500

acagtcttag gattaacagc tttttgtgga ggatttactt ctacagatag taaactagga   4560

tataaggcga atactggatt gcgattgatc ttttaa                             4596

<210> SEQ ID NO 2
<211> LENGTH: 4596
<212> TYPE: DNA
<213> ORGANISM: Chlamydia trachomatis

<400> SEQUENCE: 2

atgagttccg agaaagatat aaaaagcacc tgttctaagt ttctctttgtc tgtagtagca     60

gctatccttg cctctgttag cgggttagct agttgcgtag atcttcatgc tggaggacag    120

tctgtaaatg agctggtata tgtaggccct caagcggttt tattgttaga ccaaattcga    180

gatctattcg ttgggtctaa agatagtcag gctgaaggac agtataggtt aattgtagga    240

gatccaagtt ctttccaaga gaaagatgcg gatactcttc ccgggaaggt agagcaaagt    300

actttgttct cagtaaccaa tcccgtggtt ttccaaggtg tggaccaaca ggatcaagtc    360

tcttcccaag ggttaatttg tagttttacg agcagcaacc ttgattctcc tcgtgacgga    420

gaatcttttt taggtattgc ttttgttggg gatagtagta aggctggaat cacattaact    480

gacgtgaaag cttctttgtc tggagcggct ttatattcta cagaagatct tatctttgaa    540

aagattaagg gtggattgga atttgcatca tgttcttctc tagaacaggg gggagcttgt    600

gcagctcaaa gtattttgat tcatgattgt caaggattgc aggttaaaca ctgtactaca    660

gccgtgaatg ctgaggggtc tagtgcgaat gatcatcttg gatttggagg aggcgctttc    720

tttgttacgg gttctctttc tggagagaaa agtctctata tgcctgcagg agatatggta    780
```

-continued

```
gttgcgaatt gtgatggggc tatatctttt gaaggaaaca gcgcgaactt tgctaatgga    840
ggagcgattg ctgcctctgg gaaagtgctt tttgtcgcta atgataaaaa gacttctttt    900
atagagaacc gagctttgtc tggaggagcg attgcagcct cttctgatat tgcctttcaa    960
aactgcgcag aactagtttt caaaggcaat tgtgcaattg gaacagagga taaaggttct   1020
ttaggtggag ggctatatc ttctctaggc accgttcttt tgcaagggaa tcacgggata   1080
acttgtgata agaatgagtc tgcttcgcaa ggaggcgcca tttttggcaa aaattgtcag   1140
atttctgaca acgagggggcc agtggttttc agagatagta cagcttgctt aggaggaggc   1200
gctattgcag ctcaagaaat tgtttctatt cagaacaatc aggctgggat ttccttcgag   1260
ggaggtaagg ctagtttcgg aggaggtatt gcgtgtggat ctttttcttc cgcaggtggt   1320
gcttctgttt tagggaccat tgatatttcg aagaatttag gcgcgatttc gttctctcgt   1380
actttatgta cgacctcaga tttaggacaa atggagtacc agggaggagg agctctattt   1440
ggtgaaaata tttctctttc tgagaatgct ggtgtgctca cctttaaaga caacattgtg   1500
aagacttttg cttcgaatgg gaaaattctg ggaggaggag cgattttagc tactggtaag   1560
gtggaaatta ctaataattc cgaaggaatt tcttttacag gaaatgcgag agctccacaa   1620
gctcttccaa ctcaagagga gtttccttta ttcagcaaaa aagaagggcg accactctct   1680
tcaggatatt ctgggggagg agcgatttta ggaagagaag tagctattct ccacaacgct   1740
gcagtagtat ttgagcaaaa tcgtttgcag tgcagcgaag aagaagcgac attattaggt   1800
tgttgtggag gaggcgctgt tcatgggatg gatagcactt cgattgttgg caactcttca   1860
gtaagatttg gtaataatta cgcaatggga caaggagtct caggaggagc tcttttatct   1920
aaaacagtgc agttagctgg gaatggaagc gtcgattttt ctcgaaatat tgctagtttg   1980
ggaggaggag ctcttcaagc ttctgaagga aattgtgagc tagttgataa cggctatgtg   2040
ctattcagag ataatcgagg gagggtttat gggggtgcta tttcttgctt acgtggagat   2100
gtagtcattt ctggaaacaa gggtagagtt gaatttaaag acaacatagc aacacgtctt   2160
tatgtggaag aaactgtaga aaaggttgaa gaggtagagc cagctcctga gcaaaaagac   2220
aataatgagc tttctttctt agggagagca gaacagagtt ttattactgc agctaatcaa   2280
gctcttttcg catctgaaga tggggattta tcacctgagt catccatttc ttctgaagaa   2340
cttgcgaaaa gaagagagtg tgctggagga gctatttttg caaaacgggt tcgtattgta   2400
gataaccaag aggccgttgt attctcgaat aacttctctg atatttatgg cggcgccatt   2460
tttacaggtt ctcttcgaga agaggataag ttagatgggc aaatccctga agtcttgatc   2520
tcaggcaatg caggggatgt tgttttttcc ggaaattcct cgaagcgtga tgagcatctt   2580
cctcatacag gtgggggagc catttgtact caaaatttga cgatttctca gaatacaggg   2640
aatgttctgt tttataacaa cgtggcctgt tcgggaggag ctgttcgtat agaggatcat   2700
ggtaatgttc ttttagaagc ttttggagga gatattgttt ttaaaggaaa ttcttctttc   2760
agagcacaag gatccgatgc tatctatttt gcaggtaaag aatcgcatat tacagccctg   2820
aatgctacgg aaggacatgc tattgttttc cacgacgcat tagtttttga aaatctagaa   2880
gaaaggaaat ctgctgaagt attgttaatc aatagtcgag aaaatccagg ttacactgga   2940
tctattcgat ttttagaagc agaaagtaaa gttcctcaat gtattcatgt acaacaagga   3000
agccttgagt tgctaaatgg agccacatta tgtagttatg gttttaaaca agatgctgga   3060
gctaagttgg tattggctgc tggagctaaa ctgaagattt tagattcagg aactcctgta   3120
```

-continued

```
caacaagggc atgctatcag taaacctgaa gcagaaatcg agtcatcttc tgaaccagag   3180
ggtgcacatt ctctttggat tgcgaagaat gctcaaacaa cagttcctat ggttgatatc   3240
catactattt ctgtagattt agcctccttc tcttctagtc aacaggaggg gacagtagaa   3300
gctcctcagg ttattgttcc tggaggaagt tatgttcgat ctggagagct taatttggag   3360
ttagttaaca caacaggtac tggttatgaa aatcatgctt tattgaagaa tgaggctaaa   3420
gttccattga tgtctttcgt tgcttctggt gatgaagctt cagccgaaat cagtaacttg   3480
tcggtttctg atttacagat tcatgtagta actccagaga ttgaagaaga cacatacggc   3540
catatgggag attggtctga ggctaaaatt caagatggaa ctcttgtcat tagttggaat   3600
cctactggat atcgattaga tcctcaaaaa gcaggggctt tagtatttaa tgcattatgg   3660
gaagaagggg ctgtcttgtc tgctctgaaa aatgcacgct ttgctcataa tctcactgct   3720
cagcgtatgg aattcgatta ttctacaaat gtgtggggat tcgcctttgg tggtttccga   3780
actctatctg cagagaatct ggttgctatt gatggataca aaggagctta tggtggtgct   3840
tctgctggag tcgatattca attgatggaa gatttttgttc taggagttag tggagctgct   3900
ttcctaggta aaatggatag tcagaagttt gatgcggagg tttctcggaa gggagttgtt   3960
ggttctgtat atacaggatt tttagctgga tcctggttct tcaaaggaca atatagcctt   4020
ggagaaacac agaacgatat gaaaacgcgt tatggagtac taggagagtc gagtgcttct   4080
tggacatctc gaggagtact ggcagatgct ttagttgaat accgaagttt agttggtcct   4140
gtgagaccta ctttttatgc tttgcatttc aatccttatg tcgaagtatc ttatgcttct   4200
atgaaattcc ctggctttac agaacaagga agagaagcgc gttcttttga agacgcttcc   4260
cttaccaata tcaccattcc tttagggatg aagtttgaat tggcgttcat aaaaggacag   4320
ttttcagagg tgaactcttt gggaataagt tatgcatggg aagcttatcg aaaagtagaa   4380
ggaggcgcgg tgcagctttt agaagctggg tttgattggg agggagctcc aatggatctt   4440
cctagacagg agctgcgtgt cgctctggaa aataatacgg aatggagttc ttacttcagc   4500
acagtcttag gattaacagc tttttgtgga ggatttactt ctacagatag taaactagga   4560
tatgaggcga atactggatt gcgattgatc ttttaa                             4596
```

<210> SEQ ID NO 3
<211> LENGTH: 4593
<212> TYPE: DNA
<213> ORGANISM: Chlamydia trachomatis

<400> SEQUENCE: 3

```
atgagttccg agaaagatat aaaaagcacc tgttctaagt tttctttgtc tgtagtagca     60
gctatccttg cctctgttag cgggttagct agttgcgtag atcttcatgc tggaggacag    120
tctgtaaatg agctggtata tgtaggccct caagcggttt tattgttaga ccaaattcga    180
gatctattcg ttgggtctaa agatagtcag gctgaaggac agtataggtt aattgtagga    240
gatccaagtt ctttccaaga gaaagatgca gatactcttc ccgggaaggt agagcaaagt    300
actttgttct cagtaaccaa tcccgtggtt ttccaaggtg tggaccaaca ggatcaagtc    360
tcttcccaag ggttaatttg tagttttacg agcagcaacc ttgattctcc ccgtgacgga    420
gaatcttttt taggtattgc ttttgttggg gatagtagta aggctggaat cacattaact    480
gacgtgaaag cttctttgtc tggagcggct ttatattcta cagaagatct tatctttgaa    540
aagattaagg gtggattgga atttgcatca tgttcttctc tagaacaggg gggagcttgt    600
gcagctcaaa gtattttgat tcatgattgt caaggattgc aggttaaaca ctgtactaca    660
```

-continued

```
gccgtgaatg ctgaggggtc tagtgcgaat gatcatcttg gatttggagg aggcgctttc    720
tttgttacgg gttctctttc tggagagaaa agtctctata tgcctgcagg agatatggta    780
gttgcgaatt gtgatggggc tatatctttt gaaggaaaca gcgcgaactt tgctaatgga    840
ggagcgattg ctgcctctgg gaaagtgctt tttgtcgcta atgataaaaa gacttctttt    900
atagagaacc gagctttgtc tggaggagcg attgcagcct cttctgatat tgcctttcaa    960
aactgcgcag aactagtttt caaaggcaat tgtgcaattg gaacagagga taaaggttct   1020
ttaggtggag gggctatatc ttctctaggc accgttcttt tgcaagggaa tcacgggata   1080
acttgtgata agaatgagtc tgcttcgcaa ggaggcgcca tttttggcaa aaattgtcag   1140
atttctgaca acgaggggcc agtggttttc agagatagta cagcttgctt aggaggaggc   1200
gctattgcag ctcaagaaat tgtttctatt cagaacaatc aggctgggat ttccttcgag   1260
ggaggtaagg ctagtttcgg aggaggtatt gcgtgtggat ctttttcttc cgcaggcggt   1320
gcttctgttt tagggactat tgatatttcg aagaatttag gcgcgatttc gttctctcgt   1380
actttatgta cgacctcaga tttaggacaa atggagtacc agggaggagg agctctattt   1440
ggtgaaaata tttctctttc tgagaatgct ggtgtgctca cctttaaaga caacattgtg   1500
aagacttttg cttcgaatgg gaaaattctg ggaggaggag cgattttagc tactggtaag   1560
gtggaaatta ccaataattc cggaggaatt tcttttacag gaaatgcgag agctccacaa   1620
gctcttccaa ctcaagagga gtttcctta ttcagcaaaa aagaagggcg accactctct   1680
tcaggatatt ctgggggagg agcgatttta ggaagagaag tagctattct ccacaacgct   1740
gcagtagtat ttgagcaaaa tcgtttgcag tgcagcgaag aagaagcgac attattaggt   1800
tgttgtggag gaggcgctgt tcatgggatg gatagcactt cgattgttgg caactcttca   1860
gtaagatttg gtaataatta cgcaatggga caaggagtct caggaggagc tcttttatct   1920
aaaacagtgc agttagctgg aaatggaagc gtcgattttt ctcgaaatat tgctagtttg   1980
ggaggaggag ctcttcaagc ttctgaagga aattgtgagc tagttgataa cggctatgtg   2040
ctattcagag ataatcgagg gagggtttat gggggtgcta tttcttgctt acgtggagat   2100
gtagtcattt ctggaaacaa gggtagagtt gaatttaaag acaacatagc aacacgtctt   2160
tatgtggaag aaactgtaga aaaggttgaa gaggtagagc cagctcctga gcaaaaagac   2220
aataatgagc tttctttctt agggagtgta gaacagagtt ttattactgc agctaatcaa   2280
gctcttttcg catctgaaga tggggattta tcacctgagt catccatttc ttctgaagaa   2340
cttgcgaaaa gaagagagtg tgctggagga gctatttttg caaaacgggt tcgtattgta   2400
gataaccaag aggccgttgt attctcgaat aacttctctg atatttatgg cggcgccatt   2460
tttacaggtt ctcttcgaga agaggataag ttagatgggc aaatccctga agtcttgatc   2520
tcaggcaatg caggggatgt tgtttttttcc ggaaattcct cgaagcgtga tgagcatctt   2580
cctcatacag gtgggggagc catttgtact caaaatttga cgatttctca gaatacaggg   2640
aatgttctgt tttataacaa cgtggcctgt tcgggaggag ctgttcgtat agaggatcat   2700
ggtaatgttc ttttagaagc ttttggagga gatattgttt ttaaaggaaa ttcttctttc   2760
agagcacaag gatccgatgc tatctatttt gcaggtaaag aatcgcatat tacagccctg   2820
aatgctacgg aaggacatgc tattgttttc cacgacgcat tagtttttga aaatctaaaa   2880
gaaaggaaat ctgctgaagt attgttaatc aatagtcgag aaaatccagg ttacactgga   2940
tctattcgat tttagaagc agaaagtaaa gttcctcaat gtattcatgt acaacaagga    3000
```

-continued agccttgagt tgctaaatgg agctacatta tgtagttatg gttttaaaca agatgctgga 3060
gctaagttgg tattggctgc tggatctaaa ctgaagattt tagattcagg aactcctgta 3120
caagggcatg ctatcagtaa acctgaagca gaaatcgagt catcttctga accagagggt 3180
gcacattctc tttggattgc gaagaatgct caaacaacag ttcctatggt tgatatccat 3240
actatttctg tagatttagc ctccttctct tctagtcaac aggaggggac agtagaagct 3300
cctcaggtta ttgttcctgg aggaagttat gttcgatctg gagagcttaa tttggagtta 3360
gttaacacaa caggtactgg ttatgaaaat catgctttgt tgaagaatga ggctaaagtt 3420
ccattgatgt ctttcgttgc ttctagtgat gaagcttcag ccgaaatcag taacttgtcg 3480
gtttctgatt tacagattca tgtagcaact ccagagattg aagaagacac atacggccat 3540
atgggagatt ggtctgaggc taaaattcaa gatggaactc ttgtcattaa ttggaatcct 3600
actggatatc gattagatcc tcaaaaagca ggggctttag tatttaatgc attatgggaa 3660
gaaggggctg tcttgtctgc tctgaaaaat gcacgctttg ctcataatct cactgctcag 3720
cgtatggaat tcgattattc tacaaatgtg tggggattcg cctttggtgg tttccgaact 3780
ctatctgcag agaatctggt tgctattgat ggatacaaag gagcttatgg tggtgcttct 3840
gctggagtcg atattcaatt gatggaagat tttgttctag gagttagtgg agctgctttc 3900
ctaggtaaaa tggatagtca gaagtttgat gcggaggttt ctcggaaggg agttgttggt 3960
tctgtatata caggattttt agctggatcc tggttcttca aaggacaata tagccttgga 4020
gaaacacaga acgatatgaa aacgcgttat ggagtactag gagagtcgag tgcttcttgg 4080
acatctcgag gagtactggc agatgcttta gttgaatacc gaagtttagt tggtcctgtg 4140
agacctactt tttatgcttt gcatttcaat ccttatgtcg aagtatctta tgcttctatg 4200
aaattccctg gctttacaga acaaggaaga gaagcgcgtt cttttgaaga cgcttccctt 4260
accaatatca ccattccttt agggatgaag tttgaattgg cgttcataaa aggacagttt 4320
tcagaggtga actctttggg aataagttat gcatgggaag cttatcgaaa agtagaagga 4380
ggcgcggtgc agcttttaga agctgggttt gattgggagg gagctccaat ggatcttcct 4440
agacaggagc tgcgtgtcgc tctggaaaat aatacggaat ggagttctta cttcagcaca 4500
gtcttaggat taacagcttt ttgtggagga tttacttcta cagatagtaa actaggatat 4560
gaggcgaatg ctggattgcg attgatcttt taa 4593

<210> SEQ ID NO 4
<211> LENGTH: 1531
<212> TYPE: PRT
<213> ORGANISM: Chlamydia trachomatis

<400> SEQUENCE: 4

Met Ser Ser Glu Lys Asp Ile Lys Ser Thr Cys Ser Lys Phe Ser Leu
1 5 10 15

Ser Val Val Ala Ala Ile Leu Ala Ser Val Ser Gly Leu Ala Ser Cys
20 25 30

Val Asp Leu His Ala Gly Gly Gln Ser Val Asn Glu Leu Val Tyr Val
35 40 45

Gly Pro Gln Ala Val Leu Leu Leu Asp Gln Ile Arg Asp Leu Phe Val
50 55 60

Gly Ser Lys Asp Ser Gln Ala Glu Gly Gln Tyr Arg Leu Ile Val Gly
65 70 75 80

Asp Pro Ser Ser Phe Gln Glu Lys Asp Ala Asp Thr Leu Pro Gly Lys
85 90 95

-continued

```
Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Gly Ala Leu Phe
465                 470                 475                 480

Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510
```

-continued

```
Gly Ala Ile Leu Ala Thr Gly Lys Val Glu Ile Thr Asn Asn Ser Glu
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Glu Gly Arg Pro Leu Ser
545                 550                 555                 560

Ser Gly Tyr Ser Gly Gly Gly Ala Ile Leu Gly Arg Glu Val Ala Ile
                565                 570                 575

Leu His Asn Ala Ala Val Val Phe Glu Gln Asn Arg Leu Gln Cys Ser
            580                 585                 590

Glu Glu Glu Ala Thr Leu Leu Gly Cys Cys Gly Gly Gly Ala Val His
        595                 600                 605

Gly Met Asp Ser Thr Ser Ile Val Gly Asn Ser Ser Val Arg Phe Gly
    610                 615                 620

Asn Asn Tyr Ala Met Gly Gln Gly Val Ser Gly Gly Ala Leu Leu Ser
625                 630                 635                 640

Lys Thr Val Gln Leu Ala Gly Asn Gly Ser Val Asp Phe Ser Arg Asn
                645                 650                 655

Ile Ala Ser Leu Gly Gly Gly Ala Leu Gln Ala Ser Glu Gly Asn Cys
            660                 665                 670

Glu Leu Val Asp Asn Gly Tyr Val Leu Phe Arg Asp Asn Arg Gly Arg
        675                 680                 685

Val Tyr Gly Gly Ala Ile Ser Cys Leu Arg Gly Asp Val Val Ile Ser
    690                 695                 700

Gly Asn Lys Gly Arg Val Glu Phe Lys Asp Asn Ile Ala Thr Arg Leu
705                 710                 715                 720

Tyr Val Glu Glu Thr Val Glu Lys Val Glu Glu Val Glu Pro Ala Pro
                725                 730                 735

Glu Gln Lys Asp Asn Asn Glu Leu Ser Phe Leu Gly Ser Ala Glu Gln
            740                 745                 750

Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Val Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
            820                 825                 830

Gly Gln Ile Pro Glu Val Leu Ile Ser Gly Asn Ala Gly Asp Val Val
        835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
            900                 905                 910

Val Phe Lys Gly Asn Ser Ser Phe Arg Ala Gln Gly Ser Asp Ala Ile
        915                 920                 925

Tyr Phe Ala Gly Lys Glu Ser His Ile Thr Ala Leu Asn Ala Thr Glu
```

-continued

```
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly  Ser Leu Glu Leu Leu  Asn Gly Ala
        995                 1000                1005

Thr Leu  Cys Ser Tyr Gly Phe  Lys Gln Asp Ala Gly  Ala Lys Leu
    1010                1015                1020

Val Leu  Ala Ala Gly Ala Lys  Leu Lys Ile Leu Asp  Ser Gly Thr
    1025                1030                1035

Pro Val  Gln Gln Gly His Ala  Ile Ser Lys Pro Glu  Ala Glu Ile
    1040                1045                1050

Glu Ser  Ser Ser Glu Pro Glu  Gly Ala His Ser Leu  Trp Ile Ala
    1055                1060                1065

Lys Asn  Ala Gln Thr Thr Val  Pro Met Val Asp Ile  His Thr Ile
    1070                1075                1080

Ser Val  Asp Leu Ala Ser Phe  Ser Ser Ser Gln Gln  Glu Gly Thr
    1085                1090                1095

Val Glu  Ala Pro Gln Val Ile  Val Pro Gly Gly Ser  Tyr Val Arg
    1100                1105                1110

Ser Gly  Glu Leu Asn Leu Glu  Leu Val Asn Thr Thr  Gly Thr Gly
    1115                1120                1125

Tyr Glu  Asn His Ala Leu Leu  Lys Asn Glu Ala Lys  Val Pro Leu
    1130                1135                1140

Met Ser  Phe Val Ala Ser Gly  Asp Glu Ala Ser Ala  Glu Ile Ser
    1145                1150                1155

Asn Leu  Ser Val Ser Asp Leu  Gln Ile His Val Val  Thr Pro Glu
    1160                1165                1170

Ile Glu  Glu Asp Thr Tyr Gly  His Met Gly Asp Trp  Ser Glu Ala
    1175                1180                1185

Lys Ile  Gln Asp Gly Thr Leu  Val Ile Ser Trp Asn  Pro Thr Gly
    1190                1195                1200

Tyr Arg  Leu Asp Pro Gln Lys  Ala Gly Ala Leu Val  Phe Asn Ala
    1205                1210                1215

Leu Trp  Glu Glu Gly Ala Val  Leu Ser Ala Leu Lys  Asn Ala Arg
    1220                1225                1230

Phe Ala  His Asn Leu Thr Ala  Gln Arg Met Glu Phe  Asp Tyr Ser
    1235                1240                1245

Thr Asn  Val Trp Gly Phe Ala  Phe Gly Gly Phe Arg  Thr Leu Ser
    1250                1255                1260

Ala Glu  Asn Leu Val Ala Ile  Asp Gly Tyr Lys Gly  Ala Tyr Gly
    1265                1270                1275

Gly Ala  Ser Ala Gly Val Asp  Ile Gln Leu Met Glu  Asp Phe Val
    1280                1285                1290

Leu Gly  Val Ser Gly Ala Ala  Phe Leu Gly Lys Met  Asp Ser Gln
    1295                1300                1305

Lys Phe  Asp Ala Glu Val Ser  Arg Lys Gly Val Val  Gly Ser Val
    1310                1315                1320

Tyr Thr  Gly Phe Leu Ala Gly  Ser Trp Phe Phe Lys  Gly Gln Tyr
    1325                1330                1335
```

```
Ser Leu  Gly Glu Thr Gln Asn  Asp Met Lys Thr Arg  Tyr Gly Val
    1340                 1345                 1350

Leu Gly  Glu Ser Ser Ala Ser  Trp Thr Ser Arg Gly  Val Leu Ala
    1355                 1360                 1365

Asp Ala  Leu Val Glu Tyr Arg  Ser Leu Val Gly Pro  Val Arg Pro
    1370                 1375                 1380

Thr Phe  Tyr Ala Leu His Phe  Asn Pro Tyr Val Glu  Val Ser Tyr
    1385                 1390                 1395

Ala Ser  Met Lys Phe Pro Gly  Phe Thr Glu Gln Gly  Arg Glu Ala
    1400                 1405                 1410

Arg Ser  Phe Glu Asp Ala Ser  Leu Thr Asn Ile Thr  Ile Pro Leu
    1415                 1420                 1425

Gly Met  Lys Phe Glu Leu Ala  Phe Ile Lys Gly Gln  Phe Ser Glu
    1430                 1435                 1440

Val Asn  Ser Leu Gly Ile Ser  Tyr Ala Trp Glu Ala  Tyr Arg Lys
    1445                 1450                 1455

Val Glu  Gly Gly Ala Val Gln  Leu Leu Glu Ala Gly  Phe Asp Trp
    1460                 1465                 1470

Glu Gly  Ala Pro Met Asp Leu  Pro Arg Gln Glu Leu  Arg Val Ala
    1475                 1480                 1485

Leu Glu  Asn Asn Thr Glu Trp  Ser Ser Tyr Phe Ser  Thr Val Leu
    1490                 1495                 1500

Gly Leu  Thr Ala Phe Cys Gly  Gly Phe Thr Ser Thr  Asp Ser Lys
    1505                 1510                 1515

Leu Gly  Tyr Lys Ala Asn Thr  Gly Leu Arg Leu Ile  Phe
    1520                 1525                 1530
```

<210> SEQ ID NO 5
<211> LENGTH: 1531
<212> TYPE: PRT
<213> ORGANISM: Chlamydia trachomatis

<400> SEQUENCE: 5

```
Met Ser Ser Glu Lys Asp Ile Lys Ser Thr Cys Ser Lys Phe Ser Leu
1               5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
```

-continued

```
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Gly Ala Leu Phe
465                 470                 475                 480

Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510

Gly Ala Ile Leu Ala Thr Gly Lys Val Glu Ile Thr Asn Asn Ser Glu
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Glu Gly Arg Pro Leu Ser
545                 550                 555                 560

Ser Gly Tyr Ser Gly Gly Gly Ala Ile Leu Gly Arg Glu Val Ala Ile
                565                 570                 575

Leu His Asn Ala Ala Val Val Phe Glu Gln Asn Arg Leu Gln Cys Ser
            580                 585                 590
```

-continued

```
Glu Glu Glu Ala Thr Leu Leu Gly Cys Cys Gly Gly Gly Ala Val His
        595                 600                 605

Gly Met Asp Ser Thr Ser Ile Val Gly Asn Ser Ser Val Arg Phe Gly
    610                 615                 620

Asn Asn Tyr Ala Met Gly Gln Gly Val Ser Gly Gly Ala Leu Leu Ser
625                 630                 635                 640

Lys Thr Val Gln Leu Ala Gly Asn Gly Ser Val Asp Phe Ser Arg Asn
                645                 650                 655

Ile Ala Ser Leu Gly Gly Gly Ala Leu Gln Ala Ser Glu Gly Asn Cys
            660                 665                 670

Glu Leu Val Asp Asn Gly Tyr Val Leu Phe Arg Asp Asn Arg Gly Arg
        675                 680                 685

Val Tyr Gly Gly Ala Ile Ser Cys Leu Arg Gly Asp Val Val Ile Ser
    690                 695                 700

Gly Asn Lys Gly Arg Val Glu Phe Lys Asp Asn Ile Ala Thr Arg Leu
705                 710                 715                 720

Tyr Val Glu Glu Thr Val Glu Lys Val Glu Glu Val Glu Pro Ala Pro
                725                 730                 735

Glu Gln Lys Asp Asn Asn Glu Leu Ser Phe Leu Gly Arg Ala Glu Gln
            740                 745                 750

Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
            820                 825                 830

Gly Gln Ile Pro Glu Val Leu Ile Ser Gly Asn Ala Gly Asp Val Val
        835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
            900                 905                 910

Val Phe Lys Gly Asn Ser Ser Phe Arg Ala Gln Gly Ser Asp Ala Ile
        915                 920                 925

Tyr Phe Ala Gly Lys Glu Ser His Ile Thr Ala Leu Asn Ala Thr Glu
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly  Ser Leu Glu Leu Leu  Asn Gly Ala
        995                 1000                1005
```

```
Thr Leu  Cys Ser Tyr Gly Phe  Lys Gln Asp Ala Gly  Ala Lys Leu
    1010                 1015                 1020

Val Leu  Ala Ala Gly Ala Lys  Leu Lys Ile Leu Asp  Ser Gly Thr
    1025                 1030                 1035

Pro Val  Gln Gln Gly His Ala  Ile Ser Lys Pro Glu  Ala Glu Ile
    1040                 1045                 1050

Glu Ser  Ser Ser Glu Pro Glu  Gly Ala His Ser Leu  Trp Ile Ala
    1055                 1060                 1065

Lys Asn  Ala Gln Thr Thr Val  Pro Met Val Asp Ile  His Thr Ile
    1070                 1075                 1080

Ser Val  Asp Leu Ala Ser Phe  Ser Ser Ser Gln Gln  Glu Gly Thr
    1085                 1090                 1095

Val Glu  Ala Pro Gln Val Ile  Val Pro Gly Gly Ser  Tyr Val Arg
    1100                 1105                 1110

Ser Gly  Glu Leu Asn Leu Glu  Leu Val Asn Thr Thr  Gly Thr Gly
    1115                 1120                 1125

Tyr Glu  Asn His Ala Leu Leu  Lys Asn Glu Ala Lys  Val Pro Leu
    1130                 1135                 1140

Met Ser  Phe Val Ala Ser Gly  Asp Glu Ala Ser Ala  Glu Ile Ser
    1145                 1150                 1155

Asn Leu  Ser Val Ser Asp Leu  Gln Ile His Val Val  Thr Pro Glu
    1160                 1165                 1170

Ile Glu  Glu Asp Thr Tyr Gly  His Met Gly Asp Trp  Ser Glu Ala
    1175                 1180                 1185

Lys Ile  Gln Asp Gly Thr Leu  Val Ile Ser Trp Asn  Pro Thr Gly
    1190                 1195                 1200

Tyr Arg  Leu Asp Pro Gln Lys  Ala Gly Ala Leu Val  Phe Asn Ala
    1205                 1210                 1215

Leu Trp  Glu Glu Gly Ala Val  Leu Ser Ala Leu Lys  Asn Ala Arg
    1220                 1225                 1230

Phe Ala  His Asn Leu Thr Ala  Gln Arg Met Glu Phe  Asp Tyr Ser
    1235                 1240                 1245

Thr Asn  Val Trp Gly Phe Ala  Phe Gly Gly Phe Arg  Thr Leu Ser
    1250                 1255                 1260

Ala Glu  Asn Leu Val Ala Ile  Asp Gly Tyr Lys Gly  Ala Tyr Gly
    1265                 1270                 1275

Gly Ala  Ser Ala Gly Val Asp  Ile Gln Leu Met Glu  Asp Phe Val
    1280                 1285                 1290

Leu Gly  Val Ser Gly Ala Ala  Phe Leu Gly Lys Met  Asp Ser Gln
    1295                 1300                 1305

Lys Phe  Asp Ala Glu Val Ser  Arg Lys Gly Val Val  Gly Ser Val
    1310                 1315                 1320

Tyr Thr  Gly Phe Leu Ala Gly  Ser Trp Phe Phe Lys  Gly Gln Tyr
    1325                 1330                 1335

Ser Leu  Gly Glu Thr Gln Asn  Asp Met Lys Thr Arg  Tyr Gly Val
    1340                 1345                 1350

Leu Gly  Glu Ser Ser Ala Ser  Trp Thr Ser Arg Gly  Val Leu Ala
    1355                 1360                 1365

Asp Ala  Leu Val Glu Tyr Arg  Ser Leu Val Gly Pro  Val Arg Pro
    1370                 1375                 1380

Thr Phe  Tyr Ala Leu His Phe  Asn Pro Tyr Val Glu  Val Ser Tyr
    1385                 1390                 1395

Ala Ser  Met Lys Phe Pro Gly  Phe Thr Glu Gln Gly  Arg Glu Ala
```

```
    1400                1405                1410

Arg Ser  Phe Glu Asp Ala Ser  Leu Thr Asn Ile Thr  Ile Pro Leu
    1415                1420                1425

Gly Met  Lys Phe Glu Leu Ala  Phe Ile Lys Gly Gln  Phe Ser Glu
    1430                1435                1440

Val Asn  Ser Leu Gly Ile Ser  Tyr Ala Trp Glu Ala  Tyr Arg Lys
    1445                1450                1455

Val Glu  Gly Gly Ala Val Gln  Leu Leu Glu Ala Gly  Phe Asp Trp
    1460                1465                1470

Glu Gly  Ala Pro Met Asp Leu  Pro Arg Gln Glu Leu  Arg Val Ala
    1475                1480                1485

Leu Glu  Asn Asn Thr Glu Trp  Ser Ser Tyr Phe Ser  Thr Val Leu
    1490                1495                1500

Gly Leu  Thr Ala Phe Cys Gly  Gly Phe Thr Ser Thr  Asp Ser Lys
    1505                1510                1515

Leu Gly  Tyr Glu Ala Asn Thr  Gly Leu Arg Leu Ile  Phe
    1520                1525                1530


<210> SEQ ID NO 6
<211> LENGTH: 1530
<212> TYPE: PRT
<213> ORGANISM: Chlamydia trachomatis

<400> SEQUENCE: 6

Met Ser Ser Glu Lys Asp Ile Lys Ser Thr Cys Ser Lys Phe Ser Leu
1               5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240
```

-continued

```
Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Gly Ala Leu Phe
465                 470                 475                 480

Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510

Gly Ala Ile Leu Ala Thr Gly Lys Val Glu Ile Thr Asn Asn Ser Gly
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Glu Gly Arg Pro Leu Ser
545                 550                 555                 560

Ser Gly Tyr Ser Gly Gly Gly Ala Ile Leu Gly Arg Glu Val Ala Ile
                565                 570                 575

Leu His Asn Ala Ala Val Val Phe Glu Gln Asn Arg Leu Gln Cys Ser
            580                 585                 590

Glu Glu Glu Ala Thr Leu Leu Gly Cys Cys Gly Gly Gly Ala Val His
        595                 600                 605

Gly Met Asp Ser Thr Ser Ile Val Gly Asn Ser Ser Val Arg Phe Gly
    610                 615                 620

Asn Asn Tyr Ala Met Gly Gln Gly Val Ser Gly Gly Ala Leu Leu Ser
625                 630                 635                 640

Lys Thr Val Gln Leu Ala Gly Asn Gly Ser Val Asp Phe Ser Arg Asn
                645                 650                 655

Ile Ala Ser Leu Gly Gly Gly Ala Leu Gln Ala Ser Glu Gly Asn Cys
```

-continued

```
            660                 665                 670

Glu Leu Val Asp Asn Gly Tyr Val Leu Phe Arg Asp Asn Arg Gly Arg
        675                 680                 685

Val Tyr Gly Gly Ala Ile Ser Cys Leu Arg Gly Asp Val Val Ile Ser
    690                 695                 700

Gly Asn Lys Gly Arg Val Glu Phe Lys Asp Asn Ile Ala Thr Arg Leu
705                 710                 715                 720

Tyr Val Glu Glu Thr Val Glu Lys Val Glu Glu Val Glu Pro Ala Pro
                725                 730                 735

Glu Gln Lys Asp Asn Asn Glu Leu Ser Phe Leu Gly Ser Val Glu Gln
            740                 745                 750

Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
            820                 825                 830

Gly Gln Ile Pro Glu Val Leu Ile Ser Gly Asn Ala Gly Asp Val Val
        835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
            900                 905                 910

Val Phe Lys Gly Asn Ser Ser Phe Arg Ala Gln Gly Ser Asp Ala Ile
        915                 920                 925

Tyr Phe Ala Gly Lys Glu Ser His Ile Thr Ala Leu Asn Ala Thr Glu
    930                 935                 940

Gly His Ala Ile Val Phe His Asp Ala Leu Val Phe Glu Asn Leu Lys
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly  Ser Leu Glu Leu Leu  Asn Gly Ala
        995                 1000                1005

Thr Leu  Cys Ser Tyr Gly Phe  Lys Gln Asp Ala Gly  Ala Lys Leu
    1010                1015                1020

Val Leu  Ala Ala Gly Ser Lys  Leu Lys Ile Leu Asp  Ser Gly Thr
    1025                1030                1035

Pro Val  Gln Gly His Ala Ile  Ser Lys Pro Glu Ala  Glu Ile Glu
    1040                1045                1050

Ser Ser  Ser Glu Pro Glu Gly  Ala His Ser Leu Trp  Ile Ala Lys
    1055                1060                1065

Asn Ala  Gln Thr Thr Val Pro  Met Val Asp Ile His  Thr Ile Ser
    1070                1075                1080
```

```
Val Asp  Leu Ala Ser Phe Ser  Ser Ser Gln Gln Glu  Gly Thr Val
    1085                 1090                 1095

Glu Ala  Pro Gln Val Ile Val  Pro Gly Gly Ser Tyr  Val Arg Ser
    1100                 1105                 1110

Gly Glu  Leu Asn Leu Glu Leu  Val Asn Thr Thr Gly  Thr Gly Tyr
    1115                 1120                 1125

Glu Asn  His Ala Leu Leu Lys  Asn Glu Ala Lys Val  Pro Leu Met
    1130                 1135                 1140

Ser Phe  Val Ala Ser Ser Asp  Glu Ala Ser Ala Glu  Ile Ser Asn
    1145                 1150                 1155

Leu Ser  Val Ser Asp Leu Gln  Ile His Val Ala Thr  Pro Glu Ile
    1160                 1165                 1170

Glu Glu  Asp Thr Tyr Gly His  Met Gly Asp Trp Ser  Glu Ala Lys
    1175                 1180                 1185

Ile Gln  Asp Gly Thr Leu Val  Ile Asn Trp Asn Pro  Thr Gly Tyr
    1190                 1195                 1200

Arg Leu  Asp Pro Gln Lys Ala  Gly Ala Leu Val Phe  Asn Ala Leu
    1205                 1210                 1215

Trp Glu  Glu Gly Ala Val Leu  Ser Ala Leu Lys Asn  Ala Arg Phe
    1220                 1225                 1230

Ala His  Asn Leu Thr Ala Gln  Arg Met Glu Phe Asp  Tyr Ser Thr
    1235                 1240                 1245

Asn Val  Trp Gly Phe Ala Phe  Gly Gly Phe Arg Thr  Leu Ser Ala
    1250                 1255                 1260

Glu Asn  Leu Val Ala Ile Asp  Gly Tyr Lys Gly Ala  Tyr Gly Gly
    1265                 1270                 1275

Ala Ser  Ala Gly Val Asp Ile  Gln Leu Met Glu Asp  Phe Val Leu
    1280                 1285                 1290

Gly Val  Ser Gly Ala Ala Phe  Leu Gly Lys Met Asp  Ser Gln Lys
    1295                 1300                 1305

Phe Asp  Ala Glu Val Ser Arg  Lys Gly Val Val Gly  Ser Val Tyr
    1310                 1315                 1320

Thr Gly  Phe Leu Ala Gly Ser  Trp Phe Phe Lys Gly  Gln Tyr Ser
    1325                 1330                 1335

Leu Gly  Glu Thr Gln Asn Asp  Met Lys Thr Arg Tyr  Gly Val Leu
    1340                 1345                 1350

Gly Glu  Ser Ser Ala Ser Trp  Thr Ser Arg Gly Val  Leu Ala Asp
    1355                 1360                 1365

Ala Leu  Val Glu Tyr Arg Ser  Leu Val Gly Pro Val  Arg Pro Thr
    1370                 1375                 1380

Phe Tyr  Ala Leu His Phe Asn  Pro Tyr Val Glu Val  Ser Tyr Ala
    1385                 1390                 1395

Ser Met  Lys Phe Pro Gly Phe  Thr Glu Gln Gly Arg  Glu Ala Arg
    1400                 1405                 1410

Ser Phe  Glu Asp Ala Ser Leu  Thr Asn Ile Thr Ile  Pro Leu Gly
    1415                 1420                 1425

Met Lys  Phe Glu Leu Ala Phe  Ile Lys Gly Gln Phe  Ser Glu Val
    1430                 1435                 1440

Asn Ser  Leu Gly Ile Ser Tyr  Ala Trp Glu Ala Tyr  Arg Lys Val
    1445                 1450                 1455

Glu Gly  Gly Ala Val Gln Leu  Leu Glu Ala Gly Phe  Asp Trp Glu
    1460                 1465                 1470
```

Gly Ala Pro Met Asp Leu Pro Arg Gln Glu Leu Arg Val Ala Leu
1475 1480 1485

Glu Asn Asn Thr Glu Trp Ser Ser Tyr Phe Ser Thr Val Leu Gly
1490 1495 1500

Leu Thr Ala Phe Cys Gly Gly Phe Thr Ser Thr Asp Ser Lys Leu
1505 1510 1515

Gly Tyr Glu Ala Asn Ala Gly Leu Arg Leu Ile Phe
1520 1525 1530

<210> SEQ ID NO 7
<211> LENGTH: 1036
<212> TYPE: PRT
<213> ORGANISM: Chlamydia trachomatis

<400> SEQUENCE: 7

Ser Gly Leu Ala Ser Cys Val Asp Leu His Ala Gly Gly Gln Ser Val
1 5 10 15

Asn Glu Leu Val Tyr Val Gly Pro Gln Ala Val Leu Leu Leu Asp Gln
20 25 30

Ile Arg Asp Leu Phe Val Gly Ser Lys Asp Ser Gln Ala Glu Gly Gln
35 40 45

Tyr Arg Leu Ile Val Gly Asp Pro Ser Ser Phe Gln Glu Lys Asp Ala
50 55 60

Asp Thr Leu Pro Gly Lys Val Glu Gln Ser Thr Leu Phe Ser Val Thr
65 70 75 80

Asn Pro Val Val Phe Gln Gly Val Asp Gln Gln Asp Gln Val Ser Ser
85 90 95

Gln Gly Leu Ile Cys Ser Phe Thr Ser Ser Asn Leu Asp Ser Pro Arg
100 105 110

Asp Gly Glu Ser Phe Leu Gly Ile Ala Phe Val Gly Asp Ser Ser Lys
115 120 125

Ala Gly Ile Thr Leu Thr Asp Val Lys Ala Ser Leu Ser Gly Ala Ala
130 135 140

Leu Tyr Ser Thr Glu Asp Leu Ile Phe Glu Lys Ile Lys Gly Gly Leu
145 150 155 160

Glu Phe Ala Ser Cys Ser Ser Leu Glu Gln Gly Gly Ala Cys Ala Ala
165 170 175

Gln Ser Ile Leu Ile His Asp Cys Gln Gly Leu Gln Val Lys His Cys
180 185 190

Thr Thr Ala Val Asn Ala Glu Gly Ser Ser Ala Asn Asp His Leu Gly
195 200 205

Phe Gly Gly Gly Ala Phe Phe Val Thr Gly Ser Leu Ser Gly Glu Lys
210 215 220

Ser Leu Tyr Met Pro Ala Gly Asp Met Val Val Ala Asn Cys Asp Gly
225 230 235 240

Ala Ile Ser Phe Glu Gly Asn Ser Ala Asn Phe Ala Asn Gly Gly Ala
245 250 255

Ile Ala Ala Ser Gly Lys Val Leu Phe Val Ala Asn Asp Lys Lys Thr
260 265 270

Ser Phe Ile Glu Asn Arg Ala Leu Ser Gly Gly Ala Ile Ala Ala Ser
275 280 285

Ser Asp Ile Ala Phe Gln Asn Cys Ala Glu Leu Val Phe Lys Gly Asn
290 295 300

Cys Ala Ile Gly Thr Glu Asp Lys Gly Ser Leu Gly Gly Gly Ala Ile
305 310 315 320

-continued

```
Ser Ser Leu Gly Thr Val Leu Leu Gln Gly Asn His Gly Ile Thr Cys
                325                 330                 335

Asp Lys Asn Glu Ser Ala Ser Gln Gly Gly Ala Ile Phe Gly Lys Asn
            340                 345                 350

Cys Gln Ile Ser Asp Asn Glu Gly Pro Val Val Phe Arg Asp Ser Thr
        355                 360                 365

Ala Cys Leu Gly Gly Gly Ala Ile Ala Ala Gln Glu Ile Val Ser Ile
    370                 375                 380

Gln Asn Asn Gln Ala Gly Ile Ser Phe Glu Gly Gly Lys Ala Ser Phe
385                 390                 395                 400

Gly Gly Gly Ile Ala Cys Gly Ser Phe Ser Ser Ala Gly Gly Ala Ser
                405                 410                 415

Val Leu Gly Thr Ile Asp Ile Ser Lys Asn Leu Gly Ala Ile Ser Phe
            420                 425                 430

Ser Arg Thr Leu Cys Thr Thr Ser Asp Leu Gly Gln Met Glu Tyr Gln
        435                 440                 445

Gly Gly Gly Ala Leu Phe Gly Glu Asn Ile Ser Leu Ser Glu Asn Ala
    450                 455                 460

Gly Val Leu Thr Phe Lys Asp Asn Ile Val Lys Thr Phe Ala Ser Asn
465                 470                 475                 480

Gly Lys Ile Leu Gly Gly Gly Ala Ile Leu Ala Thr Gly Lys Val Glu
                485                 490                 495

Ile Thr Asn Asn Ser Glu Gly Ile Ser Phe Thr Gly Asn Ala Arg Ala
            500                 505                 510

Pro Gln Ala Leu Pro Thr Gln Glu Glu Phe Pro Leu Phe Ser Lys Lys
        515                 520                 525

Glu Gly Arg Pro Leu Ser Ser Gly Tyr Ser Gly Gly Gly Ala Ile Leu
    530                 535                 540

Gly Arg Glu Val Ala Ile Leu His Asn Ala Ala Val Val Phe Glu Gln
545                 550                 555                 560

Asn Arg Leu Gln Cys Ser Glu Glu Glu Ala Thr Leu Leu Gly Cys Cys
                565                 570                 575

Gly Gly Gly Ala Val His Gly Met Asp Ser Thr Ser Ile Val Gly Asn
            580                 585                 590

Ser Ser Val Arg Phe Gly Asn Asn Tyr Ala Met Gly Gln Gly Val Ser
        595                 600                 605

Gly Gly Ala Leu Leu Ser Lys Thr Val Gln Leu Ala Gly Asn Gly Ser
    610                 615                 620

Val Asp Phe Ser Arg Asn Ile Ala Ser Leu Gly Gly Gly Ala Leu Gln
625                 630                 635                 640

Ala Ser Glu Gly Asn Cys Glu Leu Val Asp Asn Gly Tyr Val Leu Phe
                645                 650                 655

Arg Asp Asn Arg Gly Arg Val Tyr Gly Gly Ala Ile Ser Cys Leu Arg
            660                 665                 670

Gly Asp Val Val Ile Ser Gly Asn Lys Gly Arg Val Glu Phe Lys Asp
        675                 680                 685

Asn Ile Ala Thr Arg Leu Tyr Val Glu Glu Thr Val Glu Lys Val Glu
    690                 695                 700

Glu Val Glu Pro Ala Pro Glu Gln Lys Asp Asn Asn Glu Leu Ser Phe
705                 710                 715                 720

Leu Gly Ser Ala Glu Gln Ser Phe Ile Thr Ala Ala Asn Gln Ala Leu
                725                 730                 735
```

```
Phe Ala Ser Glu Asp Gly Asp Leu Ser Pro Glu Ser Ser Ile Ser Ser
            740                 745                 750

Glu Glu Leu Val Lys Arg Arg Glu Cys Ala Gly Gly Ala Ile Phe Ala
        755                 760                 765

Lys Arg Val Arg Ile Val Asp Asn Gln Glu Ala Val Val Phe Ser Asn
    770                 775                 780

Asn Phe Ser Asp Ile Tyr Gly Gly Ala Ile Phe Thr Gly Ser Leu Arg
785                 790                 795                 800

Glu Glu Asp Lys Leu Asp Gly Gln Ile Pro Glu Val Leu Ile Ser Gly
                805                 810                 815

Asn Ala Gly Asp Val Val Phe Ser Gly Asn Ser Ser Lys Arg Asp Glu
            820                 825                 830

His Leu Pro His Thr Gly Gly Gly Ala Ile Cys Thr Gln Asn Leu Thr
        835                 840                 845

Ile Ser Gln Asn Thr Gly Asn Val Leu Phe Tyr Asn Asn Val Ala Cys
    850                 855                 860

Ser Gly Gly Ala Val Arg Ile Glu Asp His Gly Asn Val Leu Leu Glu
865                 870                 875                 880

Ala Phe Gly Gly Asp Ile Val Phe Lys Gly Asn Ser Ser Phe Arg Ala
                885                 890                 895

Gln Gly Ser Asp Ala Ile Tyr Phe Ala Gly Lys Glu Ser His Ile Thr
            900                 905                 910

Ala Leu Asn Ala Thr Glu Gly His Ala Ile Val Phe His Asp Ala Leu
        915                 920                 925

Val Phe Glu Asn Leu Glu Glu Arg Lys Ser Ala Glu Val Leu Leu Ile
    930                 935                 940

Asn Ser Arg Glu Asn Pro Gly Tyr Thr Gly Ser Ile Arg Phe Leu Glu
945                 950                 955                 960

Ala Glu Ser Lys Val Pro Gln Cys Ile His Val Gln Gln Gly Ser Leu
                965                 970                 975

Glu Leu Leu Asn Gly Ala Thr Leu Cys Ser Tyr Gly Phe Lys Gln Asp
            980                 985                 990

Ala Gly Ala Lys Leu Val Leu Ala  Ala Gly Ala Lys Leu  Lys Ile Leu
        995                 1000                1005

Asp Ser  Gly Thr Pro Val Gln  Gln Gly His Ala Ile  Ser Lys Pro
    1010                1015                1020

Glu Ala  Glu Ile Glu Ser Ser  Ser Glu Pro Glu Gly  Ala
    1025                1030                1035


<210> SEQ ID NO 8
<211> LENGTH: 1032
<212> TYPE: PRT
<213> ORGANISM: Chlamydia trachomatis

<400> SEQUENCE: 8

Ser Cys Val Asp Leu His Ala Gly Gly Gln Ser Val Asn Glu Leu Val
1               5                   10                  15

Tyr Val Gly Pro Gln Ala Val Leu Leu Leu Asp Gln Ile Arg Asp Leu
            20                  25                  30

Phe Val Gly Ser Lys Asp Ser Gln Ala Glu Gly Gln Tyr Arg Leu Ile
        35                  40                  45

Val Gly Asp Pro Ser Ser Phe Gln Glu Lys Asp Ala Asp Thr Leu Pro
    50                  55                  60

Gly Lys Val Glu Gln Ser Thr Leu Phe Ser Val Thr Asn Pro Val Val
65                  70                  75                  80
```

```
Phe Gln Gly Val Asp Gln Gln Asp Gln Val Ser Ser Gln Gly Leu Ile
                85                  90                  95

Cys Ser Phe Thr Ser Ser Asn Leu Asp Ser Pro Arg Asp Gly Glu Ser
            100                 105                 110

Phe Leu Gly Ile Ala Phe Val Gly Asp Ser Ser Lys Ala Gly Ile Thr
        115                 120                 125

Leu Thr Asp Val Lys Ala Ser Leu Ser Gly Ala Ala Leu Tyr Ser Thr
    130                 135                 140

Glu Asp Leu Ile Phe Glu Lys Ile Lys Gly Gly Leu Glu Phe Ala Ser
145                 150                 155                 160

Cys Ser Ser Leu Glu Gln Gly Gly Ala Cys Ala Ala Gln Ser Ile Leu
                165                 170                 175

Ile His Asp Cys Gln Gly Leu Gln Val Lys His Cys Thr Thr Ala Val
            180                 185                 190

Asn Ala Glu Gly Ser Ser Ala Asn Asp His Leu Gly Phe Gly Gly Gly
        195                 200                 205

Ala Phe Phe Val Thr Gly Ser Leu Ser Gly Glu Lys Ser Leu Tyr Met
    210                 215                 220

Pro Ala Gly Asp Met Val Val Ala Asn Cys Asp Gly Ala Ile Ser Phe
225                 230                 235                 240

Glu Gly Asn Ser Ala Asn Phe Ala Asn Gly Gly Ala Ile Ala Ala Ser
                245                 250                 255

Gly Lys Val Leu Phe Val Ala Asn Asp Lys Lys Thr Ser Phe Ile Glu
            260                 265                 270

Asn Arg Ala Leu Ser Gly Gly Ala Ile Ala Ala Ser Ser Asp Ile Ala
        275                 280                 285

Phe Gln Asn Cys Ala Glu Leu Val Phe Lys Gly Asn Cys Ala Ile Gly
    290                 295                 300

Thr Glu Asp Lys Gly Ser Leu Gly Gly Gly Ala Ile Ser Ser Leu Gly
305                 310                 315                 320

Thr Val Leu Leu Gln Gly Asn His Gly Ile Thr Cys Asp Lys Asn Glu
                325                 330                 335

Ser Ala Ser Gln Gly Gly Ala Ile Phe Gly Lys Asn Cys Gln Ile Ser
            340                 345                 350

Asp Asn Glu Gly Pro Val Val Phe Arg Asp Ser Thr Ala Cys Leu Gly
        355                 360                 365

Gly Gly Ala Ile Ala Ala Gln Glu Ile Val Ser Ile Gln Asn Asn Gln
    370                 375                 380

Ala Gly Ile Ser Phe Glu Gly Gly Lys Ala Ser Phe Gly Gly Gly Ile
385                 390                 395                 400

Ala Cys Gly Ser Phe Ser Ser Ala Gly Gly Ala Ser Val Leu Gly Thr
                405                 410                 415

Ile Asp Ile Ser Lys Asn Leu Gly Ala Ile Ser Phe Ser Arg Thr Leu
            420                 425                 430

Cys Thr Thr Ser Asp Leu Gly Gln Met Glu Tyr Gln Gly Gly Gly Ala
        435                 440                 445

Leu Phe Gly Glu Asn Ile Ser Leu Ser Glu Asn Ala Gly Val Leu Thr
    450                 455                 460

Phe Lys Asp Asn Ile Val Lys Thr Phe Ala Ser Asn Gly Lys Ile Leu
465                 470                 475                 480

Gly Gly Gly Ala Ile Leu Ala Thr Gly Lys Val Glu Ile Thr Asn Asn
                485                 490                 495
```

-continued

```
Ser Glu Gly Ile Ser Phe Thr Gly Asn Ala Arg Ala Pro Gln Ala Leu
            500                 505                 510

Pro Thr Gln Glu Glu Phe Pro Leu Phe Ser Lys Lys Glu Gly Arg Pro
        515                 520                 525

Leu Ser Ser Gly Tyr Ser Gly Gly Gly Ala Ile Leu Gly Arg Glu Val
    530                 535                 540

Ala Ile Leu His Asn Ala Ala Val Val Phe Glu Gln Asn Arg Leu Gln
545                 550                 555                 560

Cys Ser Glu Glu Glu Ala Thr Leu Leu Gly Cys Cys Gly Gly Gly Ala
                565                 570                 575

Val His Gly Met Asp Ser Thr Ser Ile Val Gly Asn Ser Ser Val Arg
            580                 585                 590

Phe Gly Asn Asn Tyr Ala Met Gly Gln Gly Val Ser Gly Gly Ala Leu
        595                 600                 605

Leu Ser Lys Thr Val Gln Leu Ala Gly Asn Gly Ser Val Asp Phe Ser
    610                 615                 620

Arg Asn Ile Ala Ser Leu Gly Gly Gly Ala Leu Gln Ala Ser Glu Gly
625                 630                 635                 640

Asn Cys Glu Leu Val Asp Asn Gly Tyr Val Leu Phe Arg Asp Asn Arg
                645                 650                 655

Gly Arg Val Tyr Gly Gly Ala Ile Ser Cys Leu Arg Gly Asp Val Val
            660                 665                 670

Ile Ser Gly Asn Lys Gly Arg Val Glu Phe Lys Asp Asn Ile Ala Thr
        675                 680                 685

Arg Leu Tyr Val Glu Glu Thr Val Glu Lys Val Glu Glu Val Glu Pro
    690                 695                 700

Ala Pro Glu Gln Lys Asp Asn Asn Glu Leu Ser Phe Leu Gly Arg Ala
705                 710                 715                 720

Glu Gln Ser Phe Ile Thr Ala Ala Asn Gln Ala Leu Phe Ala Ser Glu
                725                 730                 735

Asp Gly Asp Leu Ser Pro Glu Ser Ser Ile Ser Ser Glu Glu Leu Ala
            740                 745                 750

Lys Arg Arg Glu Cys Ala Gly Gly Ala Ile Phe Ala Lys Arg Val Arg
        755                 760                 765

Ile Val Asp Asn Gln Glu Ala Val Val Phe Ser Asn Asn Phe Ser Asp
    770                 775                 780

Ile Tyr Gly Gly Ala Ile Phe Thr Gly Ser Leu Arg Glu Glu Asp Lys
785                 790                 795                 800

Leu Asp Gly Gln Ile Pro Glu Val Leu Ile Ser Gly Asn Ala Gly Asp
                805                 810                 815

Val Val Phe Ser Gly Asn Ser Ser Lys Arg Asp Glu His Leu Pro His
            820                 825                 830

Thr Gly Gly Gly Ala Ile Cys Thr Gln Asn Leu Thr Ile Ser Gln Asn
        835                 840                 845

Thr Gly Asn Val Leu Phe Tyr Asn Asn Val Ala Cys Ser Gly Gly Ala
    850                 855                 860

Val Arg Ile Glu Asp His Gly Asn Val Leu Leu Glu Ala Phe Gly Gly
865                 870                 875                 880

Asp Ile Val Phe Lys Gly Asn Ser Ser Phe Arg Ala Gln Gly Ser Asp
                885                 890                 895

Ala Ile Tyr Phe Ala Gly Lys Glu Ser His Ile Thr Ala Leu Asn Ala
            900                 905                 910

Thr Glu Gly His Ala Ile Val Phe His Asp Ala Leu Val Phe Glu Asn
```

```
        915                 920                 925

Leu Glu Glu Arg Lys Ser Ala Glu Val Leu Leu Ile Asn Ser Arg Glu
    930                 935                 940

Asn Pro Gly Tyr Thr Gly Ser Ile Arg Phe Leu Glu Ala Glu Ser Lys
945                 950                 955                 960

Val Pro Gln Cys Ile His Val Gln Gln Gly Ser Leu Glu Leu Leu Asn
                965                 970                 975

Gly Ala Thr Leu Cys Ser Tyr Gly Phe Lys Gln Asp Ala Gly Ala Lys
            980                 985                 990

Leu Val Leu Ala Ala Gly Ala Lys  Leu Lys Ile Leu Asp  Ser Gly Thr
        995                 1000                1005

Pro Val  Gln Gln Gly His Ala  Ile Ser Lys Pro Glu  Ala Glu Ile
    1010                 1015                1020

Glu Ser  Ser Ser Glu Pro Glu  Gly Ala
    1025                 1030


<210> SEQ ID NO 9
<211> LENGTH: 1031
<212> TYPE: PRT
<213> ORGANISM: Chlamydia trachomatis

<400> SEQUENCE: 9

Ser Cys Val Asp Leu His Ala Gly Gly Gln Ser Val Asn Glu Leu Val
1               5                   10                  15

Tyr Val Gly Pro Gln Ala Val Leu Leu Leu Asp Gln Ile Arg Asp Leu
            20                  25                  30

Phe Val Gly Ser Lys Asp Ser Gln Ala Glu Gly Gln Tyr Arg Leu Ile
        35                  40                  45

Val Gly Asp Pro Ser Ser Phe Gln Glu Lys Asp Ala Asp Thr Leu Pro
    50                  55                  60

Gly Lys Val Glu Gln Ser Thr Leu Phe Ser Val Thr Asn Pro Val Val
65                  70                  75                  80

Phe Gln Gly Val Asp Gln Gln Asp Gln Val Ser Ser Gln Gly Leu Ile
                85                  90                  95

Cys Ser Phe Thr Ser Ser Asn Leu Asp Ser Pro Arg Asp Gly Glu Ser
            100                 105                 110

Phe Leu Gly Ile Ala Phe Val Gly Asp Ser Ser Lys Ala Gly Ile Thr
        115                 120                 125

Leu Thr Asp Val Lys Ala Ser Leu Ser Gly Ala Ala Leu Tyr Ser Thr
    130                 135                 140

Glu Asp Leu Ile Phe Glu Lys Ile Lys Gly Gly Leu Glu Phe Ala Ser
145                 150                 155                 160

Cys Ser Ser Leu Glu Gln Gly Gly Ala Cys Ala Ala Gln Ser Ile Leu
                165                 170                 175

Ile His Asp Cys Gln Gly Leu Gln Val Lys His Cys Thr Thr Ala Val
            180                 185                 190

Asn Ala Glu Gly Ser Ser Ala Asn Asp His Leu Gly Phe Gly Gly Gly
        195                 200                 205

Ala Phe Phe Val Thr Gly Ser Leu Ser Gly Glu Lys Ser Leu Tyr Met
    210                 215                 220

Pro Ala Gly Asp Met Val Val Ala Asn Cys Asp Gly Ala Ile Ser Phe
225                 230                 235                 240

Glu Gly Asn Ser Ala Asn Phe Ala Asn Gly Gly Ala Ile Ala Ala Ser
                245                 250                 255
```

-continued

```
Gly Lys Val Leu Phe Val Ala Asn Asp Lys Lys Thr Ser Phe Ile Glu
            260                 265                 270

Asn Arg Ala Leu Ser Gly Gly Ala Ile Ala Ala Ser Ser Asp Ile Ala
        275                 280                 285

Phe Gln Asn Cys Ala Glu Leu Val Phe Lys Gly Asn Cys Ala Ile Gly
    290                 295                 300

Thr Glu Asp Lys Gly Ser Leu Gly Gly Gly Ala Ile Ser Ser Leu Gly
305                 310                 315                 320

Thr Val Leu Leu Gln Gly Asn His Gly Ile Thr Cys Asp Lys Asn Glu
                325                 330                 335

Ser Ala Ser Gln Gly Gly Ala Ile Phe Gly Lys Asn Cys Gln Ile Ser
            340                 345                 350

Asp Asn Glu Gly Pro Val Val Phe Arg Asp Ser Thr Ala Cys Leu Gly
        355                 360                 365

Gly Gly Ala Ile Ala Ala Gln Glu Ile Val Ser Ile Gln Asn Asn Gln
    370                 375                 380

Ala Gly Ile Ser Phe Glu Gly Gly Lys Ala Ser Phe Gly Gly Gly Ile
385                 390                 395                 400

Ala Cys Gly Ser Phe Ser Ser Ala Gly Gly Ala Ser Val Leu Gly Thr
                405                 410                 415

Ile Asp Ile Ser Lys Asn Leu Gly Ala Ile Ser Phe Ser Arg Thr Leu
            420                 425                 430

Cys Thr Thr Ser Asp Leu Gly Gln Met Glu Tyr Gln Gly Gly Gly Ala
        435                 440                 445

Leu Phe Gly Glu Asn Ile Ser Leu Ser Glu Asn Ala Gly Val Leu Thr
    450                 455                 460

Phe Lys Asp Asn Ile Val Lys Thr Phe Ala Ser Asn Gly Lys Ile Leu
465                 470                 475                 480

Gly Gly Gly Ala Ile Leu Ala Thr Gly Lys Val Glu Ile Thr Asn Asn
                485                 490                 495

Ser Gly Gly Ile Ser Phe Thr Gly Asn Ala Arg Ala Pro Gln Ala Leu
            500                 505                 510

Pro Thr Gln Glu Glu Phe Pro Leu Phe Ser Lys Lys Glu Gly Arg Pro
        515                 520                 525

Leu Ser Ser Gly Tyr Ser Gly Gly Gly Ala Ile Leu Gly Arg Glu Val
    530                 535                 540

Ala Ile Leu His Asn Ala Ala Val Val Phe Glu Gln Asn Arg Leu Gln
545                 550                 555                 560

Cys Ser Glu Glu Glu Ala Thr Leu Leu Gly Cys Cys Gly Gly Gly Ala
                565                 570                 575

Val His Gly Met Asp Ser Thr Ser Ile Val Gly Asn Ser Ser Val Arg
            580                 585                 590

Phe Gly Asn Asn Tyr Ala Met Gly Gln Gly Val Ser Gly Gly Ala Leu
        595                 600                 605

Leu Ser Lys Thr Val Gln Leu Ala Gly Asn Gly Ser Val Asp Phe Ser
    610                 615                 620

Arg Asn Ile Ala Ser Leu Gly Gly Gly Ala Leu Gln Ala Ser Glu Gly
625                 630                 635                 640

Asn Cys Glu Leu Val Asp Asn Gly Tyr Val Leu Phe Arg Asp Asn Arg
                645                 650                 655

Gly Arg Val Tyr Gly Gly Ala Ile Ser Cys Leu Arg Gly Asp Val Val
            660                 665                 670

Ile Ser Gly Asn Lys Gly Arg Val Glu Phe Lys Asp Asn Ile Ala Thr
```

```
        675                 680                 685

Arg Leu Tyr Val Glu Glu Thr Val Glu Lys Val Glu Glu Val Glu Pro
    690                 695                 700

Ala Pro Glu Gln Lys Asp Asn Asn Glu Leu Ser Phe Leu Gly Ser Val
705                 710                 715                 720

Glu Gln Ser Phe Ile Thr Ala Ala Asn Gln Ala Leu Phe Ala Ser Glu
                725                 730                 735

Asp Gly Asp Leu Ser Pro Glu Ser Ser Ile Ser Ser Glu Glu Leu Ala
            740                 745                 750

Lys Arg Arg Glu Cys Ala Gly Gly Ala Ile Phe Ala Lys Arg Val Arg
        755                 760                 765

Ile Val Asp Asn Gln Glu Ala Val Val Phe Ser Asn Asn Phe Ser Asp
    770                 775                 780

Ile Tyr Gly Gly Ala Ile Phe Thr Gly Ser Leu Arg Glu Glu Asp Lys
785                 790                 795                 800

Leu Asp Gly Gln Ile Pro Glu Val Leu Ile Ser Gly Asn Ala Gly Asp
                805                 810                 815

Val Val Phe Ser Gly Asn Ser Ser Lys Arg Asp Glu His Leu Pro His
            820                 825                 830

Thr Gly Gly Gly Ala Ile Cys Thr Gln Asn Leu Thr Ile Ser Gln Asn
        835                 840                 845

Thr Gly Asn Val Leu Phe Tyr Asn Asn Val Ala Cys Ser Gly Gly Ala
    850                 855                 860

Val Arg Ile Glu Asp His Gly Asn Val Leu Leu Glu Ala Phe Gly Gly
865                 870                 875                 880

Asp Ile Val Phe Lys Gly Asn Ser Ser Phe Arg Ala Gln Gly Ser Asp
                885                 890                 895

Ala Ile Tyr Phe Ala Gly Lys Glu Ser His Ile Thr Ala Leu Asn Ala
            900                 905                 910

Thr Glu Gly His Ala Ile Val Phe His Asp Ala Leu Val Phe Glu Asn
        915                 920                 925

Leu Lys Glu Arg Lys Ser Ala Glu Val Leu Leu Ile Asn Ser Arg Glu
    930                 935                 940

Asn Pro Gly Tyr Thr Gly Ser Ile Arg Phe Leu Glu Ala Glu Ser Lys
945                 950                 955                 960

Val Pro Gln Cys Ile His Val Gln Gln Gly Ser Leu Glu Leu Leu Asn
                965                 970                 975

Gly Ala Thr Leu Cys Ser Tyr Gly Phe Lys Gln Asp Ala Gly Ala Lys
            980                 985                 990

Leu Val Leu Ala Ala Gly Ser Lys  Leu Lys Ile Leu Asp  Ser Gly Thr
        995                 1000                1005

Pro Val  Gln Gly His Ala Ile  Ser Lys Pro Glu Ala  Glu Ile Glu
    1010                1015                1020

Ser Ser  Ser Glu Pro Glu Gly  Ala
    1025                1030


<210> SEQ ID NO 10
<211> LENGTH: 3096
<212> TYPE: DNA
<213> ORGANISM: Chlamydia trachomatis

<400> SEQUENCE: 10

agttgcgtag atcttcatgc tggaggacag tctgtaaatg agctggtata tgtaggccct      60

caagcggttt tattgttaga ccaaattcga gatctattcg ttgggtctaa agatagtcag     120
```

-continued

```
gctgaaggac agtataggtt aattgtagga gatccaagtt ctttccaaga gaaagatgcg    180
gatactcttc ccgggaaggt agagcaaagt actttgttct cagtaaccaa tcccgtggtt    240
ttccaaggtg tggaccaaca ggatcaagtc tcttcccaag ggttaatttg tagttttacg    300
agcagcaacc ttgattctcc tcgtgacgga gaatcttttt taggtattgc ttttgttggg    360
gatagtagta aggctggaat cacattaact gacgtgaaag cttctttgtc tggagcggct    420
ttatattcta cagaagatct tatctttgaa aagattaagg gtggattgga atttgcatca    480
tgttcttctc tagaacaggg gggagcttgt gcagctcaaa gtattttgat tcatgattgt    540
caaggattgc aggttaaaca ctgtactaca gccgtgaatg ctgaggggtc tagtgcgaat    600
gatcatcttg gatttggagg aggcgctttc tttgttacgg gttctctttc tggagagaaa    660
agtctctata tgcctgcagg agatatggta gttgcgaatt gtgatggggc tatatctttt    720
gaaggaaaca gcgcgaactt tgctaatgga ggagcgattg ctgcctctgg gaaagtgctt    780
tttgtcgcta atgataaaaa gacttctttt atagagaacc gagctttgtc tggaggagcg    840
attgcagcct cttctgatat tgcctttcaa aactgcgcag aactagtttt caaaggcaat    900
tgtgcaattg gaacagagga taaaggttct ttaggtggag ggctatatc ttctctaggc    960
accgttcttt tgcaagggaa tcacgggata acttgtgata agaatgagtc tgcttcgcaa   1020
ggaggcgcca tttttggcaa aaattgtcag atttctgaca acgaggggcc agtggttttc   1080
agagatagta cagcttgctt aggaggaggc gctattgcag ctcaagaaat tgtttctatt   1140
cagaacaatc aggctgggat ttccttcgag ggaggtaagg ctagtttcgg aggaggtatt   1200
gcgtgtggat ctttttcttc cgcaggtggt gcttctgttt tagggaccat tgatatttcg   1260
aagaatttag gcgcgatttc gttctctcgt actttatgta cgacctcaga tttaggacaa   1320
atggagtacc agggaggagg agctctattt ggtgaaaata tttctctttc tgagaatgct   1380
ggtgtgctca cctttaaaga caacattgtg aagacttttg cttcgaatgg gaaaattctg   1440
ggaggaggag cgattttagc tactggtaag gtggaaatta ccaataattc cgaaggaatt   1500
tcttttacag gaaatgcgag agctccacaa gctcttccaa ctcaagagga gtttccttta   1560
ttcagcaaaa aagaagggcg accactctct tcaggatatt ctgggggagg agcgatttta   1620
ggaagagaag tagctattct ccacaacgct gcagtagtat ttgagcaaaa tcgtttgcag   1680
tgcagcgaag aagaagcgac attattaggt tgttgtggag gaggcgctgt tcatgggatg   1740
gatagcactt cgattgttgg caactcttca gtaagatttg gtaataatta cgcaatggga   1800
caaggagtct caggaggagc tcttttatct aaaacagtgc agttagctgg aaatggaagc   1860
gtcgattttt ctcgaaatat tgctagtttg ggaggaggag ctcttcaagc ttctgaagga   1920
aattgtgagc tagttgataa cggctatgtg ctattcagag ataatcgagg gagggtttat   1980
gggggtgcta tttcttgctt acgtggagat gtagtcattt ctggaaacaa gggtagagtt   2040
gaatttaaag acaacatagc aacacgtctt tatgtggaag aaactgtaga aaaggttgaa   2100
gaggtagagc cagctcctga gcaaaaagac aataatgagc tttctttctt agggagtgca   2160
gaacagagtt ttattactgc agctaatcaa gctcttttcg catctgaaga tggggattta   2220
tcacctgagt catccatttc ttctgaagaa cttgtgaaaa gaagagagtg tgctggagga   2280
gctatttttg caaaacgggt tcgtattgta gataaccaag aggccgttgt attctcgaat   2340
aacttctctg atatttatgg cggcgccatt tttacaggtt ctcttcgaga agaggataag   2400
ttagatgggc aaatccctga agtcttgatc tcaggcaatg caggggatgt tgtttttttcc   2460
```

-continued

```
ggaaattcct cgaagcgtga tgagcatctt cctcatacag gtgggggagc catttgtact   2520

caaaatttga cgatttctca gaatacaggg aatgttctgt tttataacaa cgtggcctgt   2580

tcgggaggag ctgttcgtat agaggatcat ggtaatgttc ttttagaagc ttttggagga   2640

gatattgttt ttaaaggaaa ttcttctttc agagcacaag gatccgatgc tatctatttt   2700

gcaggtaaag aatcgcatat tacagccctg aatgctacgg aaggacatgc tattgttttc   2760

cacgacgcat tagtttttga aaatctagaa gaaaggaaat ctgctgaagt attgttaatc   2820

aatagtcgag aaaatccagg ttacactgga tctattcgat ttttagaagc agaaagtaaa   2880

gttcctcaat gtattcatgt acaacaagga agccttgagt tgctaaatgg agccacatta   2940

tgtagttatg gttttaaaca agatgctgga gctaagttgg tattggctgc tggagctaaa   3000

ctgaagattt tagattcagg aactcctgta caacaagggc atgctatcag taaacctgaa   3060

gcagaaatcg agtcatcttc tgaaccagag ggtgca                              3096


<210> SEQ ID NO 11
<211> LENGTH: 3096
<212> TYPE: DNA
<213> ORGANISM: Chlamydia trachomatis

<400> SEQUENCE: 11

agttgcgtag atcttcatgc tggaggacag tctgtaaatg agctggtata tgtaggccct     60

caagcggttt tattgttaga ccaaattcga gatctattcg ttgggtctaa agatagtcag    120

gctgaaggac agtataggtt aattgtagga gatccaagtt ctttccaaga gaaagatgcg    180

gatactcttc ccgggaaggt agagcaaagt actttgttct cagtaaccaa tcccgtggtt    240

ttccaaggtg tggaccaaca ggatcaagtc tcttcccaag ggttaatttg tagttttacg    300

agcagcaacc ttgattctcc tcgtgacgga gaatcttttt taggtattgc ttttgttggg    360

gatagtagta aggctggaat cacattaact gacgtgaaag cttctttgtc tggagcggct    420

ttatattcta cagaagatct tatctttgaa aagattaagg gtggattgga atttgcatca    480

tgttcttctc tagaacaggg gggagcttgt gcagctcaaa gtattttgat tcatgattgt    540

caaggattgc aggttaaaca ctgtactaca gccgtgaatg ctgaggggtc tagtgcgaat    600

gatcatcttg gatttggagg aggcgctttc tttgttacgg gttctctttc tggagagaaa    660

agtctctata tgcctgcagg agatatggta gttgcgaatt gtgatggggc tatatctttt    720

gaaggaaaca gcgcgaactt tgctaatgga ggagcgattg ctgcctctgg gaaagtgctt    780

tttgtcgcta atgataaaaa gacttctttt atagagaacc gagctttgtc tggaggagcg    840

attgcagcct cttctgatat tgcctttcaa aactgcgcag aactagtttt caaaggcaat    900

tgtgcaattg gaacagagga taaaggttct ttaggtggag ggctatatc ttctctaggc    960

accgttcttt tgcaagggaa tcacgggata acttgtgata agaatgagtc tgcttcgcaa   1020

ggaggcgcca tttttggcaa aaattgtcag atttctgaca acgaggggcc agtggttttc   1080

agagatagta cagcttgctt aggaggaggc gctattgcag ctcaagaaat tgtttctatt   1140

cagaacaatc aggctgggat ttccttcgag ggaggtaagg ctagtttcgg aggaggtatt   1200

gcgtgtggat ctttttcttc cgcaggtggt gcttctgttt tagggaccat tgatatttcg   1260

aagaatttag gcgcgatttc gttctctcgt actttatgta cgacctcaga tttaggacaa   1320

atggagtacc agggaggagg agctctattt ggtgaaaata tttctctttc tgagaatgct   1380

ggtgtgctca cctttaaaga caacattgtg aagacttttg cttcgaatgg gaaaattctg   1440

ggaggaggag cgattttagc tactggtaag gtggaaatta ctaataattc cgaaggaatt   1500
```

-continued tcttttacag gaaatgcgag agctccacaa gctcttccaa ctcaagagga gtttccttta 1560
ttcagcaaaa aagaagggcg accactctct tcaggatatt ctgggggagg agcgatttta 1620
ggaagagaag tagctattct ccacaacgct gcagtagtat ttgagcaaaa tcgtttgcag 1680
tgcagcgaag aagaagcgac attattaggt tgttgtggag gaggcgctgt tcatgggatg 1740
gatagcactt cgattgttgg caactcttca gtaagatttg gtaataatta cgcaatggga 1800
caaggagtct caggaggagc tcttttatct aaaacagtgc agttagctgg gaatggaagc 1860
gtcgattttt ctcgaaatat tgctagtttg ggaggaggag ctcttcaagc ttctgaagga 1920
aattgtgagc tagttgataa cggctatgtg ctattcagag ataatcgagg gagggtttat 1980
gggggtgcta tttcttgctt acgtggagat gtagtcattt ctggaaacaa gggtagagtt 2040
gaatttaaag acaacatagc aacacgtctt tatgtggaag aaactgtaga aaaggttgaa 2100
gaggtagagc cagctcctga gcaaaaagac aataatgagc tttctttctt agggagagca 2160
gaacagagtt ttattactgc agctaatcaa gctcttttcg catctgaaga tggggattta 2220
tcacctgagt catccatttc ttctgaagaa cttgcgaaaa gaagagagtg tgctggagga 2280
gctatttttg caaaacgggt tcgtattgta gataaccaag aggccgttgt attctcgaat 2340
aacttctctg atatttatgg cggcgccatt tttacaggtt ctcttcgaga agaggataag 2400
ttagatgggc aaatccctga agtcttgatc tcaggcaatg caggggatgt tgtttttttcc 2460 ggaaattcct cgaagcgtga tgagcatctt cctcatacag gtgggggagc catttgtact 2520
caaaatttga cgatttctca gaatacaggg aatgttctgt tttataacaa cgtggcctgt 2580
tcgggaggag ctgttcgtat agaggatcat ggtaatgttc ttttagaagc ttttggagga 2640
gatattgttt ttaaaggaaa ttcttctttc agagcacaag gatccgatgc tatctatttt 2700
gcaggtaaag aatcgcatat tacagccctg aatgctacgg aaggacatgc tattgttttc 2760
cacgacgcat tagtttttga aaatctagaa gaaaggaaat ctgctgaagt attgttaatc 2820
aatagtcgag aaaatccagg ttacactgga tctattcgat ttttagaagc agaaagtaaa 2880
gttcctcaat gtattcatgt acaacaagga agccttgagt tgctaaatgg agccacatta 2940
tgtagttatg gttttaaaca agatgctgga gctaagttgg tattggctgc tggagctaaa 3000
ctgaagattt tagattcagg aactcctgta caacaagggc atgctatcag taaacctgaa 3060
gcagaaatcg agtcatcttc tgaaccagag ggtgca 3096

<210> SEQ ID NO 12
<211> LENGTH: 3093
<212> TYPE: DNA
<213> ORGANISM: Chlamydia trachomatis

<400> SEQUENCE: 12
agttgcgtag atcttcatgc tggaggacag tctgtaaatg agctggtata tgtaggccct 60
caagcggttt tattgttaga ccaaattcga gatctattcg ttgggtctaa agatagtcag 120
gctgaaggac agtataggtt aattgtagga gatccaagtt ctttccaaga gaaagatgca 180
gatactcttc ccgggaaggt agagcaaagt actttgttct cagtaaccaa tcccgtggtt 240
ttccaaggtg tggaccaaca ggatcaagtc tcttcccaag ggttaatttg tagttttacg 300
agcagcaacc ttgattctcc ccgtgacgga gaatcttttt taggtattgc ttttgttggg 360
gatagtagta aggctggaat cacattaact gacgtgaaag cttctttgtc tggagcggct 420
ttatattcta cagaagatct tatctttgaa aagattaagg gtggattgga atttgcatca 480

-continued

```
tgttcttctc tagaacaggg gggagcttgt gcagctcaaa gtattttgat tcatgattgt    540
caaggattgc aggttaaaca ctgtactaca gccgtgaatg ctgaggggtc tagtgcgaat    600
gatcatcttg gatttggagg aggcgctttc tttgttacgg gttctctttc tggagagaaa    660
agtctctata tgcctgcagg agatatggta gttgcgaatt gtgatggggc tatatctttt    720
gaaggaaaca gcgcgaactt tgctaatgga ggagcgattg ctgcctctgg gaaagtgctt    780
tttgtcgcta atgataaaaa gacttctttt atagagaacc gagctttgtc tggaggagcg    840
attgcagcct cttctgatat tgcctttcaa aactgcgcag aactagtttt caaaggcaat    900
tgtgcaattg gaacagagga taaaggttct ttaggtggag ggctatatc ttctctaggc    960
accgttcttt tgcaagggaa tcacgggata acttgtgata agaatgagtc tgcttcgcaa   1020
ggaggcgcca tttttggcaa aaattgtcag atttctgaca acgaggggcc agtggttttc   1080
agagatagta cagcttgctt aggaggaggc gctattgcag ctcaagaaat tgtttctatt   1140
cagaacaatc aggctgggat ttccttcgag ggaggtaagg ctagtttcgg aggaggtatt   1200
gcgtgtggat ctttttcttc cgcaggcggt gcttctgttt tagggactat tgatatttcg   1260
aagaatttag gcgcgatttc gttctctcgt actttatgta cgacctcaga tttaggacaa   1320
atggagtacc agggaggagg agctctattt ggtgaaaata tttctctttc tgagaatgct   1380
ggtgtgctca cctttaaaga caacattgtg aagacttttg cttcgaatgg gaaaattctg   1440
ggaggaggag cgattttagc tactggtaag gtggaaatta ccaataattc cggaggaatt   1500
tcttttacag gaaatgcgag agctccacaa gctcttccaa ctcaagagga gtttccttta   1560
ttcagcaaaa aagaagggcg accactctct tcaggatatt ctgggggagg agcgatttta   1620
ggaagagaag tagctattct ccacaacgct gcagtagtat ttgagcaaaa tcgtttgcag   1680
tgcagcgaag aagaagcgac attattaggt tgttgtggag gaggcgctgt tcatgggatg   1740
gatagcactt cgattgttgg caactcttca gtaagatttg gtaataatta cgcaatggga   1800
caaggagtct caggaggagc tcttttatct aaaacagtgc agttagctgg aaatggaagc   1860
gtcgattttt ctcgaaatat tgctagtttg ggaggaggag ctcttcaagc ttctgaagga   1920
aattgtgagc tagttgataa cggctatgtg ctattcagag ataatcgagg gagggtttat   1980
gggggtgcta tttcttgctt acgtggagat gtagtcattt ctggaaacaa gggtagagtt   2040
gaatttaaag acaacatagc aacacgtctt tatgtggaag aaactgtaga aaaggttgaa   2100
gaggtagagc cagctcctga gcaaaaagac aataatgagc tttctttctt agggagtgta   2160
gaacagagtt ttattactgc agctaatcaa gctcttttcg catctgaaga tggggattta   2220
tcacctgagt catccatttc ttctgaagaa cttgcgaaaa gaagagagtg tgctggagga   2280
gctattttg caaaacgggt tcgtattgta gataaccaag aggccgttgt attctcgaat   2340
aacttctctg atatttatgg cggcgccatt tttacaggtt ctcttcgaga agaggataag   2400
ttagatgggc aaatccctga agtcttgatc tcaggcaatg caggggatgt tgttttttcc   2460
ggaaattcct cgaagcgtga tgagcatctt cctcatacag gtgggggagc catttgtact   2520
caaaatttga cgatttctca gaatacaggg aatgttctgt tttataacaa cgtggcctgt   2580
tcgggaggag ctgttcgtat agaggatcat ggtaatgttc ttttagaagc ttttggagga   2640
gatattgttt ttaaaggaaa ttcttctttc agagcacaag gatccgatgc tatctatttt   2700
gcaggtaaag aatcgcatat tacagccctg aatgctacgg aaggacatgc tattgttttc   2760
cacgacgcat tagtttttga aaatctaaaa gaaaggaaat ctgctgaagt attgttaatc   2820
aatagtcgag aaaatccagg ttacactgga tctattcgat tttagaagc agaaagtaaa    2880
```

-continued

```
gttcctcaat gtattcatgt acaacaagga agccttgagt tgctaaatgg agctacatta   2940

tgtagttatg gttttaaaca agatgctgga gctaagttgg tattggctgc tggatctaaa   3000

ctgaagattt tagattcagg aactcctgta caagggcatg ctatcagtaa acctgaagca   3060

gaaatcgagt catcttctga accagagggt gca                                 3093
```